(12) United States Patent
Rothwell et al.

(10) Patent No.: US 11,149,302 B2
(45) Date of Patent: Oct. 19, 2021

(54) METHOD OF DNA SYNTHESIS

(71) Applicant: Touchlight IP Limited, London (GB)

(72) Inventors: Paul Rothwell, London (GB); Neil Porter, London (GB); Lydia Viney, London (GB); Thomas Adie, London (GB)

(73) Assignee: Touchlight IP Limited, London (GB)

( * ) Notice: Subject to any disclaimer, the term of this patent is extended or adjusted under 35 U.S.C. 154(b) by 409 days.

(21) Appl. No.: 15/551,476

(22) PCT Filed: Feb. 17, 2016

(86) PCT No.: PCT/GB2016/050399
§ 371 (c)(1),
(2) Date: Aug. 16, 2017

(87) PCT Pub. No.: WO2016/132129
PCT Pub. Date: Aug. 25, 2016

(65) Prior Publication Data
US 2018/0037943 A1    Feb. 8, 2018

(30) Foreign Application Priority Data
Feb. 17, 2015   (GB) ..................... 1502645

(51) Int. Cl.
*C12Q 1/6844* (2018.01)

(52) U.S. Cl.
CPC ...... *C12Q 1/6844* (2013.01); *C12Q 2521/113* (2013.01); *C12Q 2525/301* (2013.01); *C12Q 2565/537* (2013.01)

(58) Field of Classification Search
CPC .................... C12Q 2525/301; C12Q 2521/113
See application file for complete search history.

(56) References Cited

U.S. PATENT DOCUMENTS

2014/0308709 A1   10/2014   Kim et al.

FOREIGN PATENT DOCUMENTS

| EP | 2692870 A1 | 2/2014 |
| WO | 2006/108423 A2 | 10/2006 |
| WO | 2010/086626 A1 | 8/2010 |
| WO | 2012/017210 A1 | 2/2012 |

OTHER PUBLICATIONS

Du, Z et al., Identification and molecular characterization of a single-stranded circular DNA virus with similarities to Sclerotinia sclerotiorum hypovirulence-associated DNA virus 1, Arch. Virol., vol. 159, pp. 1527-1531 (Year: 2014).*
Mankertz, A. et al., Mapping and Characterization of the Origin of DNA Replication of Porcine Circovirus, J. Virol., vol. 71, pp. 2562-2566 (Year: 1997).*
Heinrich et al, "Linear Closed Mini DNA Generated by the Prokaryotic Cleaving-joining Enzyme TelN is Functional in Mammalian Cells," Journal of Molecular Medicine, vol. 80, No. 10, pp. 648-654 (2002).
Mardanov et al, "Conversion of Linear DNA with Hairpin Telomeres into a Circular Molecule in the Course of Phage N15 Lytic Replication," Journal of Molecular Biology, vol. 391, No. 2, pp. 261-268 (2009).
International Search Report for PCT/GB2016/050399 dated Apr. 28, 2016 (4 pages).

* cited by examiner

*Primary Examiner* — Teresa E Strzelecka
(74) *Attorney, Agent, or Firm* — Bookoff McAndrews, PLLC

(57) ABSTRACT

The present invention relates to an in vitro cell-free process for production of deoxyribonucleotides (DNAs) comprising at least one hairpin, corresponding DNA products and uses thereof, and oligonucleotides and kits useful in the process of the invention.

13 Claims, 30 Drawing Sheets

Specification includes a Sequence Listing.

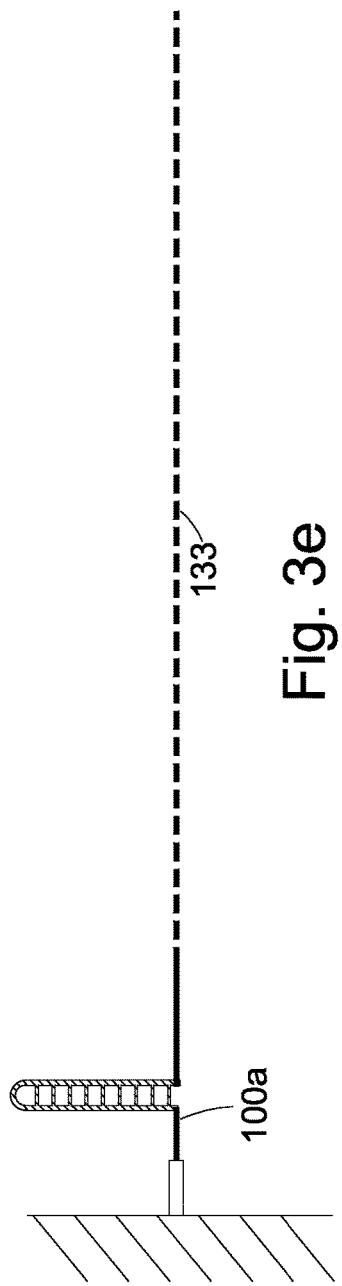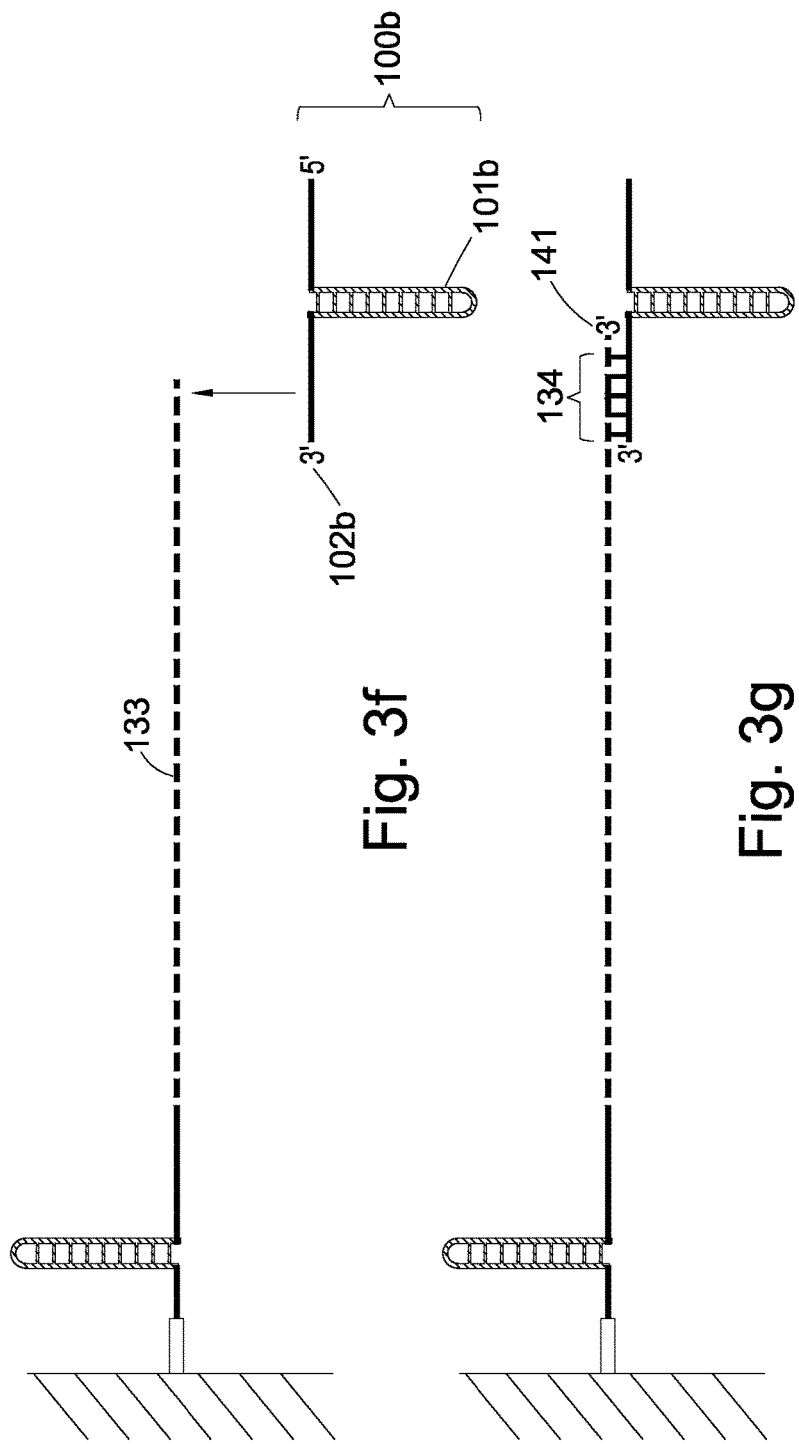

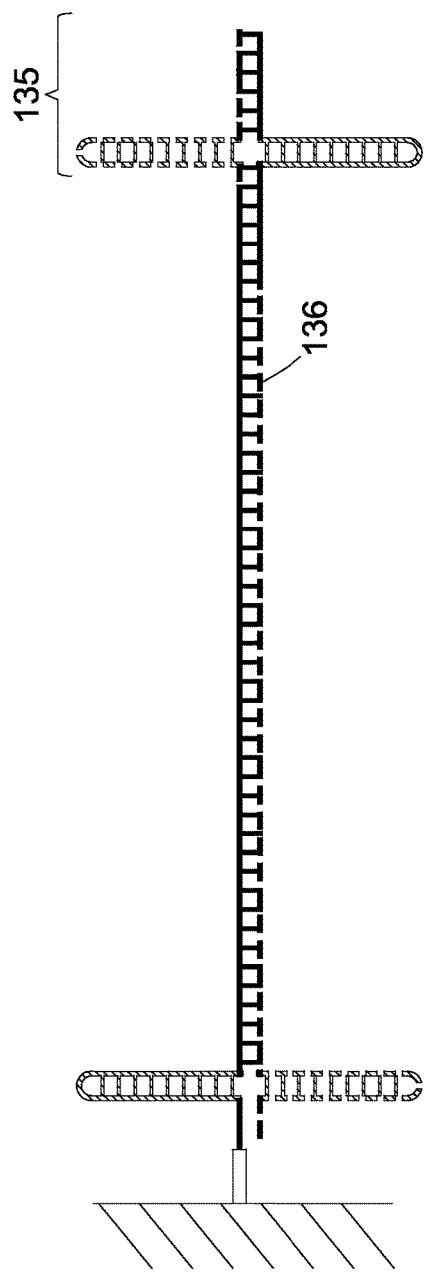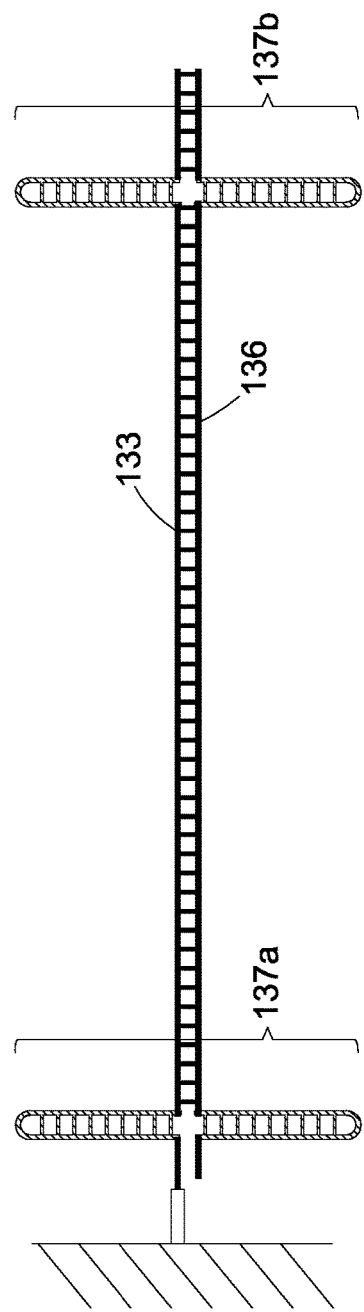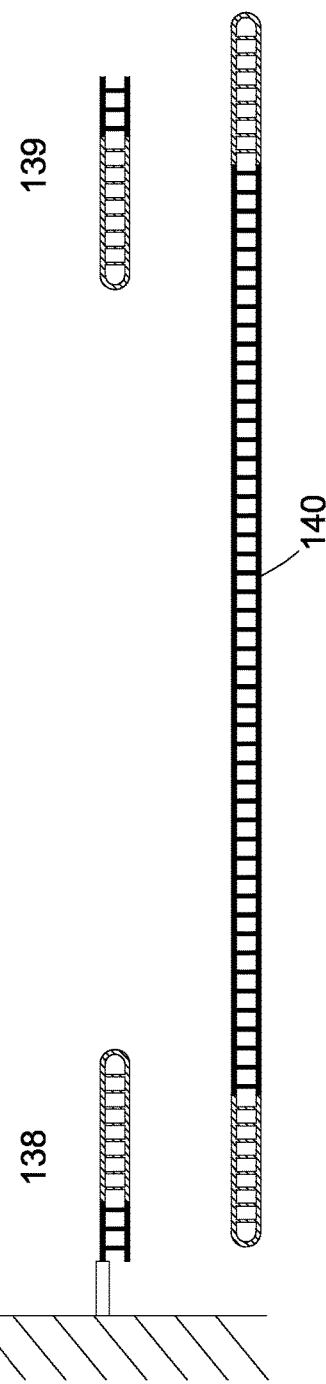

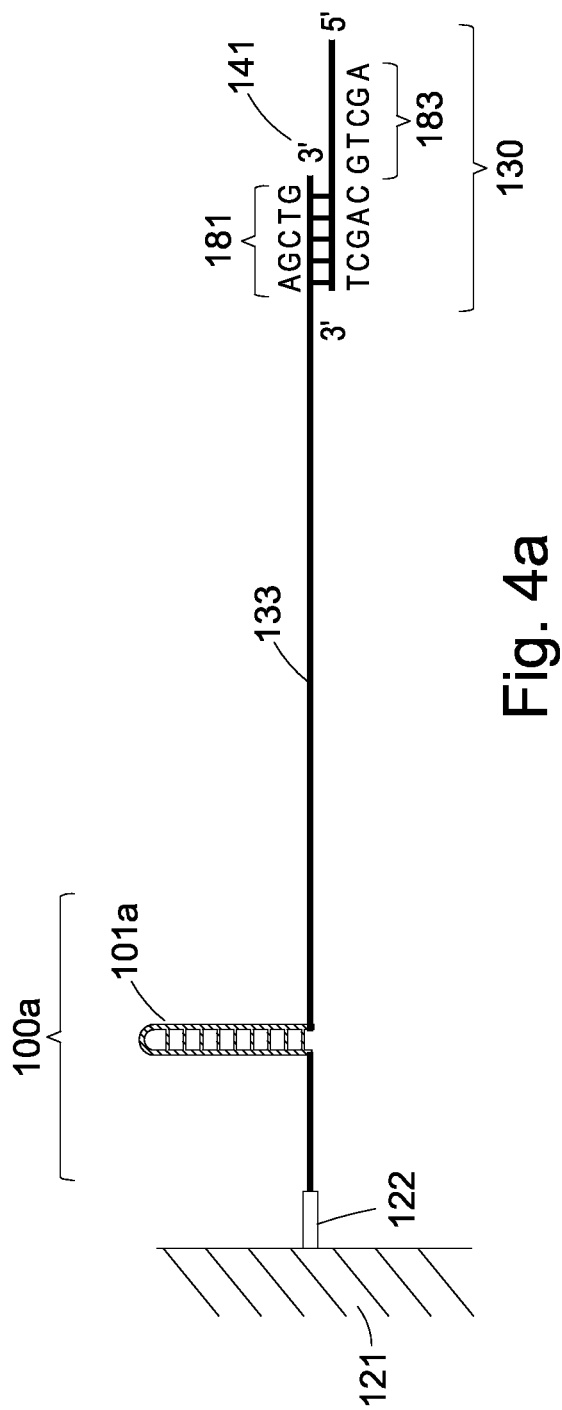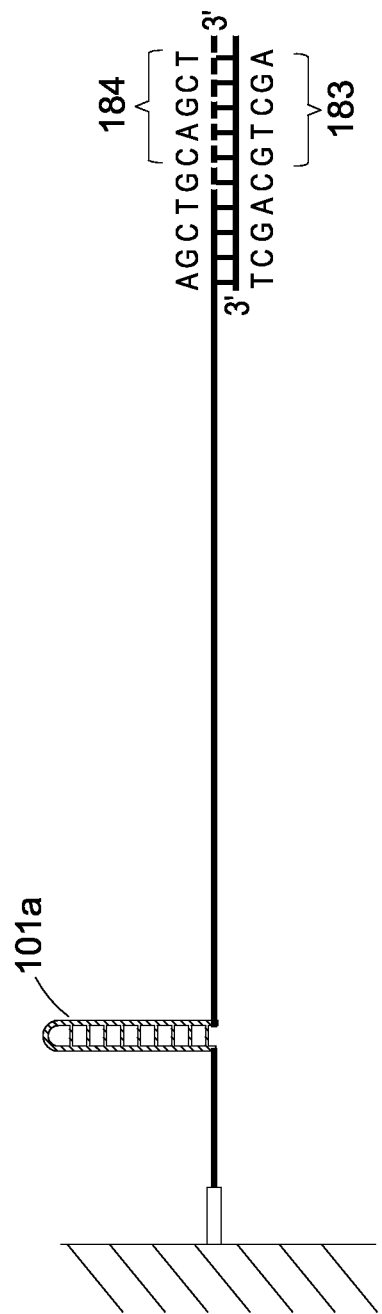
Fig. 4a
Fig. 4b

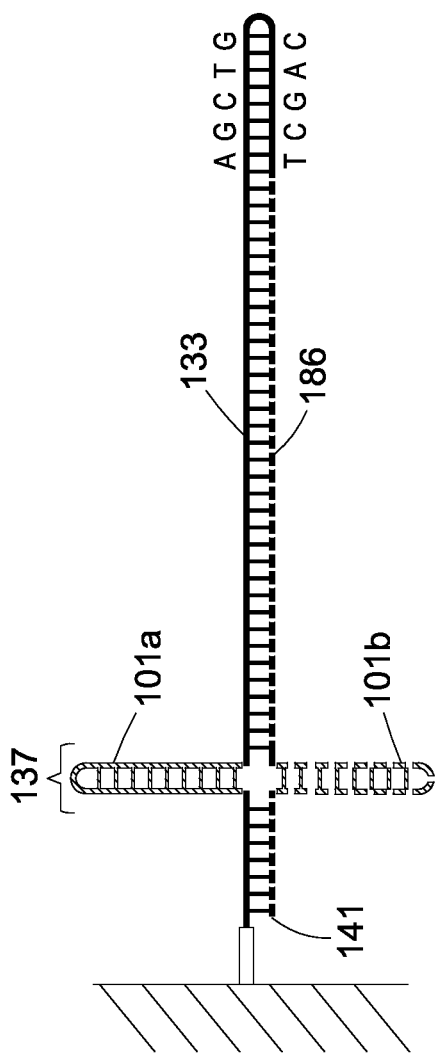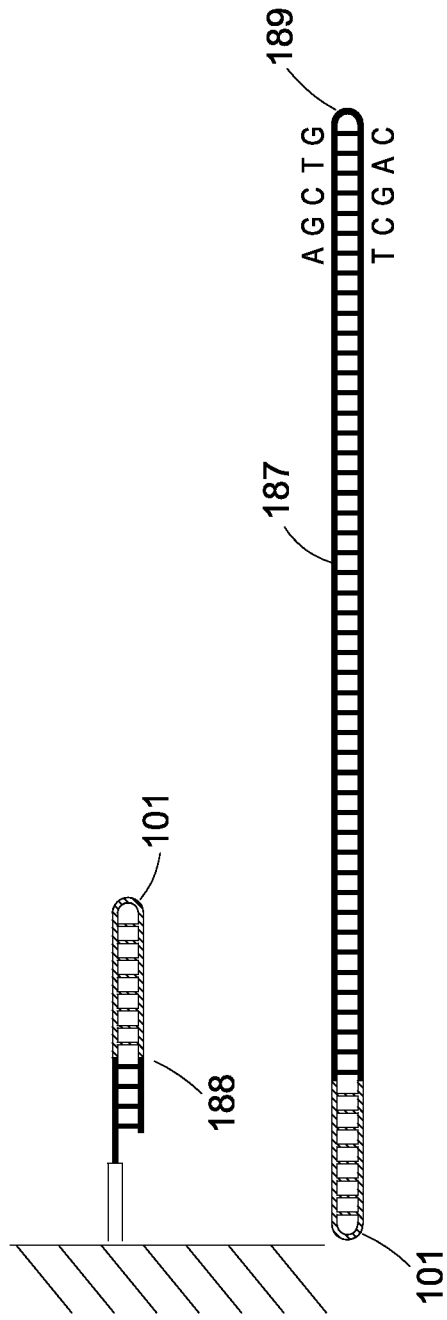

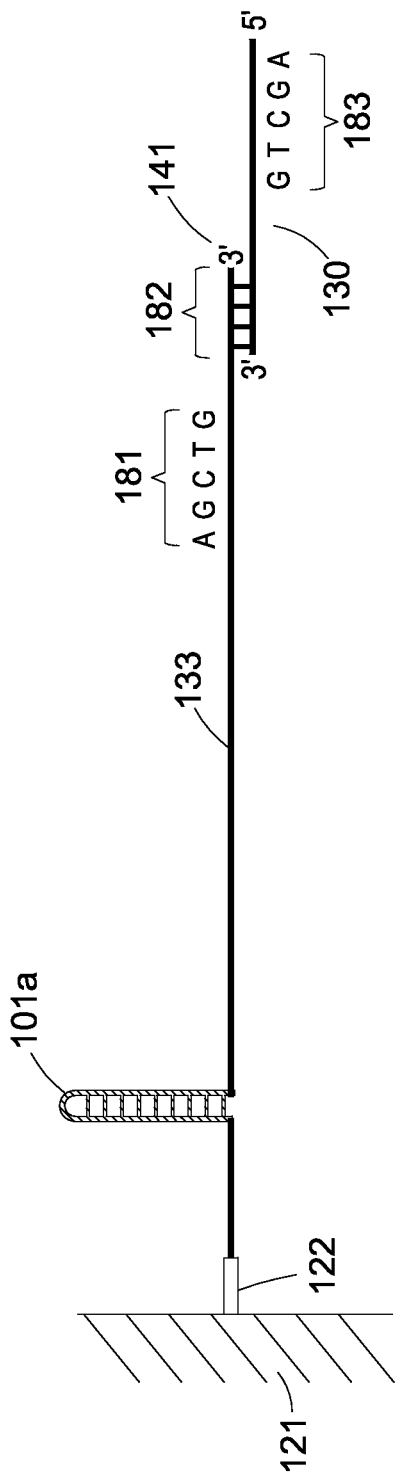
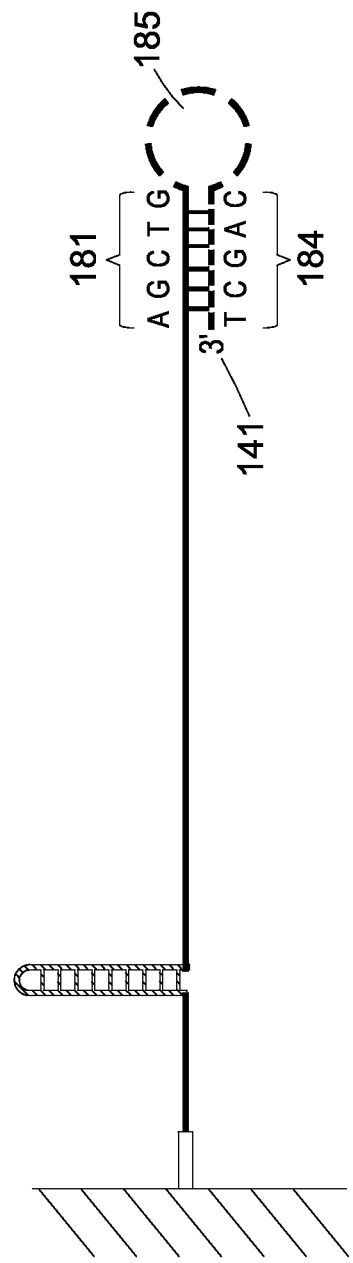
Fig. 4g
Fig. 4h

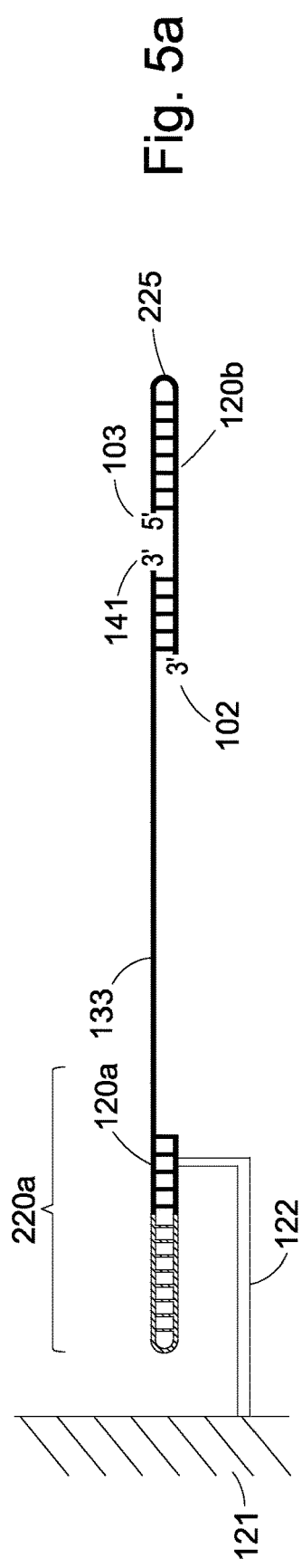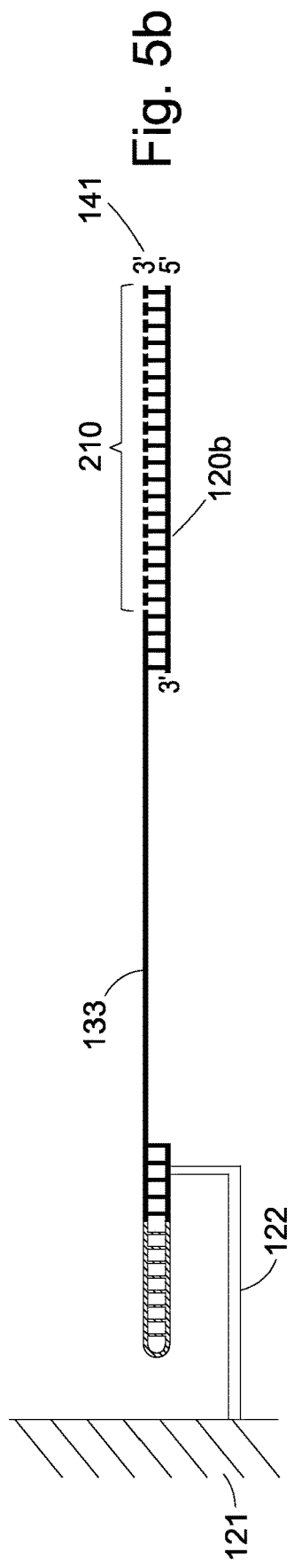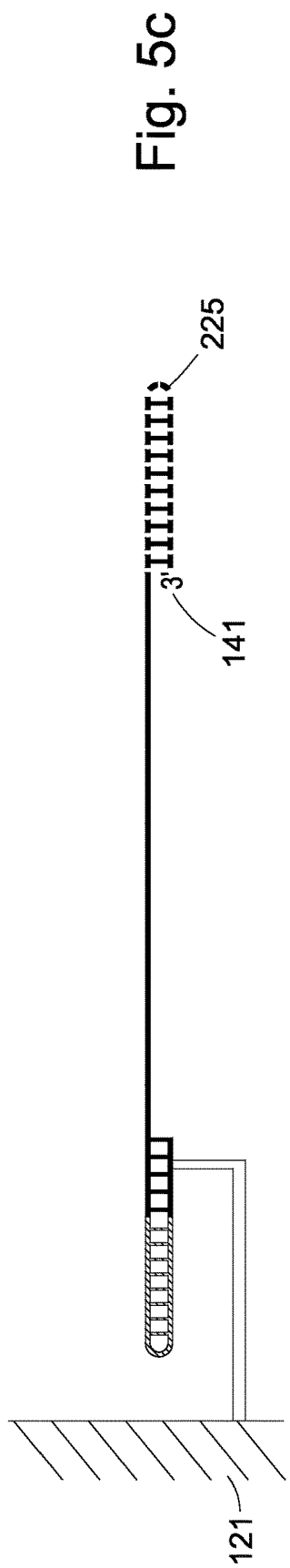

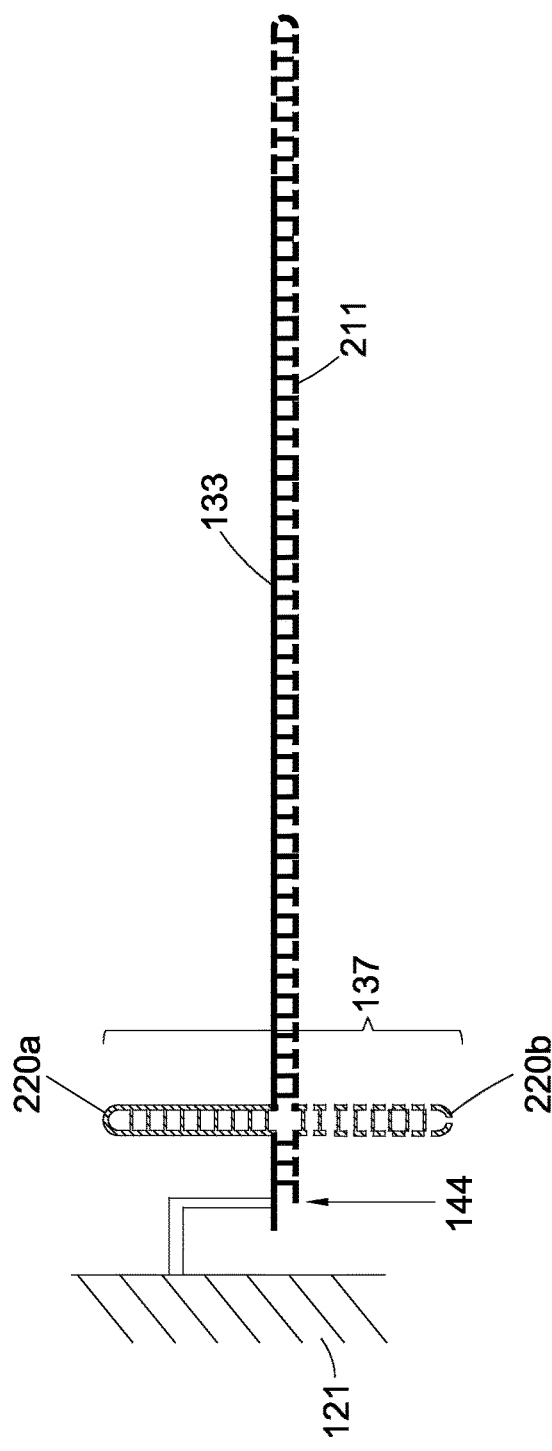
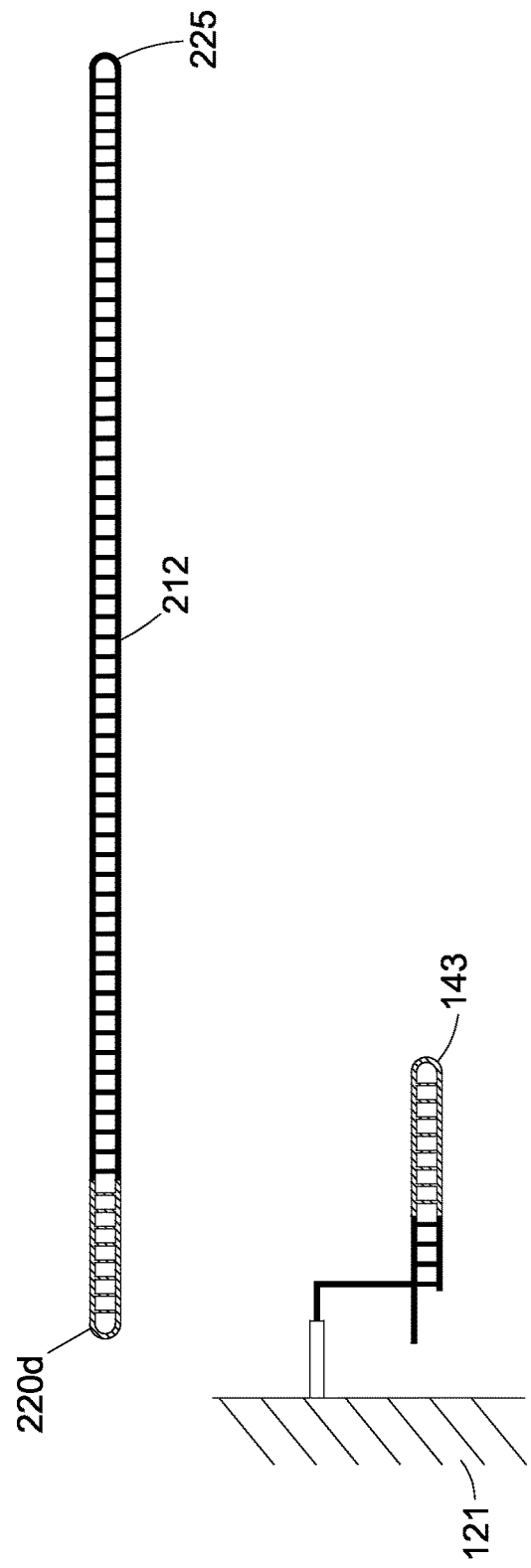

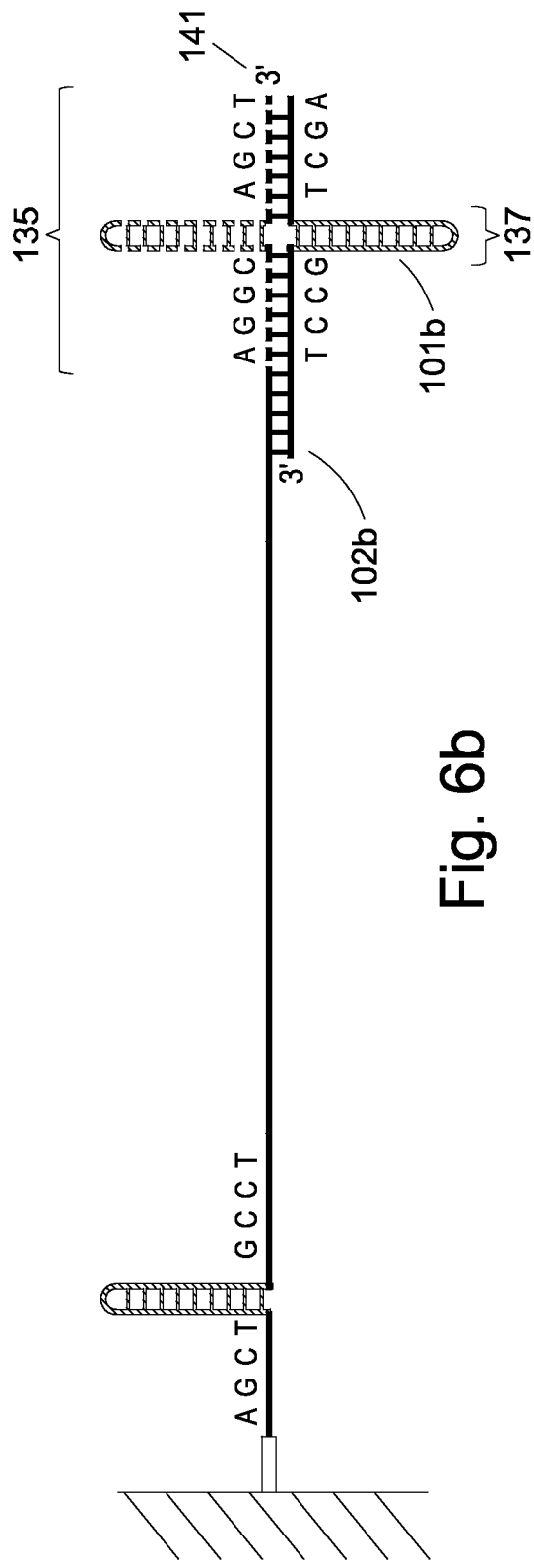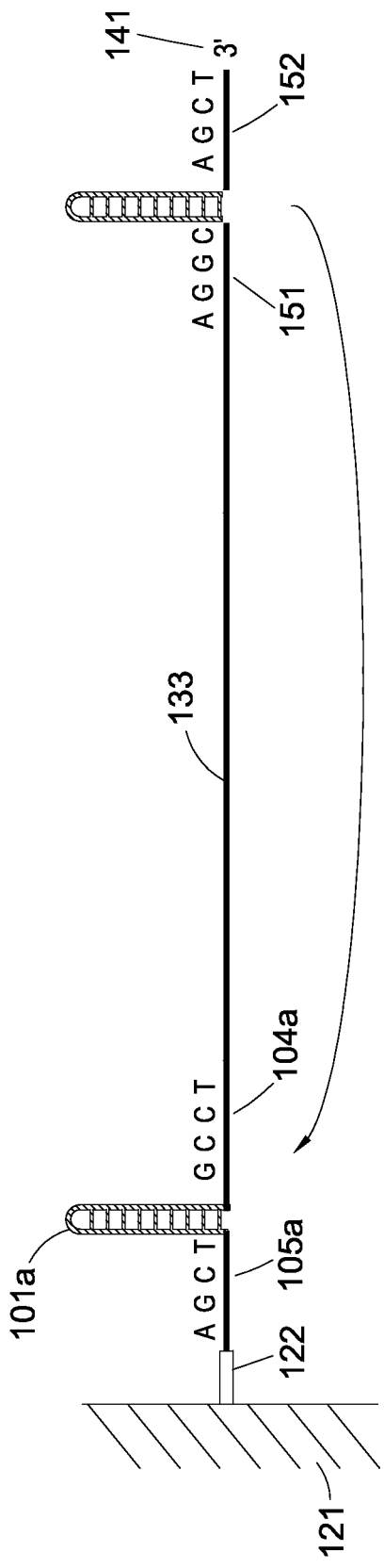

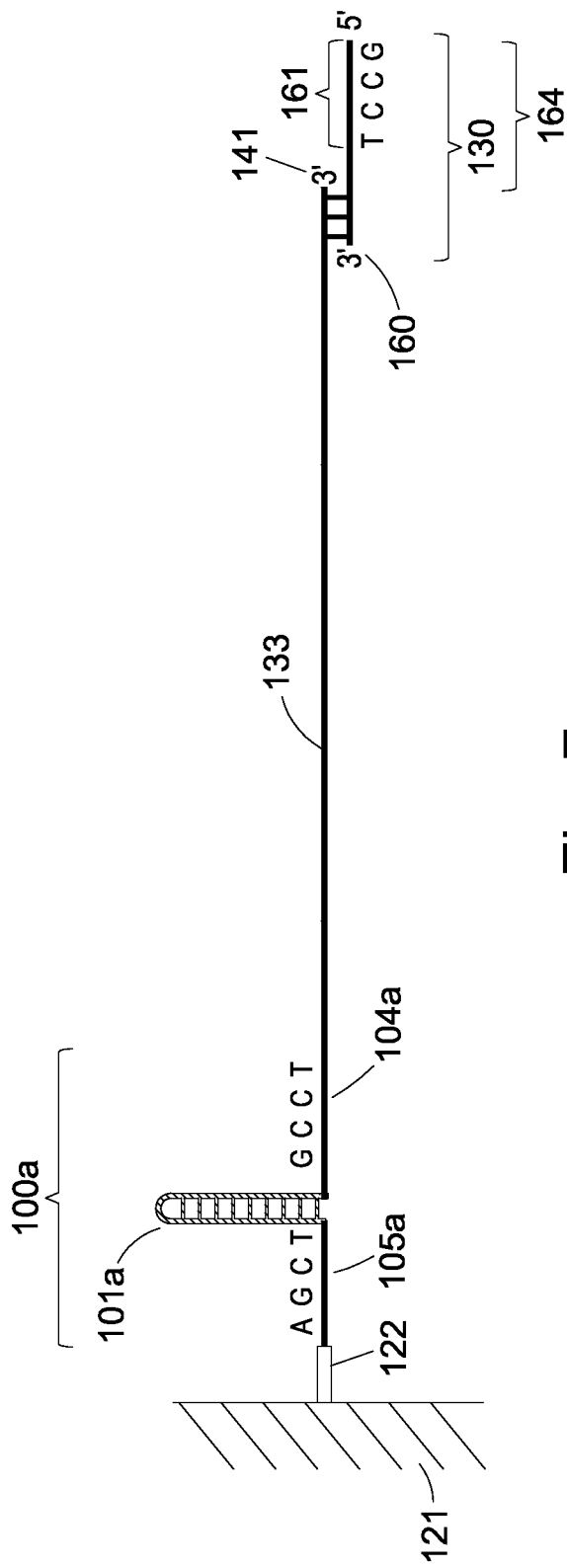
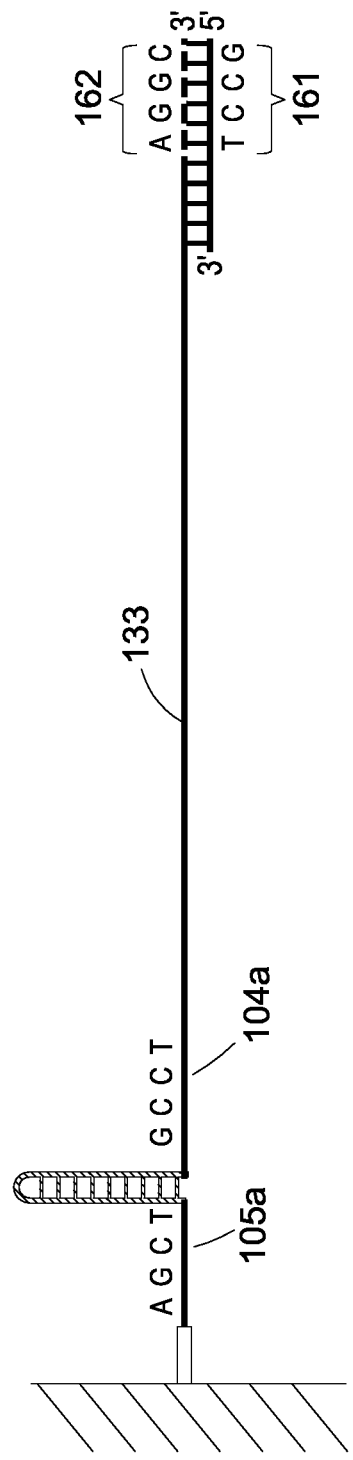
Fig. 7a
Fig. 7b

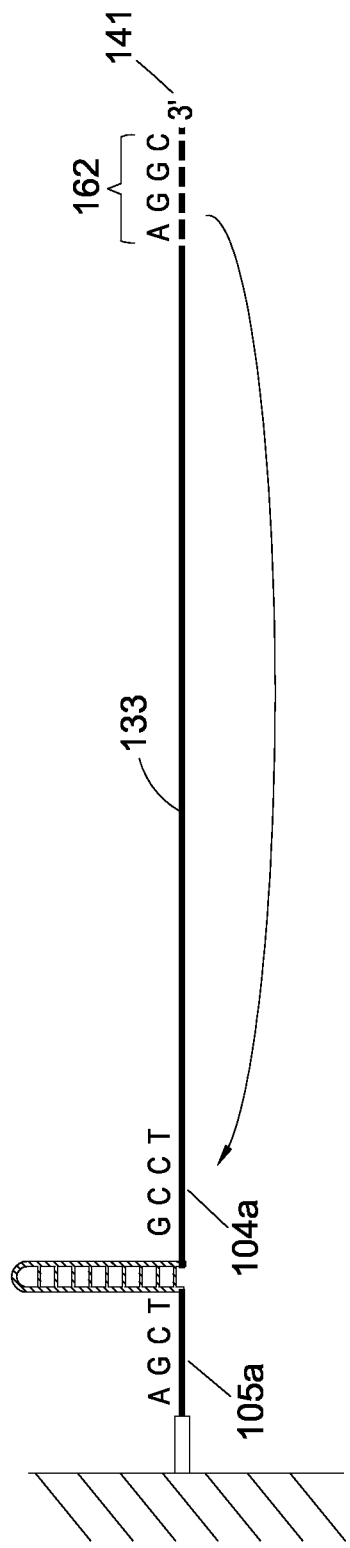
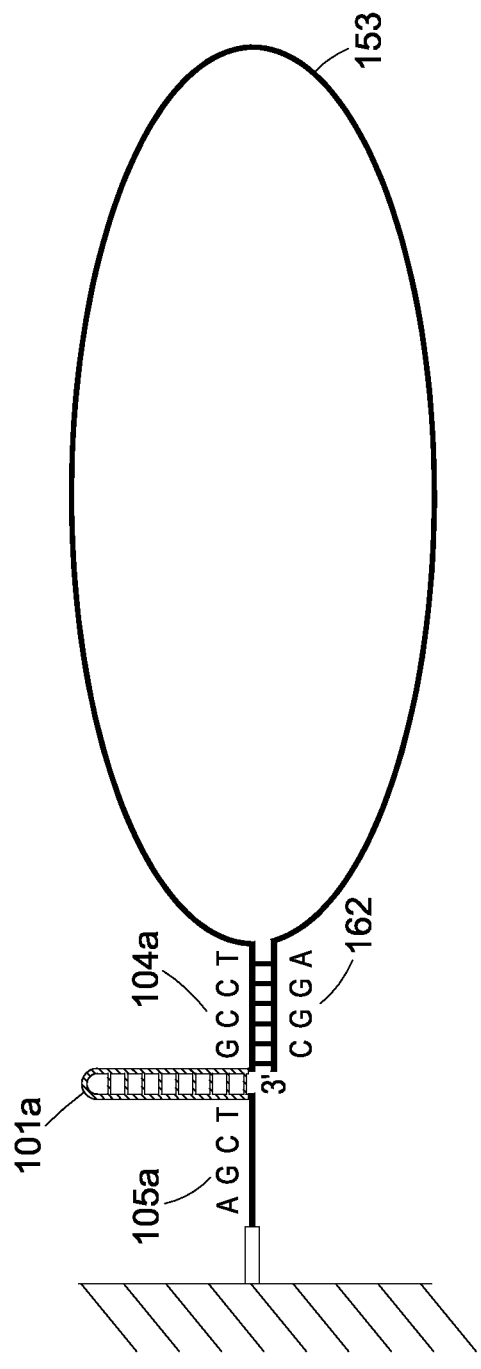
Fig. 7c
Fig. 7d

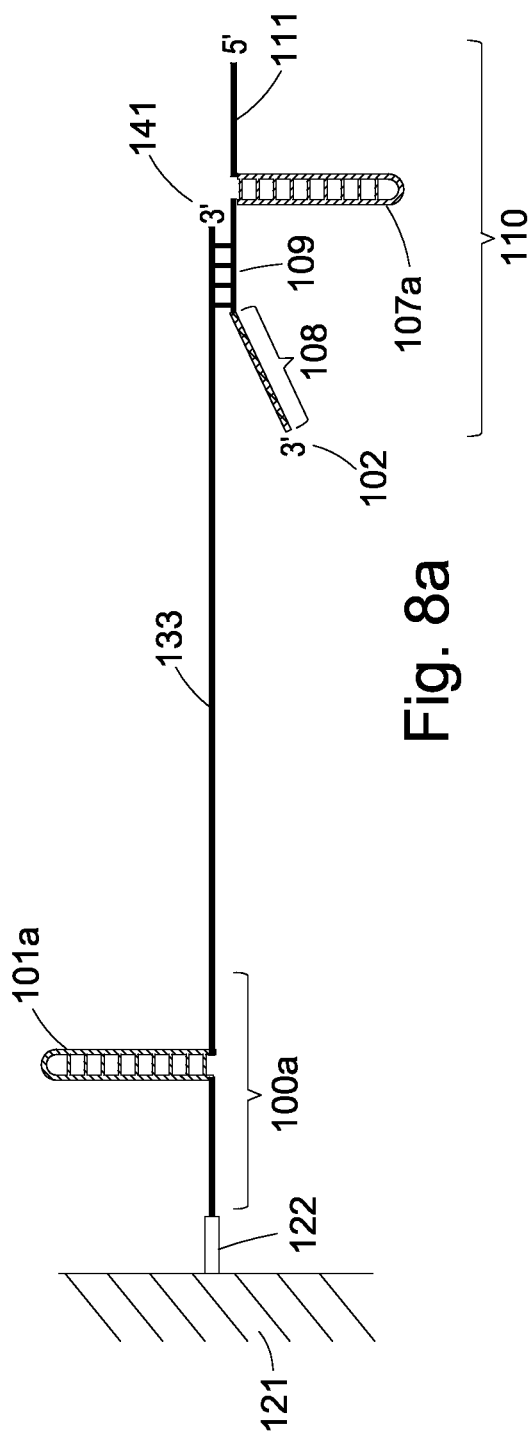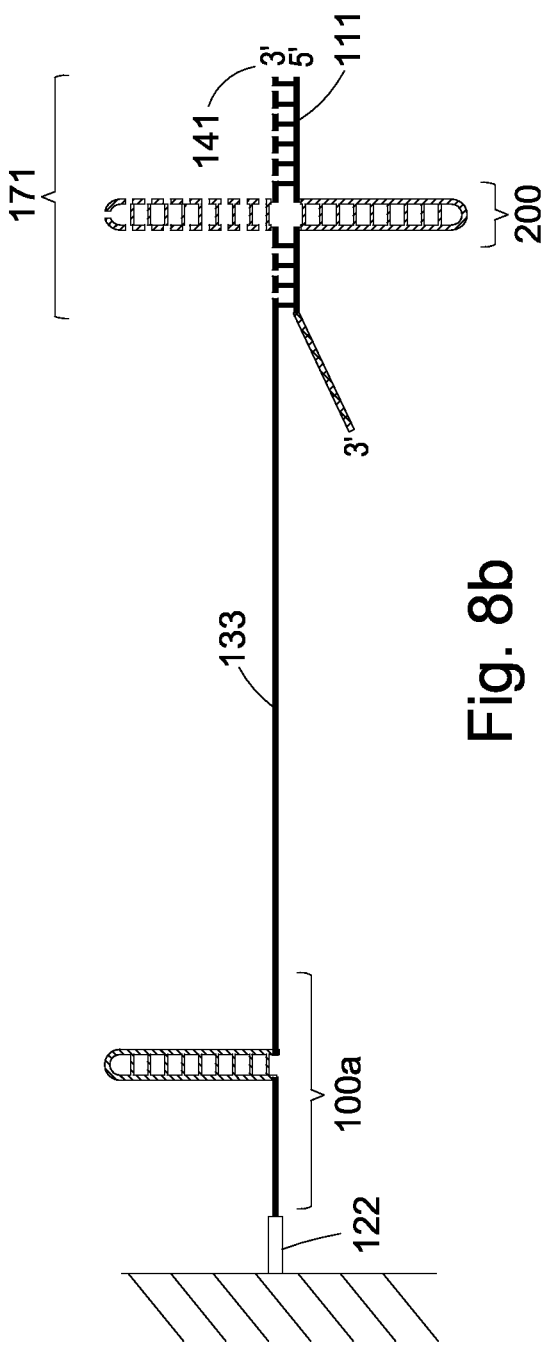

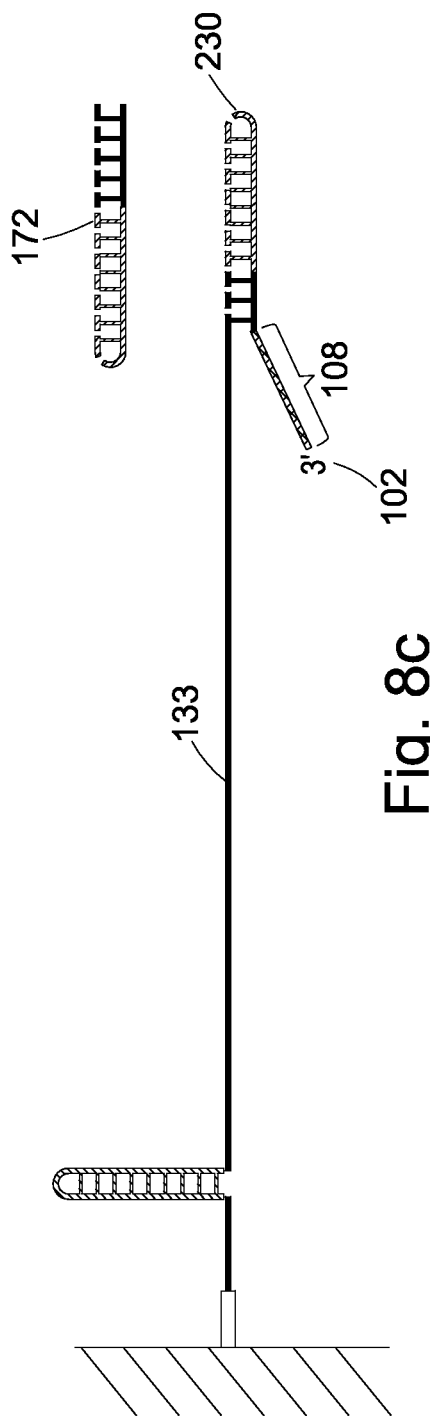
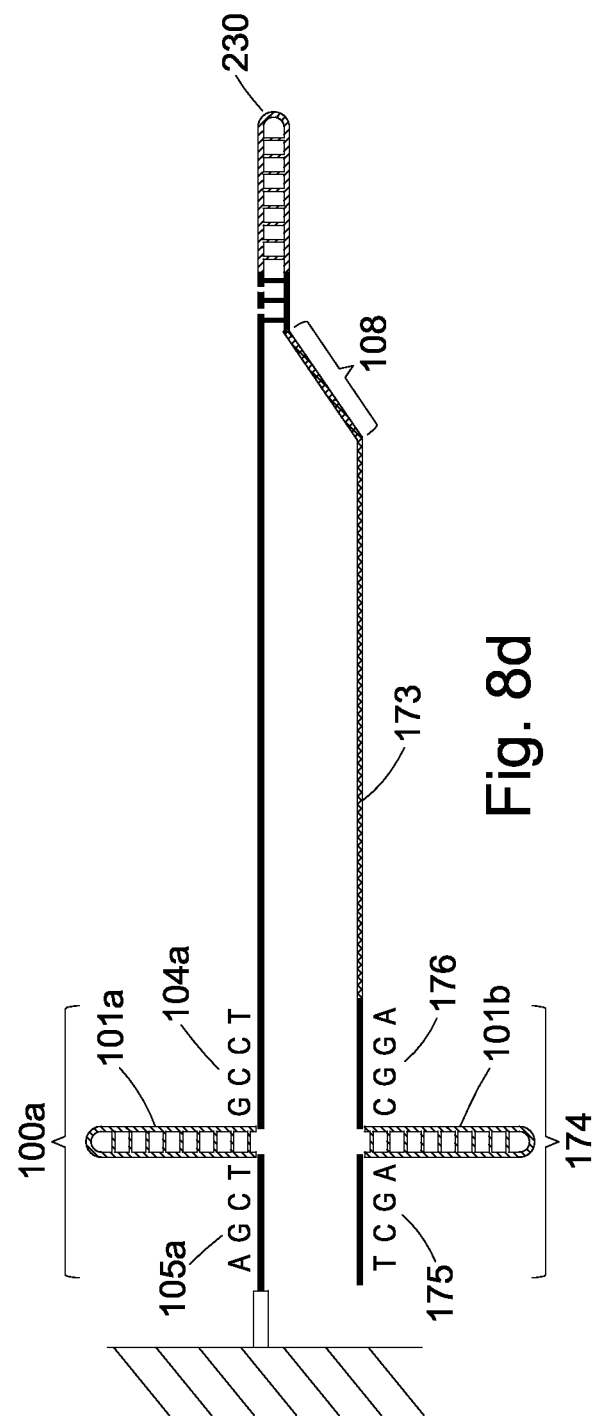

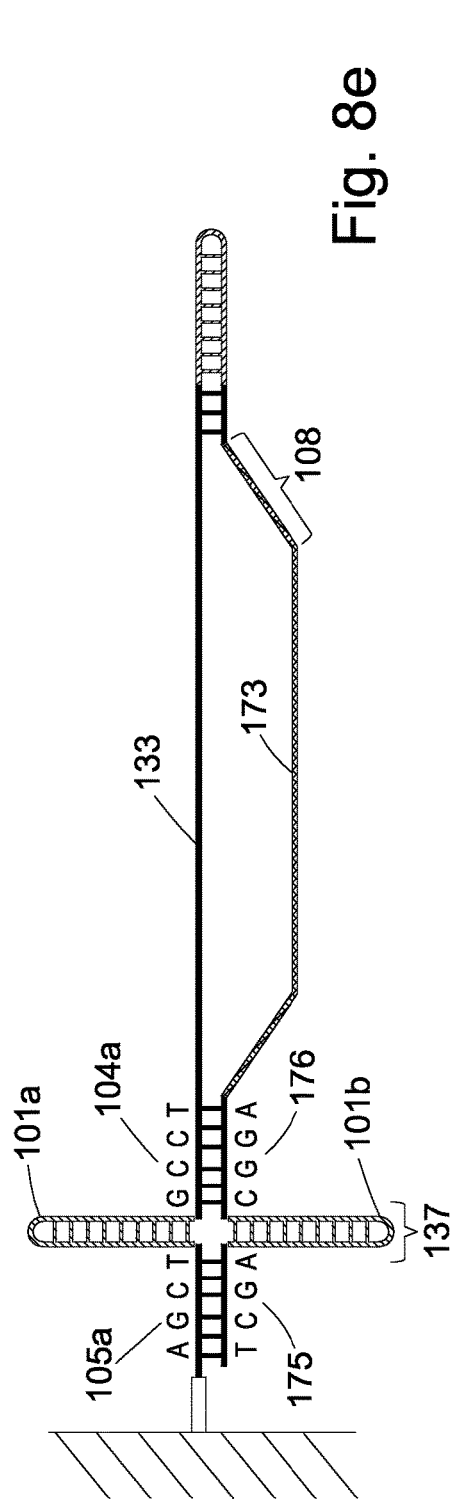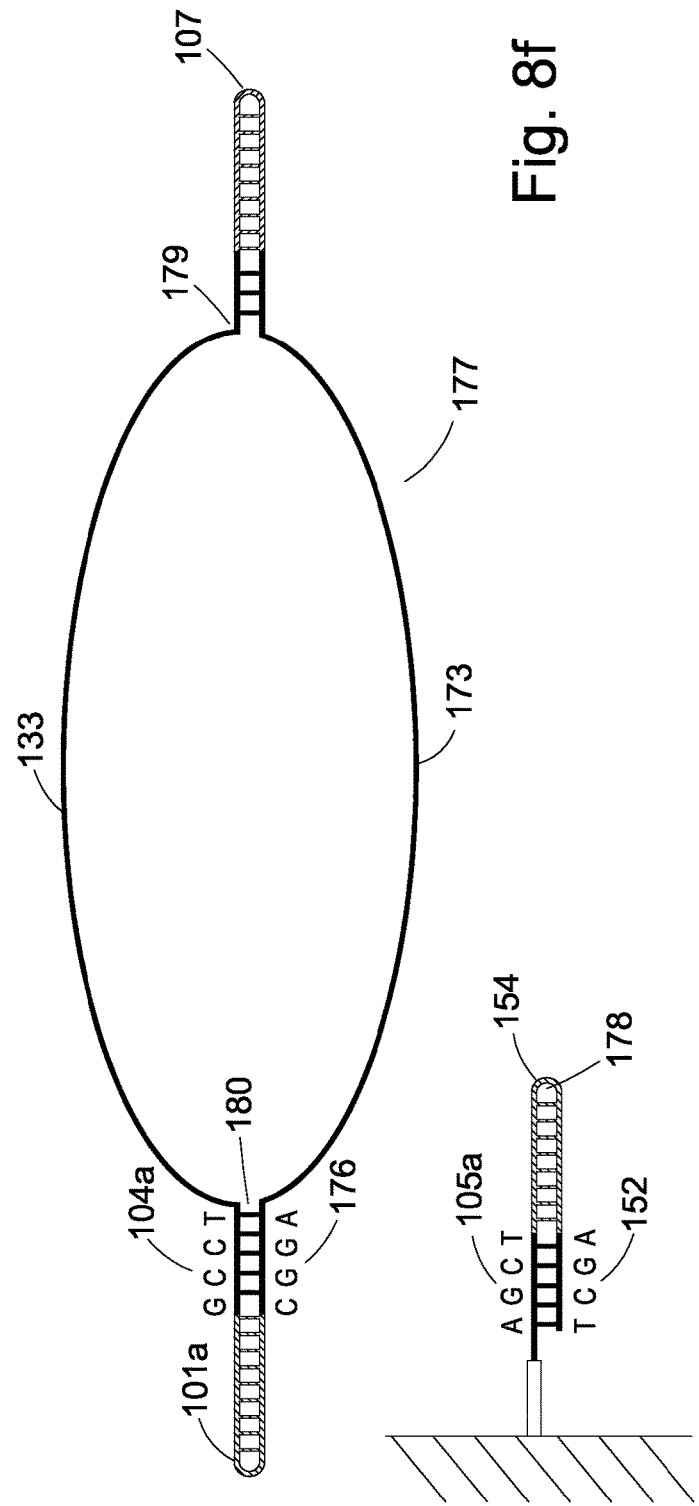

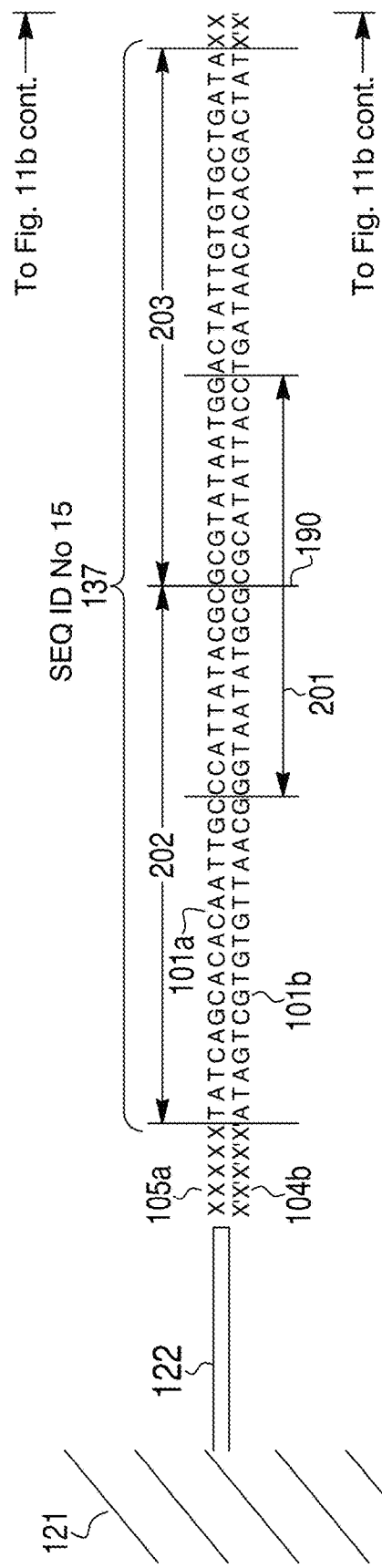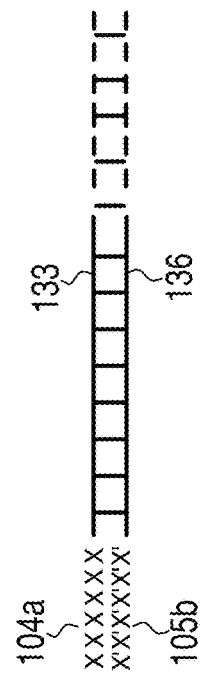
FIG. 11b
FIG. 11b cont.

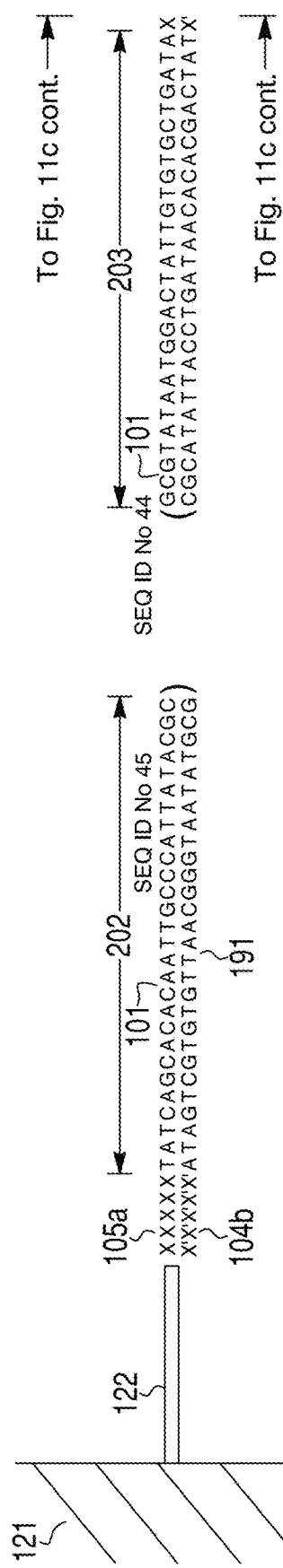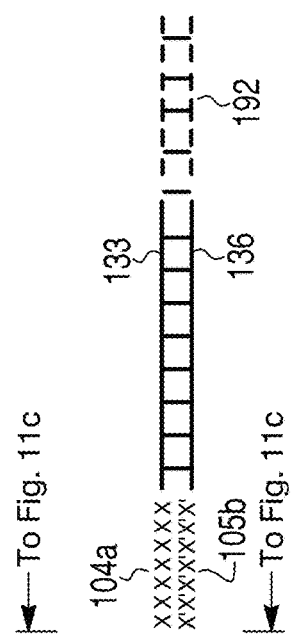
FIG. 11c
FIG. 11c cont.

FIG. 13

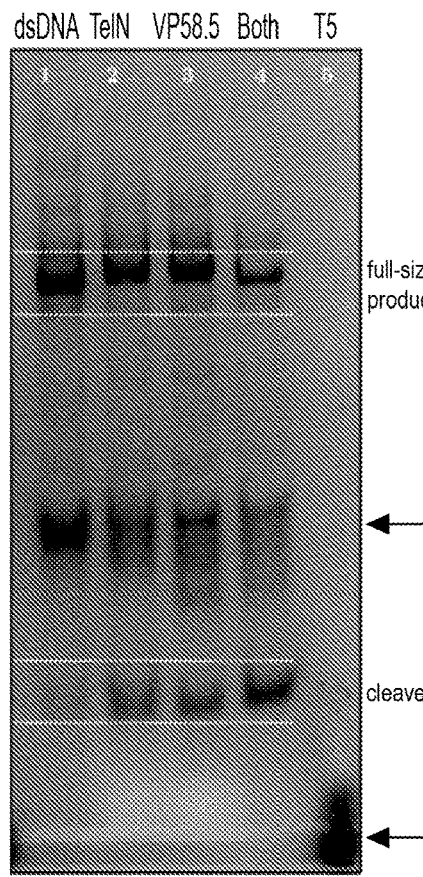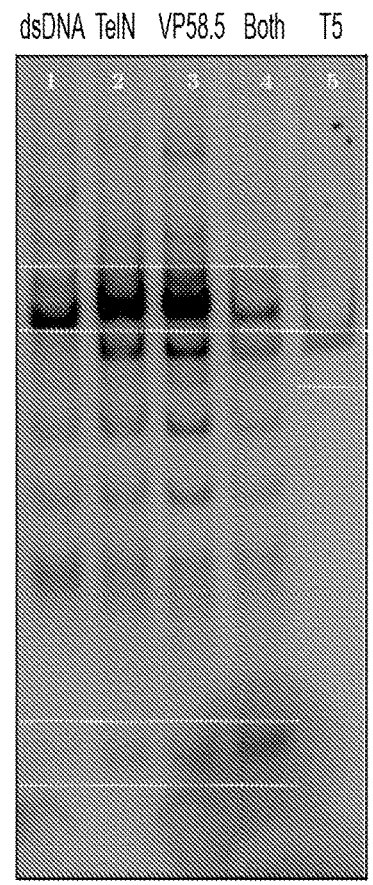
Fig. 14
Fig. 15
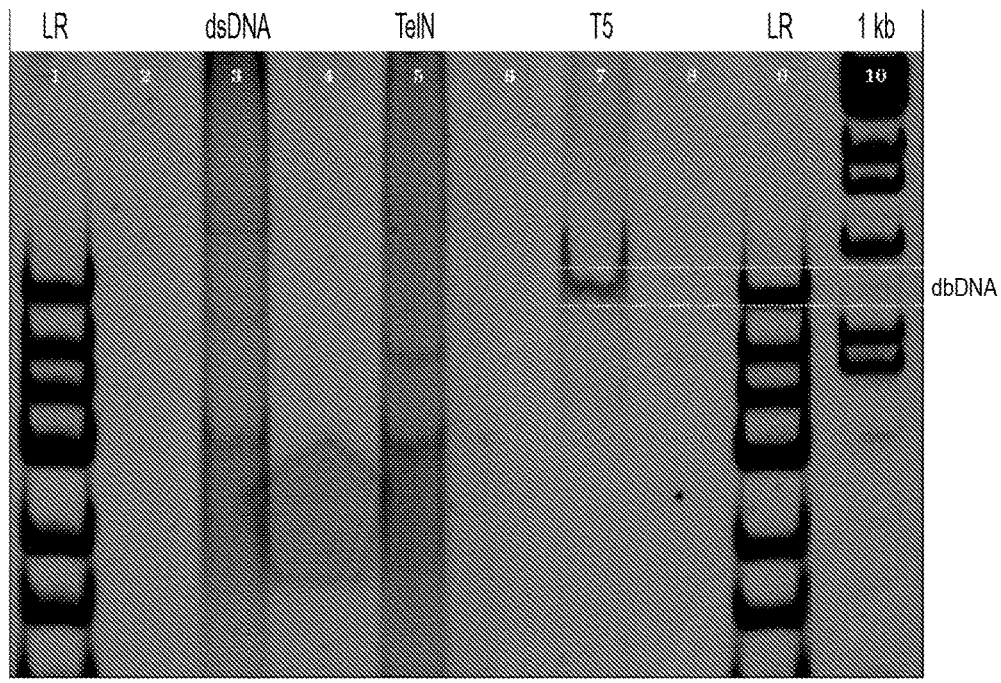
Fig. 16

SEQUENCE LISTING

<160> NUMBER OF SEQ ID NOS: 47

<210> SEQ ID NO 1
<211> LENGTH: 1563
<212> TYPE: DNA
<213> ORGANISM: Halomonas aquamarina phage phiHAP-1
<220> FEATURE:
<221> NAME/KEY: misc_feature
<223> OTHER INFORMATION: Protelomerase

<400> SEQUENCE: 1

| | | | | | |
|---|---|---|---|---|---|
| atgagcggtg | agtcacgtag | aaaggtcgat | ttagcggaat | tgatagagtg | gttgctcagc | 60 |
| gagatcaaag | agatcgacgc | cgatgatgag | atgccacgta | aagagaaaac | caagcgcatg | 120 |
| gcgcggctgg | cacgtagctt | caaaacgcgc | ctgcatgatg | acaagcgccg | caaggattct | 180 |
| gagcggatcg | cggtcacgac | ctttcgccgc | tacatgacag | aagcgcgcaa | ggcggtgact | 240 |
| gcgcagaact | ggcgccatca | cagcttcgac | cagcagatcg | agcggctggc | cagccgctac | 300 |
| ccggcttatg | ccagcaagct | ggaagcgctc | ggcaagctga | ccgatatcag | cgccattcgt | 360 |
| atggcccacc | gcgagctgct | cgaccagatc | cgcaacgatg | acgacgctta | tgaggacatc | 420 |
| cgggcgatga | agctggacca | tgaaatcatg | cgccacctga | cgttgagctc | tgcacagaaa | 480 |
| agcacgctgg | ctgaagaggc | cagcgagacg | ctggaagagc | gcgcggtgaa | cacggtcgag | 540 |
| atcaactacc | actggttgat | ggagacggtt | tacgagctgc | tgagtaaccg | ggagagaatg | 600 |
| gtcgatgggg | agtatcgcgg | ctttttcagt | tacctagcgc | ttgggctggc | gctggccacc | 660 |
| gggcgtcgct | cgatcgaggt | gctgaagacc | ggacggatca | cgaaggtggg | cgagtatgag | 720 |
| ctggagttca | gcggccaggc | gaaaaagcgc | ggcggcgtcg | actatagcga | ggcttaccac | 780 |
| atttataccc | tggtgaaagc | tgacctggtg | atcgaagcgt | gggatgagct | tcgctcgctg | 840 |
| ccggaagctg | ctgagctgca | gggcatggac | aacagcgatg | tgaaccgccg | cacggcgaag | 900 |
| acgctcaaca | cgctcactaa | gcggatcttt | aacaacgatg | agcgcgtttt | caaggacagc | 960 |
| cgggcgatct | gggcgcggct | ggtgtttgag | ctgcacttct | cgcgcgacaa | gcgctggaag | 1020 |
| aaagtcaccg | aggacgtgtt | ctggcgtgag | atgctggggc | atgaggacat | ggatacacag | 1080 |
| cgcagctacc | gcgcctttaa | aatcgactac | gacgagccgg | atcaagccga | ccaggaagat | 1140 |
| tacgaacacg | ctagccgcct | cgccgcgctg | caggcgctgg | acggccatga | gcagcttgag | 1200 |
| agcagcgacg | cccaggcgcg | tgtgcatgcc | tgggtgaaag | cgcagatcga | gcaggagcct | 1260 |
| gacgcgaaaa | ttacgcagtc | tctgatcagc | cgggagctgg | gcgtttatcg | ccctgccata | 1320 |
| aaagcgtacc | tggagctggc | gcgagaggcg | ctcgacgcgc | cgaacgtcga | tctggacaag | 1380 |
| gtcgcggcgg | cagtgccgaa | ggaagtagcc | gaggcgaagc | cccggctgaa | cgcccaccca | 1440 |
| caaggggatg | gcaggtgggt | cggggtggct | tcaatcaacg | gggtggaagt | tgcacgggtg | 1500 |
| ggcaaccagg | caggccggat | cgaagcgatg | aaagcggcct | ataaagcggc | gggtgggcgc | 1560 |
| tga | | | | | | 1563 |

<210> SEQ ID NO 2
<211> LENGTH: 520
<212> TYPE: PRT
<213> ORGANISM: Halomonas aquamarina phage phiHAP-1
<220> FEATURE:
<221> NAME/KEY: MISC_FEATURE
<223> OTHER INFORMATION: Protelomerase

<400> SEQUENCE: 2

Met Ser Gly Glu Ser Arg Arg Lys Val Asp Leu Ala Glu Leu Ile Glu

```
  1               5                  10                 15
Trp Leu Leu Ser Glu Ile Lys Glu Ile Asp Ala Asp Glu Met Pro
                 20                 25                 30
Arg Lys Glu Lys Thr Lys Arg Met Ala Arg Leu Ala Arg Ser Phe Lys
                 35                 40                 45
Thr Arg Leu His Asp Asp Lys Arg Lys Asp Ser Glu Arg Ile Ala
 50                 55                 60
Val Thr Thr Phe Arg Arg Tyr Met Thr Glu Ala Arg Lys Ala Val Thr
 65                 70                 75                 80
Ala Gln Asn Trp Arg His His Ser Phe Asp Gln Gln Ile Glu Arg Leu
                 85                 90                 95
Ala Ser Arg Tyr Pro Ala Tyr Ala Ser Lys Leu Glu Ala Leu Gly Lys
                100                105                110
Leu Thr Asp Ile Ser Ala Ile Arg Met Ala His Arg Glu Leu Leu Asp
                115                120                125
Gln Ile Arg Asn Asp Asp Asp Ala Tyr Glu Asp Ile Arg Ala Met Lys
                130                135                140
Leu Asp His Glu Ile Met Arg His Leu Thr Leu Ser Ser Ala Gln Lys
145                150                155                160
Ser Thr Leu Ala Glu Ala Ser Glu Thr Leu Glu Arg Ala Val
                165                170                175
Asn Thr Val Glu Ile Asn Tyr His Trp Leu Met Glu Thr Val Tyr Glu
                180                185                190
Leu Leu Ser Asn Arg Glu Arg Met Val Asp Gly Glu Tyr Arg Gly Phe
                195                200                205
Phe Ser Tyr Leu Ala Leu Gly Leu Ala Leu Ala Thr Gly Arg Arg Ser
                210                215                220
Ile Glu Val Leu Lys Thr Gly Arg Ile Thr Lys Val Gly Glu Tyr Glu
225                230                235                240
Leu Glu Phe Ser Gly Gln Ala Lys Lys Arg Gly Gly Val Asp Tyr Ser
                245                250                255
Glu Ala Tyr His Ile Tyr Thr Leu Val Lys Ala Asp Leu Val Ile Glu
                260                265                270
Ala Trp Asp Glu Leu Arg Ser Leu Pro Glu Ala Ala Glu Leu Gln Gly
                275                280                285
Met Asp Asn Ser Asp Val Asn Arg Arg Thr Ala Lys Thr Leu Asn Thr
                290                295                300
Leu Thr Lys Arg Ile Phe Asn Asn Asp Glu Arg Val Phe Lys Asp Ser
305                310                315                320
Arg Ala Ile Trp Ala Arg Leu Val Phe Glu Leu His Phe Ser Arg Asp
                325                330                335
Lys Arg Trp Lys Lys Val Thr Glu Asp Val Phe Trp Arg Glu Met Leu
                340                345                350
Gly His Glu Asp Met Asp Thr Gln Arg Ser Tyr Arg Ala Phe Lys Ile
                355                360                365
Asp Tyr Asp Glu Pro Asp Gln Ala Gln Glu Asp Tyr Glu His Ala
                370                375                380
Ser Arg Leu Ala Ala Leu Gln Ala Leu Asp Gly His Glu Gln Leu Glu
385                390                395                400
Ser Ser Asp Ala Gln Ala Arg Val His Ala Trp Val Lys Ala Gln Ile
                405                410                415
Glu Gln Glu Pro Asp Ala Lys Ile Thr Gln Ser Leu Ile Ser Arg Glu
                420                425                430
```

Leu Gly Val Tyr Arg Pro Ala Ile Lys Ala Tyr Leu Glu Leu Ala Arg
        435                 440                 445

Glu Ala Leu Asp Ala Pro Asn Val Asp Leu Asp Lys Val Ala Ala Ala
    450                 455                 460

Val Pro Lys Glu Val Ala Glu Ala Lys Pro Arg Leu Asn Ala His Pro
465                 470                 475                 480

Gln Gly Asp Gly Arg Trp Val Gly Val Ala Ser Ile Asn Gly Val Glu
                485                 490                 495

Val Ala Arg Val Gly Asn Gln Ala Gly Arg Ile Glu Ala Met Lys Ala
            500                 505                 510

Ala Tyr Lys Ala Ala Gly Gly Arg
        515                 520

<210> SEQ ID NO 3
<211> LENGTH: 1854
<212> TYPE: DNA
<213> ORGANISM: Yersinia enterolytica phage PY54
<220> FEATURE:
<221> NAME/KEY: misc_feature
<223> OTHER INFORMATION: Protelomerase

<400> SEQUENCE: 3

```
atgaaaatcc attttcgcga tttagttagt ggtttagtta aagagatcga tgaaatagaa      60
aaatcagacc gggcgcaggg tgacaaaact cggcgttatc agggcgcggc cagaaagttc     120
aaaaatgccg tgtttatgga taaacggaaa tatcgcggta acggtatgaa gaatagaata     180
tcgttaacaa catttaataa atatttaagt cgagcacgtt ctcggtttga agaaaggctt     240
caccatagtt ttcctcaatc tatagcaact atctcaaata aatatcctgc attcagcgaa     300
ataataaaag atctggataa tagacccgct catgaagtta gaataaaact taagaatta      360 ataactcatc ttgaatccgg tgttaattta ttagaaaaaa taggtagctt agggaaaata     420
aaaccatcta cagctaaaaa aatagttagc ttaaaaaaaa tgtacccatc atgggctaat     480
gatctagata ctttaattag tactgaagat gctacagaat acaacaaaaa gttagagcaa     540
gggaccgacc tacttaacgc attacattct ctaaaagtaa accatgaagt tatgtatgca     600
ttaacgatgc agccttctga cagagctgca ttaaaagcta ggcatgacgc tgcccttcac     660
tttaaaaagc gtaacatcgt acctatcgat tatcccggct atatgcaacg aatgacggac     720
atactacatc ttccagatat agcttttgaa gattcgatgg catcacttgc ccctttagca     780
tttgctctag cagctgctag cggtcgcaga caaattgaaa tactaattac tggtgagttt     840
gacgccaaaa ataaaagcat cattaaattt tctggacaag caaaaaaaag aatggccgtt     900
tcaggtggac attatgaaat atacagtcta attgactcag agctattcat tcaacggtta     960 gagttttttac gttctcatag ctcaatactt cgattacaaa atttggaaat agcacatgat    1020
gaacatcgta ctgaactatc tgttattaac ggttttgtag ccaaaccttt aaatgatgca    1080
gcaaaacagt tctttgtcga tgacagaaga gtatttaaag atacccgtgc aatttacgct    1140
cgcatagcat atgaaaaatg gtttagaaca gatcctcgct gggcgaagtg cgacgaagat    1200
gttttcttct ctgaattatt aggccatgac gacccagata ctcagctggc atataaacaa    1260
ttcaagctgg taaatttcaa tccaaaatgg acacctaata tatcagatga aaccctcgg     1320 ttagctgcac ttcaagagct tgacaatgat atgcccggcc tagcacgtgg cgatgcggca    1380
gttcgcatac atgagtgggt taagagcaa ctggcgcaga accctgcggc aaaaataact     1440
gcataccaaa tcaagaaaaa tttaaattgt cgaaatgact tggccagccg atacatggca    1500
```

```
tggtgtgctg acgcgctagg ggttgttatt ggtgatgatg gacaggcaag gccagaagaa    1560
ctcccaccat cgctcgtgct tgatattaac gctgatgaca ctgacgctga agaagatgaa    1620
atagaggaag actttactga tgaggaaata gacgacaccg aattcgacgt atcagataac    1680
gccagtgatg aagataagcc cgaagataaa ccctcgctttg cagcaccaat tcgtagaagt    1740
gaggactctt ggctgattaa atttgaattt gctggcaagc aatatagctg ggagggtaat    1800
gccgaaagtg ttatcgatgc gatgaaacaa gcatggactg aaaatatgga gtaa          1854
```

<210> SEQ ID NO 4
<211> LENGTH: 617
<212> TYPE: PRT
<213> ORGANISM: Yersinia enterolytica phage PY54
<220> FEATURE:
<221> NAME/KEY: MISC_FEATURE
<223> OTHER INFORMATION: Protelomerase

<400> SEQUENCE: 4

```
Met Lys Ile His Phe Arg Asp Leu Val Ser Gly Leu Val Lys Glu Ile
1               5                   10                  15

Asp Glu Ile Glu Lys Ser Asp Arg Ala Gln Gly Asp Lys Thr Arg Arg
            20                  25                  30

Tyr Gln Gly Ala Ala Arg Lys Phe Lys Asn Ala Val Phe Met Asp Lys
        35                  40                  45

Arg Lys Tyr Arg Gly Asn Gly Met Lys Asn Arg Ile Ser Leu Thr Thr
    50                  55                  60

Phe Asn Lys Tyr Leu Ser Arg Ala Arg Ser Arg Phe Glu Glu Arg Leu
65                  70                  75                  80

His His Ser Phe Pro Gln Ser Ile Ala Thr Ile Ser Asn Lys Tyr Pro
                85                  90                  95

Ala Phe Ser Glu Ile Ile Lys Asp Leu Asp Asn Arg Pro Ala His Glu
            100                 105                 110

Val Arg Ile Lys Leu Lys Glu Leu Ile Thr His Leu Glu Ser Gly Val
        115                 120                 125

Asn Leu Leu Glu Lys Ile Gly Ser Leu Gly Lys Ile Lys Pro Ser Thr
130                 135                 140

Ala Lys Lys Ile Val Ser Leu Lys Lys Met Tyr Pro Ser Trp Ala Asn
145                 150                 155                 160

Asp Leu Asp Thr Leu Ile Ser Thr Glu Asp Ala Thr Glu Leu Gln Gln
                165                 170                 175

Lys Leu Glu Gln Gly Thr Asp Leu Leu Asn Ala Leu His Ser Leu Lys
            180                 185                 190

Val Asn His Glu Val Met Tyr Ala Leu Thr Met Gln Pro Ser Asp Arg
        195                 200                 205

Ala Ala Leu Lys Ala Arg His Asp Ala Ala Leu His Phe Lys Lys Arg
210                 215                 220

Asn Ile Val Pro Ile Asp Tyr Pro Gly Tyr Met Gln Arg Met Thr Asp
225                 230                 235                 240

Ile Leu His Leu Pro Asp Ile Ala Phe Glu Asp Ser Met Ala Ser Leu
                245                 250                 255

Ala Pro Leu Ala Phe Ala Leu Ala Ala Ser Gly Arg Arg Gln Ile
            260                 265                 270

Glu Ile Leu Ile Thr Gly Glu Phe Asp Ala Lys Asn Lys Ser Ile Ile
        275                 280                 285

Lys Phe Ser Gly Gln Ala Lys Lys Arg Met Ala Val Ser Gly Gly His
```

Tyr Glu Ile Tyr Ser Leu Ile Asp Ser Glu Leu Phe Ile Gln Arg Leu
305                 310                 315                 320

Glu Phe Leu Arg Ser His Ser Ser Ile Leu Arg Leu Gln Asn Leu Glu
            325                 330                 335

Ile Ala His Asp Glu His Arg Thr Glu Leu Ser Val Ile Asn Gly Phe
                340                 345                 350

Val Ala Lys Pro Leu Asn Asp Ala Ala Lys Gln Phe Phe Val Asp Asp
            355                 360                 365

Arg Arg Val Phe Lys Asp Thr Arg Ala Ile Tyr Ala Arg Ile Ala Tyr
370                 375                 380

Glu Lys Trp Phe Arg Thr Asp Pro Arg Trp Ala Lys Cys Asp Glu Asp
385                 390                 395                 400

Val Phe Phe Ser Glu Leu Leu Gly His Asp Asp Pro Asp Thr Gln Leu
                405                 410                 415

Ala Tyr Lys Gln Phe Lys Leu Val Asn Phe Asn Pro Lys Trp Thr Pro
            420                 425                 430

Asn Ile Ser Asp Glu Asn Pro Arg Leu Ala Ala Leu Gln Glu Leu Asp
            435                 440                 445

Asn Asp Met Pro Gly Leu Ala Arg Gly Asp Ala Ala Val Arg Ile His
450                 455                 460

Glu Trp Val Lys Glu Gln Leu Ala Gln Asn Pro Ala Ala Lys Ile Thr
465                 470                 475                 480

Ala Tyr Gln Ile Lys Lys Asn Leu Asn Cys Arg Asn Asp Leu Ala Ser
                485                 490                 495

Arg Tyr Met Ala Trp Cys Ala Asp Ala Leu Gly Val Val Ile Gly Asp
            500                 505                 510

Asp Gly Gln Ala Arg Pro Glu Glu Leu Pro Pro Ser Leu Val Leu Asp
            515                 520                 525

Ile Asn Ala Asp Asp Thr Asp Ala Glu Glu Asp Ile Glu Glu Asp
530                 535                 540

Phe Thr Asp Glu Glu Ile Asp Thr Glu Phe Asp Val Ser Asp Asn
545                 550                 555                 560

Ala Ser Asp Glu Asp Lys Pro Glu Asp Lys Pro Arg Phe Ala Ala Pro
                565                 570                 575

Ile Arg Arg Ser Glu Asp Ser Trp Leu Ile Lys Phe Glu Phe Ala Gly
            580                 585                 590

Lys Gln Tyr Ser Trp Glu Gly Asn Ala Glu Ser Val Ile Asp Ala Met
            595                 600                 605

Lys Gln Ala Trp Thr Glu Asn Met Glu
610                 615

<210> SEQ ID NO 5
<211> LENGTH: 1923
<212> TYPE: DNA
<213> ORGANISM: Klebsiella phage phiKO2
<220> FEATURE:
<221> NAME/KEY: misc_feature
<223> OTHER INFORMATION: Protelomerase

<400> SEQUENCE: 5
atgcgtaagg tgaaaattgg tgagctaatc aattcgcttg tgagcgaggt cgaggcaatc        60
gatgcctctg atcgtccgca aggcgataaa acgaagaaaa ttaaagccgc agcattaaaa       120
tataagaatg cattatttaa tgacaaagaa agtttcgcg gtaaaggttt agaaaaaaga       180

```
atttctgcca acacgttcaa ctcgtatatg agtcgggcaa ggaaaagatt tgatgataga      240
ttgcatcata actttgaaaa gaatgtaatt aaactatcag aaaatatcc tttatatagt       300
gaagaattat cttcgtggct ttctatgcct gcggcatcaa ttagacagca tatgtcaaga      360
ttgcaagcca agctaaaaga gataatgcca ttggcagaag acttatccaa tataaagatt     420
ggtacaaaaa atagcgaagc aaaaataaat aaactcgcta ataaatatcc tgaatggcaa     480
ttcgctatta gtgatttaaa tagcgaagat tggaaggata aaagagatta tctttataaa    540
ctattccaac aaggttcttc gctcctggaa gacttgaata acctgaaagt aaaccatgag   600
gttctctatc atctgcagct tagttctgcc gagcgaacct ctatccagca gcgctgggcc   660
aacgtcctca gcgagaaaaa gcgcaacgtt gtcgtgattg actatccgcg ctatatgcag  720
gccatctacg atataatcaa caagcctata gtttcgttcg atttgactac tcgtcgtggt   780
atggccccgc tggcgttcgc ccttgccgcg ctatctggtc gccgaatgat tgaaatcatg   840
ctccagggtg aatttccgt cgcaggtaaa tatacagtaa cattcctggg gcaagctaaa     900
aaacgctcgg aagataaagg tatatcaagg aaaatatata ccttatgcga cgctacttta    960
tttgttagtt tggtaaatga acttcgctca tgccccgctg ctgcggattt tgatgaagta   1020
ataaaaggat atggcgaaaa tgacactcgc tcagaaaatg ggcgtattaa tgcaattctc   1080
gctacagctt ttaatccgtg ggtaaaaact ttcttaggcg atgaccgccg cgtttataaa   1140
gatagccgcg ctatttacgc ccgtattgcc tatgaaatgt tcttccgcgt tgaccctcgg   1200
tggaagaatg ttgatgagga tgtattcttc atggagattc tcggccatga cgatgaaaac   1260
acccaactgc actataagca gtttaaattg gctaacttct ccagaacatg gcgaccaaat   1320
gtcggcgagg agaatgcccg cctagcggcg ctgcaaaagc tggatagcat gatgccagat  1380
tttgccaggg gcgacgccgg ggttcgtatt catgagaccg tgaagcagct ggtggagcag  1440
gacccatcga taaaaatcac aaacagcacc ctgcgaccgt ttaacttcag taccaggctg   1500
attcctcgct acctggagtt tgccgccgat gcattgggcc agttcgtcgg tgaaaatggg  1560
caatggcaac tgaaggatga ggcgcctgca atagtcctgc ctgatgagga aattcttgag   1620
cctatggacg acgtcgatct cgatgacgaa aaccatgatg atgaaacgct ggatgacgat   1680
gagatcgaag tggacgaaag cgaaggagag gaactggagg aagcgggcga cgctgaagag   1740
gccgaggtgg ctgaacagga agagaagcac cctggcaagc caaactttaa agcgccgagg   1800
gataatggcg atggtaccta catggtggaa tttgaattcg gtggccgtca ttacgcctgg   1860
tccggtgccg ccggtaatcg ggtagaggca atgcaatctg cctggagtgc ctacttcaag   1920
tga                                                                 1923
```

<210> SEQ ID NO 6
<211> LENGTH: 640
<212> TYPE: PRT
<213> ORGANISM: Klebsiella phage phiKO2
<220> FEATURE:
<221> NAME/KEY: MISC_FEATURE
<223> OTHER INFORMATION: Protelomerase

<400> SEQUENCE: 6

```
Met Arg Lys Val Lys Ile Gly Glu Leu Ile Asn Ser Leu Val Ser Glu
1               5                   10                  15

Val Glu Ala Ile Asp Ala Ser Asp Arg Pro Gln Gly Asp Lys Thr Lys
            20                  25                  30

Lys Ile Lys Ala Ala Ala Leu Lys Tyr Lys Asn Ala Leu Phe Asn Asp
        35                  40                  45
```

-continued

```
Lys Arg Lys Phe Arg Gly Lys Gly Leu Glu Lys Arg Ile Ser Ala Asn
     50                  55                  60

Thr Phe Asn Ser Tyr Met Ser Arg Ala Arg Lys Arg Phe Asp Asp Arg
 65                  70                  75                  80

Leu His His Asn Phe Glu Lys Asn Val Ile Lys Leu Ser Glu Lys Tyr
                     85                  90                  95

Pro Leu Tyr Ser Glu Glu Leu Ser Ser Trp Leu Ser Met Pro Ala Ala
                100                 105                 110

Ser Ile Arg Gln His Met Ser Arg Leu Gln Ala Lys Leu Lys Glu Ile
                115                 120                 125

Met Pro Leu Ala Glu Asp Leu Ser Asn Ile Lys Ile Gly Thr Lys Asn
130                 135                 140

Ser Glu Ala Lys Ile Asn Lys Leu Ala Asn Lys Tyr Pro Glu Trp Gln
145                 150                 155                 160

Phe Ala Ile Ser Asp Leu Asn Ser Glu Asp Trp Lys Asp Lys Arg Asp
                165                 170                 175

Tyr Leu Tyr Lys Leu Phe Gln Gln Gly Ser Ser Leu Leu Glu Asp Leu
                180                 185                 190

Asn Asn Leu Lys Val Asn His Glu Val Leu Tyr His Leu Gln Leu Ser
                195                 200                 205

Ser Ala Glu Arg Thr Ser Ile Gln Gln Arg Trp Ala Asn Val Leu Ser
210                 215                 220

Glu Lys Lys Arg Asn Val Val Ile Asp Tyr Pro Arg Tyr Met Gln
225                 230                 235                 240

Ala Ile Tyr Asp Ile Ile Asn Lys Pro Ile Val Ser Phe Asp Leu Thr
                245                 250                 255

Thr Arg Arg Gly Met Ala Pro Leu Ala Phe Ala Leu Ala Ala Leu Ser
                260                 265                 270

Gly Arg Arg Met Ile Glu Ile Met Leu Gln Gly Glu Phe Ser Val Ala
                275                 280                 285

Gly Lys Tyr Thr Val Thr Phe Leu Gly Gln Ala Lys Lys Arg Ser Glu
                290                 295                 300

Asp Lys Gly Ile Ser Arg Lys Ile Tyr Thr Leu Cys Asp Ala Thr Leu
305                 310                 315                 320

Phe Val Ser Leu Val Asn Glu Leu Arg Ser Cys Pro Ala Ala Ala Asp
                325                 330                 335

Phe Asp Glu Val Ile Lys Gly Tyr Gly Glu Asn Asp Thr Arg Ser Glu
                340                 345                 350

Asn Gly Arg Ile Asn Ala Ile Leu Ala Thr Ala Phe Asn Pro Trp Val
                355                 360                 365

Lys Thr Phe Leu Gly Asp Arg Arg Val Tyr Lys Asp Ser Arg Ala
370                 375                 380

Ile Tyr Ala Arg Ile Ala Tyr Glu Met Phe Arg Val Asp Pro Arg
385                 390                 395                 400

Trp Lys Asn Val Asp Glu Val Phe Phe Met Glu Ile Leu Gly His
                405                 410                 415

Asp Asp Glu Asn Thr Gln Leu His Tyr Lys Gln Phe Lys Leu Ala Asn
                420                 425                 430

Phe Ser Arg Thr Trp Arg Pro Asn Val Gly Glu Glu Asn Ala Arg Leu
                435                 440                 445

Ala Ala Leu Gln Lys Leu Asp Ser Met Met Pro Asp Phe Ala Arg Gly
450                 455                 460
```

```
Asp Ala Gly Val Arg Ile His Glu Thr Val Lys Gln Leu Val Glu Gln
465                 470                 475                 480

Asp Pro Ser Ile Lys Ile Thr Asn Ser Thr Leu Arg Pro Phe Asn Phe
            485                 490                 495

Ser Thr Arg Leu Ile Pro Arg Tyr Leu Glu Phe Ala Ala Asp Ala Leu
            500                 505                 510

Gly Gln Phe Val Gly Glu Asn Gly Gln Trp Gln Leu Lys Asp Glu Ala
        515                 520                 525

Pro Ala Ile Val Leu Pro Asp Glu Ile Leu Glu Pro Met Asp Asp
    530                 535                 540

Val Asp Leu Asp Asp Glu Asn His Asp Asp Glu Thr Leu Asp Asp Asp
545                 550                 555                 560

Glu Ile Glu Val Asp Glu Ser Glu Gly Glu Glu Leu Glu Glu Ala Gly
                565                 570                 575

Asp Ala Glu Glu Ala Glu Val Ala Glu Gln Glu Glu Lys His Pro Gly
            580                 585                 590

Lys Pro Asn Phe Lys Ala Pro Arg Asp Asn Gly Asp Gly Thr Tyr Met
        595                 600                 605

Val Glu Phe Glu Phe Gly Gly Arg His Tyr Ala Trp Ser Gly Ala Ala
    610                 615                 620

Gly Asn Arg Val Glu Ala Met Gln Ser Ala Trp Ser Ala Tyr Phe Lys
625                 630                 635                 640
```

<210> SEQ ID NO 7
<211> LENGTH: 1617
<212> TYPE: DNA
<213> ORGANISM: Vibrio sp. phage VP882
<220> FEATURE:
<221> NAME/KEY: misc_feature
<223> OTHER INFORMATION: Protelomerase

<400> SEQUENCE: 7

```
atgagcggcg aaagtagaca aaaggtaaac ctcgaggagt taataaatga gctcgtcgag      60
gaggtgaaaa ccatcgatga caatgaggcg attactcggt ctgaaaaaac caagttgatc     120
accagggcgg cgactaaatt caagaccaag ctgcacgacg ataagcgccg gaaggatgcg     180
accagaatcg ctctgagcac ctatcgtaag tacatgacaa tggccagggc agcagttact     240
gagcagaact ggaaacacca cagtctcgag cagcagatag agcggctggc caaaaagcac     300
ccgcaatacg ctgagcagct ggtggccatc ggggccatgg ataacatcac cgagttgcgc     360
ctggcgcatc gcgacctcct gaagagcatc aaggacaacg atgaagcctt cgaggatatc     420
cgcagcatga agttagacca cgaggtaatg cgccatctga cgctacccag tgcgcaaaag     480
gcgagactgg cagaggaagc cgccgaggcg ttgaccgaga gaaaaccgc cacggtcgac     540
atcaactatc acgagctgat ggccggcgtg gtggagctgt tgaccaagaa gaccaagacg     600
gtcggcagcg acagcaccta cagcttcagc cggctggcgc ttggtattgg cctggctacc     660
ggtcgtcgtt ctatcgagat actgaagcag gcgagttca aaaaggtgga tgagcagcgg     720
ctcgagttct ctggccaagc gaaaaagcgc ggcggtgccg actattcaga gacctatacc     780
atttacaccc tggtcgactc cgacctggta ctgatggcgc tgaagaacct gcgagagttg     840
ccagaagttc gcgcactgga tgagtacgac caactgggcg agattaagcg gaacgacgcc     900
atcaataaac gctgtgcaaa aacgctcaac caaaccgcca agcagttctt ggcagcgac     960
gagcgcgtgt tcaaagatag tcgtgccatc tgggcgcgtc tggcttatga gttgttttt    1020
caacgtgatc cgcgctggaa aaagaaagac gaggacgttt tctggcagga gatgctgggc    1080
```

-continued

```
cacgaggaca tcgagactca gaaagcctat aagcaattca aggtcgacta cagcgaacct   1140
gagcagccgg tgcacaagcc tggcaaattt aagagcagag ctgaagccct cgcggcgctc   1200
gactcaaatg aggacattac cacccgctca tccatggcca agatccacga ctgggtgaaa   1260
gagcgtattg cggaagaccc cgaggcgaac atcacacagt cactcatcac ccgggaactg   1320
ggctcaggcc gtaaggtgat caaggactac ctcgacctgg ctgacgatgc ccttgctgtg   1380
gtgaatactc ctgtcgatga cgcagtcgtc gaggttccag ctgatgtgcc ggcagcagaa   1440
aaacagccga gaaagcgca gaagcccaga ctcgtggctc accaggttga tgatgagcac   1500
tgggaagcct gggcgctggt ggaaggcgag gaggtggcca gggtgaaaat caagggcacc   1560
cgcgttgagg caatgacagc cgcatgggag gccagccaaa aggcactcga tgactaa     1617
```

<210> SEQ ID NO 8
<211> LENGTH: 538
<212> TYPE: PRT
<213> ORGANISM: Vibrio sp. phage VP882
<220> FEATURE:
<221> NAME/KEY: MISC_FEATURE
<223> OTHER INFORMATION: Protelomerase

<400> SEQUENCE: 8

```
Met Ser Gly Glu Ser Arg Gln Lys Val Asn Leu Glu Glu Leu Ile Asn
1               5                   10                  15

Glu Leu Val Glu Val Lys Thr Ile Asp Asp Asn Glu Ala Ile Thr
            20                  25                  30

Arg Ser Glu Lys Thr Lys Leu Ile Thr Arg Ala Ala Thr Lys Phe Lys
        35                  40                  45

Thr Lys Leu His Asp Asp Lys Arg Arg Lys Asp Ala Thr Arg Ile Ala
    50                  55                  60

Leu Ser Thr Tyr Arg Lys Tyr Met Thr Met Ala Arg Ala Val Thr
65                  70                  75                  80

Glu Gln Asn Trp Lys His His Ser Leu Glu Gln Gln Ile Glu Arg Leu
                85                  90                  95

Ala Lys Lys His Pro Gln Tyr Ala Glu Gln Leu Val Ala Ile Gly Ala
            100                 105                 110

Met Asp Asn Ile Thr Glu Leu Arg Leu Ala His Arg Asp Leu Leu Lys
        115                 120                 125

Ser Ile Lys Asp Asn Asp Glu Ala Phe Glu Asp Ile Arg Ser Met Lys
    130                 135                 140

Leu Asp His Glu Val Met Arg His Leu Thr Leu Pro Ser Ala Gln Lys
145                 150                 155                 160

Ala Arg Leu Ala Glu Glu Ala Ala Glu Ala Leu Thr Glu Lys Lys Thr
                165                 170                 175

Ala Thr Val Asp Ile Asn Tyr His Glu Leu Met Ala Gly Val Val Glu
            180                 185                 190

Leu Leu Thr Lys Lys Thr Lys Thr Val Gly Ser Asp Ser Thr Tyr Ser
        195                 200                 205

Phe Ser Arg Leu Ala Leu Gly Ile Gly Leu Ala Thr Gly Arg Arg Ser
    210                 215                 220

Ile Glu Ile Leu Lys Gln Gly Glu Phe Lys Lys Val Asp Glu Gln Arg
225                 230                 235                 240

Leu Glu Phe Ser Gly Gln Ala Lys Lys Arg Gly Gly Ala Asp Tyr Ser
                245                 250                 255

Glu Thr Tyr Thr Ile Tyr Thr Leu Val Asp Ser Asp Leu Val Leu Met
```

```
                260             265             270
Ala Leu Lys Asn Leu Arg Glu Leu Pro Glu Val Arg Ala Leu Asp Glu
            275             280             285

Tyr Asp Gln Leu Gly Glu Ile Lys Arg Asn Asp Ala Ile Asn Lys Arg
        290             295             300

Cys Ala Lys Thr Leu Asn Gln Thr Ala Lys Gln Phe Phe Gly Ser Asp
305             310             315             320

Glu Arg Val Phe Lys Asp Ser Arg Ala Ile Trp Ala Arg Leu Ala Tyr
                325             330             335

Glu Leu Phe Phe Gln Arg Asp Pro Arg Trp Lys Lys Asp Glu Asp
            340             345             350

Val Phe Trp Gln Glu Met Leu Gly His Glu Asp Ile Glu Thr Gln Lys
        355             360             365

Ala Tyr Lys Gln Phe Lys Val Asp Tyr Ser Glu Pro Glu Gln Pro Val
    370             375             380

His Lys Pro Gly Lys Phe Lys Ser Arg Ala Glu Ala Leu Ala Ala Leu
385             390             395             400

Asp Ser Asn Glu Asp Ile Thr Thr Arg Ser Ser Met Ala Lys Ile His
                405             410             415

Asp Trp Val Lys Glu Arg Ile Ala Glu Asp Pro Glu Ala Asn Ile Thr
            420             425             430

Gln Ser Leu Ile Thr Arg Glu Leu Gly Ser Gly Arg Lys Val Ile Lys
        435             440             445

Asp Tyr Leu Asp Leu Ala Asp Asp Ala Leu Ala Val Val Asn Thr Pro
    450             455             460

Val Asp Asp Ala Val Val Glu Val Pro Ala Asp Val Pro Ala Ala Glu
465             470             475             480

Lys Gln Pro Lys Lys Ala Gln Lys Pro Arg Leu Val Ala His Gln Val
                485             490             495

Asp Asp Glu His Trp Glu Ala Trp Ala Leu Val Glu Gly Glu Gly Val
            500             505             510

Ala Arg Val Lys Ile Lys Gly Thr Arg Val Glu Ala Met Thr Ala Ala
        515             520             525

Trp Glu Ala Ser Gln Lys Ala Leu Asp Asp
    530             535
```

<210> SEQ ID NO 9
<211> LENGTH: 4055
<212> TYPE: DNA
<213> ORGANISM: Escherichia coli bacteriophage N15
<220> FEATURE:
<221> NAME/KEY: misc_feature
<223> OTHER INFORMATION: Protelomerase TelN

<400> SEQUENCE: 9

```
catatgcact atatcatatc tcaattacgg aacatatcag cacacaattg cccattatac      60
gcgcgtataa tggactattg tgtgctgata aggagaacat aagcgcagaa caatatgtat     120
ctattccggt gttgtgttcc tttgttattc tgctattatg ttctcttata gtgtgacgaa     180
agcagcataa ttaatcgtca cttgttcttt gattgtgtta cgatatccag agacttagaa     240
acgggggaac cggatgagc aaggtaaaaa tcggtgagtt gatcaacacg cttgtgaatg     300
aggtagaggc aattgatgcc tcagaccgcc acaaggcga caaaacgaag agaattaaag     360
ccgcagccgc acgtataag aacgcgttat ttaatgataa agaaagttc cgtgggaaag     420 gattgcagaa aagaataacc gcgaatactt ttaacgccta tgagcagg gcaagaaagc     480
```

```
ggtttgatga taaattacat catagctttg ataaaaatat taataaatta tcggaaaagt    540
atcctcttta cagcgaagaa ttatcttcat ggctttctat gcctacggct aatattcgcc    600
agcacatgtc atcgttacaa tctaaattga agaaataat  gccgcttgcc gaagagttat    660
caaatgtaag aataggctct aaaggcagtg atgcaaaaat agcaagacta ataaaaaaat    720
atccagattg gagttttgct cttagtgatt taaacagtga tgattggaag gagcgccgtg    780
actatcttta taagttattc caacaaggct ctgcgttgtt agaagaacta caccagctca    840
aggtcaacca tgaggttctg taccatctgc agctaagccc tgcggagcgt acatctatac    900
agcaacgatg ggccgatgtt ctgcgcgaga agaagcgtaa tgttgtggtt attgactacc    960
caacatacat gcagtctatc tatgatattt tgaataatcc tgcgacttta tttagtttaa   1020
acactcgttc tggaatggca cctttggcct ttgctctggc tgcggtatca gggcgaagaa   1080
tgattgagat aatgtttcag ggtgaatttg ccgtttcagg aaagtatacg gttaatttct   1140
cagggcaagc taaaaaacgc tctgaagata aagcgtaac  cagaacgatt tatactttat   1200
gcgaagcaaa attattcgtt gaattattaa cagaattgcg ttcttgctct gctgcatctg   1260
atttcgatga ggttgttaaa ggatatgaaa aggatgatac aaggtctgag aacggcagga   1320
taaatgctat tttagcaaaa gcatttaacc cttgggttaa atcatttttc ggcgatgacc   1380
gtcgtgttta taaagatagc cgcgctattt acgctcgcat cgcttatgag atgttcttcc   1440
gcgtcgatcc acggtggaaa aacgtcgacg aggatgtgtt cttcatggag attctcggac   1500
acgacgatga gaacacccag ctgcactata agcagttcaa gctggccaac ttctccagaa   1560
cctggcgacc tgaagttggg gatgaaaaca ccaggctggt ggctctgcag aaactggacg   1620
atgaaatgcc aggctttgcc agaggtgacg ctggcgtccg tctccatgaa accgttaagc   1680
agctggtgga gcaggaccca tcagcaaaaa taaccaacag cactctccgg gcctttaaat   1740
ttagcccgac gatgattagc cggtacctgg agtttgccgc tgatgcattg gggcagttcg   1800
ttggcgagaa cgggcagtgg cagctgaaga tagagacacc tgcaatcgtc ctgcctgatg   1860
aagaatccgt tgagaccatc gacgaaccgg atgatgagtc caagacgac  gagctggatg   1920 aagatgaaat tgagctcgac gagggtggcg gcgatgaacc aaccgaagag gaagggccag   1980
aagaacatca gccaactgct ctaaaacccg tcttcaagcc tgcaaaaaat aacggggacg   2040
gaacgtacaa gatagagttt gaatacgatg gaaagcatta tgcctggtcc ggccccgccg   2100
atagccctat ggccgcaatg cgatccgcat gggaaacgta ctacagctaa aagaaaagcc   2160
accggtgtta atcggtggct tttttattga ggcctgtccc tacccatccc ctgcaaggga   2220
cggaaggatt aggcggaaac tgcagctgca actacggaca tcgccgtccc gactgcaggg   2280
acttccccgc gtaaagcggg gcttaaattc gggctggcca accctatttt tctgcaatcg   2340
ctggcgatgt tagtttcgtg gatagcgttt ccagcttttc aatggccagc tcaaaatgtg   2400
ctggcagcac cttctccagt tccgtatcaa tatcggtgat cggcagctct ccacaagaca   2460
tactccggcg accgccacga actacatcgc gcagcagctc ccgttcgtag acacgcatgt   2520
tgcccagagc cgtttctgca gccgttaata tccggcgcac gtcggcgatg attgccggga   2580
gatcatccac ggttattggg ttcggtgatg ggttcctgca ggcgcggcgg agagccatcc   2640
agacgccgct aacccatgcg ttacggtact gaaaactttg tgctatgtcg tttatcaggc   2700
ccgaagttct tctttctgcc gccagtccag tggttcaccg gcgttcttag gctcaggctc   2760
gacaaaagca tactcgccgt ttttccggat agctggcaga acctcgttcg tcacccactt   2820
```

```
gcggaaccgc caggctgtcg tcccctgttt caccgcgtcg cggcagcgga ggattatggt    2880
gtagagacca gattccgata ccacatttac ttccctggcc atccgatcaa gttttgtgc     2940 ctcggttaaa ccgagggtca atttttcatc atgatccagc ttacgcaatg catcagaagg   3000
gttggctata ttcaatgcag cacagatatc cagcgccaca aaccacgggt caccaccgac    3060
aagaaccacc cgtatagggt ggctttcctg aaatgaaaag acggagagag ccttcattgc    3120
gcctccccgg atttcagctg ctcagaaagg gacagggagc agccgcgagc ttcctgcgtg   3180
agttcgcgcg cgacctgcag aagttccgca gcttcctgca aatacagcgt ggcctcataa   3240
ctggagatag tgcggtgagc agagcccaca agcgcttcaa cctgcagcag gcgttcctca   3300
atcgtctcca gcaggccctg gcgtttaac tgaatctggt tcatgcgatc acctcgctga    3360
ccgggatacg ggctgacaga acgaggacaa aacggctggc gaactggcga cgagcttctc   3420
gctcggatga tgcaatggtg gaaaggcggt ggatatggga tttttttgtcc gtgcggacga  3480 cagctgcaaa tttgaatttg aacatggtat gcattcctat cttgtatagg gtgctaccac   3540
cagagttgag aatctctata ggggtggtag cccagacagg gttctcaaca ccggtacaag    3600
aagaaaccgg cccaaccgaa gttggcccca tctgagccac cataattcag gtatgcgcag   3660
atttaacaca caaaaaaaca cgctggcgcg tgttgtgcgc ttcttgtcat cggggttga    3720 gaggcccggc tgcagatttt gctgcagcgg ggtaactcta ccgccaaagc agaacgcacg   3780
tcaataattt aggtggatat tttacccccgt gaccagtcac gtgcacaggt gttttttatag 3840 tttgctttac tgactgatca gaacctgatc agttattgga gtccggtaat cttattgatg    3900
accgcagcca ccttagatgt tgtctcaaac cccatacggc cacgaatgag ccactggaac    3960
ggaatagtca gcaggtacag cggaacgaac cacaaacggt tcagacgctg ccagaacgtc    4020
gcatcacgac gttccatcca ttcggtattg tcgac                             4055
```

<210> SEQ ID NO 10
<211> LENGTH: 631
<212> TYPE: PRT
<213> ORGANISM: Escherichia coli bacteriophage N15
<220> FEATURE:
<221> NAME/KEY: misc_feature
<223> OTHER INFORMATION: Protelomerase sequence Tel N

<400> SEQUENCE: 10

```
Met Ser Lys Val Lys Ile Gly Glu Leu Ile Asn Thr Leu Val Asn Glu
1               5                   10                  15

Val Glu Ala Ile Asp Ala Ser Asp Arg Pro Gln Gly Asp Lys Thr Lys
            20                  25                  30

Arg Ile Lys Ala Ala Ala Ala Arg Tyr Lys Asn Ala Leu Phe Asn Asp
        35                  40                  45

Lys Arg Lys Phe Arg Gly Lys Gly Leu Gln Lys Arg Ile Thr Ala Asn
    50                  55                  60

Thr Phe Asn Ala Tyr Met Ser Arg Ala Arg Lys Arg Phe Asp Asp Lys
65                  70                  75                  80

Leu His His Ser Phe Asp Lys Asn Ile Asn Lys Leu Ser Glu Lys Tyr
                85                  90                  95

Pro Leu Tyr Ser Glu Glu Leu Ser Ser Trp Leu Ser Met Pro Thr Ala
            100                 105                 110

Asn Ile Arg Gln His Met Ser Ser Leu Gln Ser Lys Leu Lys Glu Ile
        115                 120                 125

Met Pro Leu Ala Glu Glu Leu Ser Asn Val Arg Ile Gly Ser Lys Gly
    130                 135                 140
```

```
Ser Asp Ala Lys Ile Ala Arg Leu Ile Lys Lys Tyr Pro Asp Trp Ser
145                 150                 155                 160

Phe Ala Leu Ser Asp Leu Asn Ser Asp Asp Trp Lys Glu Arg Arg Asp
            165                 170                 175

Tyr Leu Tyr Lys Leu Phe Gln Gln Gly Ser Ala Leu Leu Glu Glu Leu
        180                 185                 190

His Gln Leu Lys Val Asn His Glu Val Leu Tyr His Leu Gln Leu Ser
    195                 200                 205

Pro Ala Glu Arg Thr Ser Ile Gln Gln Arg Trp Ala Asp Val Leu Arg
210                 215                 220

Glu Lys Lys Arg Asn Val Val Ile Asp Tyr Pro Thr Tyr Met Gln
225                 230                 235                 240

Ser Ile Tyr Asp Ile Leu Asn Asn Pro Ala Thr Leu Phe Ser Leu Asn
            245                 250                 255

Thr Arg Ser Gly Met Ala Pro Leu Ala Phe Ala Leu Ala Ala Val Ser
        260                 265                 270

Gly Arg Arg Met Ile Glu Ile Met Phe Gln Gly Phe Ala Val Ser
    275                 280                 285

Gly Lys Tyr Thr Val Asn Phe Ser Gly Gln Ala Lys Lys Arg Ser Glu
290                 295                 300

Asp Lys Ser Val Thr Arg Thr Ile Tyr Thr Leu Cys Glu Ala Lys Leu
305                 310                 315                 320

Phe Val Glu Leu Leu Thr Glu Leu Arg Ser Cys Ser Ala Ala Ser Asp
            325                 330                 335

Phe Asp Glu Val Val Lys Gly Tyr Gly Lys Asp Thr Arg Ser Glu
        340                 345                 350

Asn Gly Arg Ile Asn Ala Ile Leu Ala Lys Ala Phe Asn Pro Trp Val
    355                 360                 365

Lys Ser Phe Phe Gly Asp Asp Arg Arg Val Tyr Lys Asp Ser Arg Ala
370                 375                 380

Ile Tyr Ala Arg Ile Ala Tyr Glu Met Phe Phe Arg Val Asp Pro Arg
385                 390                 395                 400

Trp Lys Asn Val Asp Glu Asp Val Phe Phe Met Glu Ile Leu Gly His
            405                 410                 415

Asp Asp Glu Asn Thr Gln Leu His Tyr Lys Gln Phe Lys Leu Ala Asn
        420                 425                 430

Phe Ser Arg Thr Trp Arg Pro Glu Val Gly Asp Glu Asn Thr Arg Leu
    435                 440                 445

Val Ala Leu Gln Lys Leu Asp Asp Glu Met Pro Gly Phe Ala Arg Gly
450                 455                 460

Asp Ala Gly Val Arg Leu His Glu Thr Val Lys Gln Leu Val Glu Gln
465                 470                 475                 480

Asp Pro Ser Ala Lys Ile Thr Asn Ser Thr Leu Arg Ala Phe Lys Phe
            485                 490                 495

Ser Pro Thr Met Ile Ser Arg Tyr Leu Glu Phe Ala Ala Asp Ala Leu
        500                 505                 510

Gly Gln Phe Val Gly Glu Asn Gly Gln Trp Gln Leu Lys Ile Glu Thr
    515                 520                 525

Pro Ala Ile Val Leu Pro Asp Glu Glu Ser Val Glu Thr Ile Asp Glu
530                 535                 540

Pro Asp Asp Glu Ser Gln Asp Asp Glu Leu Asp Glu Asp Glu Ile Glu
545                 550                 555                 560
```

-continued

Leu Asp Glu Gly Gly Asp Glu Pro Thr Glu Glu Gly Pro Glu
            565                 570                 575

Glu His Gln Pro Thr Ala Leu Lys Pro Val Phe Lys Pro Ala Lys Asn
        580                 585                 590

Asn Gly Asp Gly Thr Tyr Lys Ile Glu Phe Glu Tyr Asp Gly Lys His
    595                 600                 605

Tyr Ala Trp Ser Gly Pro Ala Asp Ser Pro Met Ala Ala Met Arg Ser
610                 615                 620

Ala Trp Glu Thr Tyr Tyr Ser
625                 630

<210> SEQ ID NO 11
<211> LENGTH: 1329
<212> TYPE: DNA
<213> ORGANISM: Agrobacterium tumefaciens strain C58
<220> FEATURE:
<221> NAME/KEY: misc_feature
<223> OTHER INFORMATION: Protelomerase TelA

<400> SEQUENCE: 11

| | | |
|---|---|---|
| atgctcgccg caaaacgaaa acaaaaaca ccggtcctcg tggaacgcat cgatcaattc | 60 |
| gtcggccaga tcaagaggc gatgaaaagc gacgacgctt cgcgaaacag gaaaatccgc | 120 |
| gatctgtggg atgccgaggt ccgctatcat ttcgataatg ccgcacggca aaagacgctc | 180 |
| gaactttaca tcatgaaata tcgcaatgcg ctgaaggccg aattcggccc gaagagcacc | 240 |
| ccgctagcca tctgcaacat gaagaagctg cgcgagcgcc tgaacaccta tattgcccgg | 300 |
| ggcgattatc ccaagacagg cgtggcgacg tcgattgtcg aaaaaatcga gcgggcggag | 360 |
| ttcaacaccg ccggccgcaa acccacggtt ctccttcgca tagccgattt cattgccgcg | 420 |
| atgaacggca tggacgcgaa gcaggacatg caggctctgt gggacgcaga atcgccatc | 480 |
| atgaacggcc gcgcccagac gacgatcatt tcctacatca ccaaatatcg caacgccatc | 540 |
| cgggaagcct tcggtgacga ccatccgatg ctgaagatcg ccaccggcga tgccgcgatg | 600 |
| tatgacgagg cccgccgggt gaagatggag aagatcgcca acaagcatgg cgcgctcatc | 660 |
| acattcgaga actaccggca ggttctgaaa atctgcgagg attgtctcaa gtccagcgat | 720 |
| cccctgatga tcggcatcgg cctcatcggc atgacgggac gccgacccta tgaagtcttc | 780 |
| acccaggcgg aattttcacc tgcaccctat ggcaagggag tttccaaatg gagcatcctg | 840 |
| ttcaacggtc aggccaagac gaaacagggc gagggcacga aattcgggat tacctatgaa | 900 |
| attcctgtcc tgacgcgctc cgaaaccgtg ctggctgcct ataagcgcct gcgcgaaagc | 960 |
| ggacagggaa aattatggca tggcatgtcg atcgacgatt tttcctcgga aacccgcctg | 1020 |
| ctgctgcgcg acacggtttt taacctgttc gaggatgtct ggccaaagga agagcttccc | 1080 |
| aagccctatg gcctcagaca cctctatgcc gaagtggcct atcacaattt cgcgccaccc | 1140 |
| catgtcacca gaacagcta tttcgccgcc attcttggcc acaacaataa cgacctcgaa | 1200 |
| acgtcgctgt cctatatgac ctatacgctg ccggaagacc gcgacaatgc gctggcgcgc | 1260 |
| ctgaagcgga ccaatgagcg gacattgcag caaatggcga cgatcgcgcc cgtgtcccgc | 1320 |
| aagggatga | 1329 |

<210> SEQ ID NO 12
<211> LENGTH: 442
<212> TYPE: PRT
<213> ORGANISM: Agrobacterium tumefaciens strain C58
<220> FEATURE:
<221> NAME/KEY: MISC_FEATURE
<223> OTHER INFORMATION: Protelomerase TelA

<400> SEQUENCE: 12

```
Met Leu Ala Ala Lys Arg Lys Thr Lys Thr Pro Val Leu Val Glu Arg
1               5                  10                  15

Ile Asp Gln Phe Val Gly Gln Ile Lys Glu Ala Met Lys Ser Asp Asp
            20                  25                  30

Ala Ser Arg Asn Arg Lys Ile Arg Asp Leu Trp Asp Ala Glu Val Arg
        35                  40                  45

Tyr His Phe Asp Asn Gly Arg Thr Glu Lys Thr Leu Glu Leu Tyr Ile
    50                  55                  60

Met Lys Tyr Arg Asn Ala Leu Lys Ala Glu Phe Gly Pro Lys Ser Thr
65                  70                  75                  80

Pro Leu Ala Ile Cys Asn Met Lys Lys Leu Arg Glu Arg Leu Asn Thr
                85                  90                  95

Tyr Ile Ala Arg Gly Asp Tyr Pro Lys Thr Gly Val Ala Thr Ser Ile
            100                 105                 110

Val Glu Lys Ile Glu Arg Ala Glu Phe Asn Thr Ala Gly Arg Lys Pro
        115                 120                 125

Thr Val Leu Leu Arg Ile Ala Asp Phe Ile Ala Ala Met Asn Gly Met
130                 135                 140

Asp Ala Lys Gln Asp Met Gln Ala Leu Trp Asp Ala Glu Ile Ala Ile
145                 150                 155                 160

Met Asn Gly Arg Ala Gln Thr Thr Ile Ile Ser Tyr Ile Thr Lys Tyr
                165                 170                 175

Arg Asn Ala Ile Arg Glu Ala Phe Gly Asp Asp His Pro Met Leu Lys
            180                 185                 190

Ile Ala Thr Gly Asp Ala Ala Met Tyr Asp Glu Ala Arg Arg Val Lys
        195                 200                 205

Met Glu Lys Ile Ala Asn Lys His Gly Ala Leu Ile Thr Phe Glu Asn
210                 215                 220

Tyr Arg Gln Val Leu Lys Ile Cys Glu Asp Cys Leu Lys Ser Ser Asp
225                 230                 235                 240

Pro Leu Met Ile Gly Ile Gly Leu Ile Gly Met Thr Gly Arg Arg Pro
                245                 250                 255

Tyr Glu Val Phe Thr Gln Ala Glu Phe Ser Pro Ala Pro Tyr Gly Lys
            260                 265                 270

Gly Val Ser Lys Trp Ser Ile Leu Phe Asn Gly Gln Ala Lys Thr Lys
        275                 280                 285

Gln Gly Glu Gly Thr Lys Phe Gly Ile Thr Tyr Glu Ile Pro Val Leu
290                 295                 300

Thr Arg Ser Glu Thr Val Leu Ala Ala Tyr Lys Arg Leu Arg Glu Ser
305                 310                 315                 320

Gly Gln Gly Lys Leu Trp His Gly Met Ser Ile Asp Asp Phe Ser Ser
                325                 330                 335

Glu Thr Arg Leu Leu Leu Arg Asp Thr Val Phe Asn Leu Phe Glu Asp
            340                 345                 350

Val Trp Pro Lys Glu Glu Leu Pro Lys Pro Tyr Gly Leu Arg His Leu
        355                 360                 365

Tyr Ala Glu Val Ala Tyr His Asn Phe Ala Pro Pro His Val Thr Lys
    370                 375                 380

Asn Ser Tyr Phe Ala Ala Ile Leu Gly His Asn Asn Asp Leu Glu
385                 390                 395                 400
```

Thr Ser Leu Ser Tyr Met Thr Tyr Thr Leu Pro Glu Asp Arg Asp Asn
            405                 410                 415

Ala Leu Ala Arg Leu Lys Arg Thr Asn Glu Arg Thr Leu Gln Gln Met
        420                 425                 430

Ala Thr Ile Ala Pro Val Ser Arg Lys Gly
        435                 440

<210> SEQ ID NO 13
<211> LENGTH: 1668
<212> TYPE: DNA
<213> ORGANISM: Vibrio parahaemolyticus phage Vp58.5 Gp40
<220> FEATURE:
<221> NAME/KEY: misc_feature
<223> OTHER INFORMATION: Protelomerase

<400> SEQUENCE: 13

| | | | | | |
|---|---|---|---|---|---|
| atgaaactaa | ctgacggaat | ggaccgcaca | aagtacatcg | ttaaagcggc | caaacatatc | 60 |
| caagaagaag | gtcaagaaaa | gggacctaaa | tacatcactg | accgctgcgg | tcgtgtcgct | 120 |
| aaggatgagc | acaaacgtct | tggctgggtt | gtggaccagt | tgtcaggtga | gctgccagc | 180 |
| aatccacaaa | tcagccataa | ccactatatc | aatcttatga | ataattaccg | tagagccatc | 240 |
| aaggccctag | gtataagca | tcaccaaata | gaaaagacat | tagtaacttt | tatcaataaa | 300 |
| tatcaagaat | atagacctga | aatagcagag | atgctggacc | catctttgcc | aattgatacc | 360 |
| ttgagagaga | atgtgatcct | tctgaaatca | caggccaggt | caaaaagtga | atttcgtagt | 420 |
| gacctgcttg | gtcttcgcat | tgagtttcac | ctctactatc | tgtttgaacc | aaagggcatt | 480 |
| gcaaccgata | agcgcaaaga | gcaagtaaaa | gaagcgttga | tgaaaagca | tgagaacgtc | 540 |
| atcaagataa | atggcgatca | catcaaggaa | ctggccacaa | aaattctgtc | agaaaaggac | 600 |
| ccgtcatata | cagaccttgc | agttggcctt | gctcttgcga | ctggccgtcg | agctaatgag | 660 |
| attatgaaga | ctgccagctt | taagaaatca | ggtgaacggt | cgcttatgtt | tgagggacag | 720 |
| ctaaaaaccc | ataaccgata | cctgtttgaa | gaaattggag | catacgagat | accttgtatt | 780 |
| gttgattcag | acttagtaat | taaaggattg | aaattattaa | gaaaaaaaac | aggagcggaa | 840 |
| atcctggaat | atactgatgt | cactggacgt | acagttaaaa | aggctgttgc | tgacggcgac | 900 |
| actaaggacc | tgagacacaa | tgatgcagtc | aaccttcggt | tcactgcatc | acttaaccag | 960 |
| agagtcaagg | ccatactagg | ccatggagag | tttagtttca | ggacctgtcg | ggccatctat | 1020 |
| gtcgaaatag | cattccatga | gttcagacat | aacggagaat | cgaaagcggc | cttccgtagc | 1080 |
| agagttcttg | ccactcagg | tggtgataaa | tcaacacaga | accactatga | ggggtttgag | 1140 |
| cttgattcca | aggtggaaac | catcggtgtg | gttgatatgg | gccaaaacga | ggctgacaag | 1200 |
| tcatacaaca | agcaactgct | gaagcacctg | gagcaatacg | atgcaacaat | tgcagcctat | 1260 |
| ctgagagcgc | ctaactggaa | acacattcat | gattggctaa | aagaccaggt | gaaaaacggc | 1320 |
| ctgcagcttg | accaaataac | cacaagctat | ctgagaaaaa | tgtgcatcat | caacaacaaa | 1380 |
| agcctcaatg | caaacaccat | cgccaagtac | ctggaaacat | tgaacctaga | taaggttcca | 1440 |
| gcagagcaag | aggaaagcca | tcaggaagaa | ctggagcagg | aagaagatca | gaaagtgtca | 1500 |
| tggccaaaag | ctaaagacat | taaggtccag | tctaaaaaag | aaggtgatat | gtggcatgtc | 1560 |
| tggactgagg | ttaacggaat | gcggtgggaa | aattggtcta | aaggtagaaa | aacagaagct | 1620 |
| gtgaaggcat | tgcgacaaca | atatgagagg | gaatcagcgg | aaatgtaa | | 1668 |

<210> SEQ ID NO 14
<211> LENGTH: 555

<212> TYPE: PRT
<213> ORGANISM: Vibrio parahaemolyticus phage Vp58.5 Gp40
<220> FEATURE:
<221> NAME/KEY: MISC_FEATURE
<223> OTHER INFORMATION: Protelomerase

<400> SEQUENCE: 14

```
Met Lys Leu Thr Asp Gly Met Asp Arg Thr Lys Tyr Ile Val Lys Ala
1               5                   10                  15

Ala Lys His Ile Gln Glu Gly Gln Glu Lys Gly Pro Lys Tyr Ile
            20                  25                  30

Thr Asp Arg Cys Gly Arg Val Ala Lys Asp Glu His Lys Arg Leu Gly
            35                  40                  45

Trp Val Val Asp Gln Val Ser Gly Glu Leu Ala Ser Asn Pro Gln Ile
50                  55                  60

Ser His Asn His Tyr Ile Asn Leu Met Asn Asn Tyr Arg Arg Ala Ile
65                  70                  75                  80

Lys Ala Leu Gly Tyr Lys His His Gln Ile Glu Lys Thr Leu Val Thr
                85                  90                  95

Phe Ile Asn Lys Tyr Gln Glu Tyr Arg Pro Glu Ile Ala Glu Met Leu
            100                 105                 110

Asp Pro Ser Leu Pro Ile Asp Thr Leu Arg Glu Asn Val Ile Leu Leu
        115                 120                 125

Lys Ser Gln Ala Arg Ser Lys Ser Glu Phe Arg Ser Asp Leu Leu Gly
130                 135                 140

Leu Arg Ile Glu Phe His Leu Tyr Tyr Leu Phe Glu Pro Lys Gly Ile
145                 150                 155                 160

Ala Thr Asp Lys Arg Lys Glu Gln Val Lys Glu Ala Leu Asn Glu Lys
                165                 170                 175

His Glu Asn Val Ile Lys Ile Asn Gly Asp His Ile Lys Glu Leu Ala
            180                 185                 190

Thr Lys Ile Leu Ser Glu Lys Asp Pro Ser Tyr Thr Asp Leu Ala Val
        195                 200                 205

Gly Leu Ala Leu Ala Thr Gly Arg Arg Ala Asn Glu Ile Met Lys Thr
210                 215                 220

Ala Ser Phe Lys Lys Ser Gly Glu Arg Ser Leu Met Phe Glu Gly Gln
225                 230                 235                 240

Leu Lys Thr His Asn Arg Tyr Leu Phe Glu Glu Ile Gly Ala Tyr Glu
                245                 250                 255

Ile Pro Cys Ile Val Asp Ser Asp Leu Val Ile Lys Gly Leu Lys Leu
            260                 265                 270

Leu Arg Lys Lys Thr Gly Ala Glu Ile Leu Glu Tyr Thr Asp Val Thr
        275                 280                 285

Gly Arg Thr Val Lys Lys Val Ala Asp Gly Asp Thr Lys Asp Leu
290                 295                 300

Arg His Asn Asp Ala Val Asn Leu Arg Phe Thr Ala Ser Leu Asn Gln
305                 310                 315                 320

Arg Val Lys Ala Ile Leu Gly His Gly Glu Phe Ser Phe Arg Thr Cys
                325                 330                 335

Arg Ala Ile Tyr Val Glu Ile Ala Phe His Glu Phe Arg His Asn Gly
            340                 345                 350

Glu Ser Lys Ala Ala Phe Arg Ser Arg Val Leu Gly His Ser Gly Gly
        355                 360                 365

Asp Lys Ser Thr Gln Asn His Tyr Glu Gly Phe Glu Leu Asp Ser Lys
370                 375                 380
```

```
Val Glu Thr Ile Gly Val Asp Met Gly Gln Asn Glu Ala Asp Lys
385                 390                 395                 400

Ser Tyr Asn Lys Gln Leu Leu Lys His Leu Glu Gln Tyr Asp Ala Thr
            405                 410                 415

Ile Ala Ala Tyr Leu Arg Ala Pro Asn Trp Lys His Ile His Asp Trp
        420                 425                 430

Leu Lys Asp Gln Val Lys Asn Gly Leu Gln Leu Asp Gln Ile Thr Thr
    435                 440                 445

Ser Tyr Leu Arg Lys Met Cys Ile Ile Asn Asn Lys Ser Leu Asn Ala
450                 455                 460

Asn Thr Ile Ala Lys Tyr Leu Glu Thr Leu Asn Leu Asp Lys Val Pro
465                 470                 475                 480

Ala Glu Gln Glu Glu Ser His Gln Glu Glu Leu Glu Gln Glu Asp
                485                 490                 495

Gln Lys Val Ser Trp Pro Lys Ala Lys Asp Ile Lys Val Gln Ser Lys
            500                 505                 510

Lys Glu Gly Asp Met Trp His Val Trp Thr Glu Val Asn Gly Met Arg
        515                 520                 525

Trp Glu Asn Trp Ser Lys Gly Arg Lys Thr Glu Ala Val Lys Ala Leu
    530                 535                 540

Arg Gln Gln Tyr Glu Arg Glu Ser Ala Glu Met
545                 550                 555

<210> SEQ ID NO 15
<211> LENGTH: 56
<212> TYPE: DNA
<213> ORGANISM: Escherichia coli phage N15
<220> FEATURE:
<221> NAME/KEY: misc_feature
<223> OTHER INFORMATION: protelomerase target sequence

<400> SEQUENCE: 15
tatcagcaca caattgccca ttatacgcgc gtataatgga ctattgtgtg ctgata        56

<210> SEQ ID NO 16
<211> LENGTH: 50
<212> TYPE: DNA
<213> ORGANISM: Klebsiella phage phiK02
<220> FEATURE:
<221> NAME/KEY: misc_feature
<223> OTHER INFORMATION: protelomerase target sequence

<400> SEQUENCE: 16
cagcacacaa cagcccatta tacgcgcgta taatgggcta ttatgtgctg        50

<210> SEQ ID NO 17
<211> LENGTH: 52
<212> TYPE: DNA
<213> ORGANISM: Yersinia enterolytica phage PY54
<220> FEATURE:
<221> NAME/KEY: misc_feature
<223> OTHER INFORMATION: protelomerase target sequence

<400> SEQUENCE: 17
tagtcaccta tttcagcata ctacgcgcgt agtatgctga aataggttac tg        52

<210> SEQ ID NO 18
<211> LENGTH: 90
<212> TYPE: DNA
<213> ORGANISM: Vibrio sp. phage VP882
<220> FEATURE:
```

```
<221> NAME/KEY: misc_feature
<223> OTHER INFORMATION: protelomerase target sequence

<400> SEQUENCE: 18
gggatcccgt tccatacata catgtatcca tgtggcatac tatacgtata gtatgccgat    60
gttacatatg gtatcattcg ggatcccgtt                                     90

<210> SEQ ID NO 19
<211> LENGTH: 38
<212> TYPE: DNA
<213> ORGANISM: Borrelia burgdorferi
<220> FEATURE:
<221> NAME/KEY: misc_feature
<223> OTHER INFORMATION: protelomerase target sequence

<400> SEQUENCE: 19
tactaaataa atattatata tataattttt tattagta                            38

<210> SEQ ID NO 20
<211> LENGTH: 50
<212> TYPE: DNA
<213> ORGANISM: Agrobacterium tumefaciens strain C58
<220> FEATURE:
<221> NAME/KEY: misc_feature
<223> OTHER INFORMATION: protelomerase target sequence

<400> SEQUENCE: 20
gcgatcgatc ataataacaa tatcatgata ttgttattgt aatcgatcgc               50

<210> SEQ ID NO 21
<211> LENGTH: 56
<212> TYPE: DNA
<213> ORGANISM: Vibrio parahaemolyticus phage Vp58.5 Gp40
<220> FEATURE:
<221> NAME/KEY: misc_feature
<223> OTHER INFORMATION: protelomerase target sequence

<400> SEQUENCE: 21
aacctgcaca ggtgtacata tagtctaatt agactatatg tacacctgtg caggtt        56

<210> SEQ ID NO 22
<211> LENGTH: 26
<212> TYPE: DNA
<213> ORGANISM: Agrobacterium tumefaciens strain C58
<220> FEATURE:
<221> NAME/KEY: misc_feature
<223> OTHER INFORMATION: protelomerase target sequence

<400> SEQUENCE: 22
aataacaata tcatgatatt gttatt                                         26

<210> SEQ ID NO 23
<211> LENGTH: 11
<212> TYPE: DNA
<213> ORGANISM: Artificial
<220> FEATURE:
<223> OTHER INFORMATION: Oligonucleotide S1; Example 1

<400> SEQUENCE: 23
gcgtataatg g                                                         11

<210> SEQ ID NO 24
<211> LENGTH: 71
<212> TYPE: DNA
<213> ORGANISM: Artificial
<220> FEATURE:
```

<223> OTHER INFORMATION: PEGS-1; Example 1

<400> SEQUENCE: 24
tatcagcaca caattgccca ttatacgcgc gtataatggg caattgtgtg ctgatatgta    60
cacttaagta g    71

<210> SEQ ID NO 25
<211> LENGTH: 45
<212> TYPE: DNA
<213> ORGANISM: Artificial
<220> FEATURE:
<223> OTHER INFORMATION: PEGS2; Example 1

<400> SEQUENCE: 25
gctatgaact aatgaccccg taattgatta ctacttaagt gtaca    45

<210> SEQ ID NO 26
<211> LENGTH: 45
<212> TYPE: DNA
<213> ORGANISM: Artificial
<220> FEATURE:
<223> OTHER INFORMATION: PEGS3; Example 1

<400> SEQUENCE: 26
aagttatgta acgcggaact ccatatatgg gctatgaact aatga    45

<210> SEQ ID NO 27
<211> LENGTH: 35
<212> TYPE: DNA
<213> ORGANISM: Artificial
<220> FEATURE:
<223> OTHER INFORMATION: PEGS4; Example 1

<400> SEQUENCE: 27
ccaggcgggc catttaccgt aagttatgta acgcg    35

<210> SEQ ID NO 28
<211> LENGTH: 40
<212> TYPE: DNA
<213> ORGANISM: Artificial
<220> FEATURE:
<223> OTHER INFORMATION: PEGS5; Example 1

<400> SEQUENCE: 28
tgggcggggg tcgttgggcg gtcagccagg cgggccattt    40

<210> SEQ ID NO 29
<211> LENGTH: 30
<212> TYPE: DNA
<213> ORGANISM: Artificial
<220> FEATURE:
<223> OTHER INFORMATION: PEGS6; Example 1

<400> SEQUENCE: 29
agtagatctg ctagctgggc gggggtcgtt    30

<210> SEQ ID NO 30
<211> LENGTH: 74
<212> TYPE: DNA
<213> ORGANISM: Artificial
<220> FEATURE:
<223> OTHER INFORMATION: PEGS7; Example 1

<400> SEQUENCE: 30
atagtcgtgt gttaacgggt aatatgcgcg catattaccc gttaacacac gactatacta    60

```
gtagatctgc tagc                                                74
```

<210> SEQ ID NO 31
<211> LENGTH: 79
<212> TYPE: DNA
<213> ORGANISM: Artificial
<220> FEATURE:
<223> OTHER INFORMATION: Oligonucleotide 1.120; Example 2

<400> SEQUENCE: 31

```
tatcagcaca caattgccca ttatacgcgc gtataatgga ctattgtgtg ctgatatgta    60
cacttaagta gtaatcaat                                                79
```

<210> SEQ ID NO 32
<211> LENGTH: 60
<212> TYPE: DNA
<213> ORGANISM: Artificial
<220> FEATURE:
<223> OTHER INFORMATION: Oligonucleotide 1.112; Example 2

<400> SEQUENCE: 32

```
tgggctatga actaatgacc ccgtaattga ttactactta agtgtacata tcagcacaca    60
```

<210> SEQ ID NO 33
<211> LENGTH: 54
<212> TYPE: DNA
<213> ORGANISM: Artificial
<220> FEATURE:
<223> OTHER INFORMATION: Oligonucleotide 1.113; Example 2

<400> SEQUENCE: 33

```
ccgtaagtta tgtaacgcgg aactccatat atgggctatg aactaatgac cccg          54
```

<210> SEQ ID NO 34
<211> LENGTH: 60
<212> TYPE: DNA
<213> ORGANISM: Artificial
<220> FEATURE:
<223> OTHER INFORMATION: Oligonucleotide 1.114; Example 2

<400> SEQUENCE: 34

```
ctagtagatc tgctagccgc caggcgggcc atttaccgta agttatgtaa cgcggaactc    60
```

<210> SEQ ID NO 35
<211> LENGTH: 80
<212> TYPE: DNA
<213> ORGANISM: Artificial
<220> FEATURE:
<223> OTHER INFORMATION: Oligonucleotide 1.107v; Example2

<400> SEQUENCE: 35

```
aacctgcaca ggtgtacata tagtctaatt agactatatg tacacctgtg caggttacta    60
gtagatctgc tagccgccag                                                80
```

<210> SEQ ID NO 36
<211> LENGTH: 81
<212> TYPE: DNA
<213> ORGANISM: Artificial
<220> FEATURE:
<223> OTHER INFORMATION: Oligonucleotide 3.1

<400> SEQUENCE: 36

```
tatggaaaaa cgccagcaac gcggcctttt tacggttcct ggccttttgc tggccttttg    60
```
ctcacatgta gatcttgtac a                                             81

<210> SEQ ID NO 37
<211> LENGTH: 200
<212> TYPE: DNA
<213> ORGANISM: Artificial
<220> FEATURE:
<223> OTHER INFORMATION: Oligonucleotide 3.2

<400> SEQUENCE: 37 gggcggggt cgttgggcgg tcagccaggc gggccattta ccgtaagtta tgtaacgcgg      60
aactccatat atgggctatg aactaatgac cccgtaattg attactactt aagtgtacat     120
atcagcacac aatagtccat tatacgcgcg tataatgggc aattgtgtgc tgatatgtac    180
aagatctaca tgtgagcttt                                               200

<210> SEQ ID NO 38
<211> LENGTH: 200
<212> TYPE: DNA
<213> ORGANISM: Artificial
<220> FEATURE:
<223> OTHER INFORMATION: Oligonucleotide 3.3

<400> SEQUENCE: 38
ataatgccag gcgggccatt taccgtcatt gacgtcaata gggggcgtac ttggcatatg      60
atacacttga tgtactgcca agtgggcagt ttaccgtaaa tactccaccc attgacgtca    120
atggaaagtc cctattggcg ttactatggg aacatacgtc attattgacg tcaatgggcg    180
ggggtcgttg ggcggtctcg                                               200

<210> SEQ ID NO 39
<211> LENGTH: 200
<212> TYPE: DNA
<213> ORGANISM: Artificial
<220> FEATURE:
<223> OTHER INFORMATION: Oligonucleotide 3.4

<400> SEQUENCE: 39
gccaaaacaa actcccattg acgtcaatgg ggtggagact tggaaatccc cgtgagtcaa     60
accgctatcc acgcccattg atgtactgcc aaaaccgcat caccatggta atagcgatga    120
ctaatacgta gatgtactgc caagtaggaa agtcccataa ggtcatgtac tgggcataat    180
gccaggcggg ccatttaggc                                               200

<210> SEQ ID NO 40
<211> LENGTH: 64
<212> TYPE: DNA
<213> ORGANISM: Artificial
<220> FEATURE:
<223> OTHER INFORMATION: Oligonucleotide 3.5

<400> SEQUENCE: 40
ccattatacg cgcgtataat gggcaattgt gtgctgatag ccaaaacaaa ctcccattga     60
ccag                                                                64

<210> SEQ ID NO 41
<211> LENGTH: 159
<212> TYPE: DNA
<213> ORGANISM: Artificial
<220> FEATURE:
<223> OTHER INFORMATION: Oligonucleotide DNA-T

<400> SEQUENCE: 41

```
tactagtcat ctatcagcac acaattgccc attatacgcg cgtataatgg actattgtgt    60
gctgatatac taggcaccac ctgcaggaat ctactaggcc gccgcaacca aacttggatc   120
ggtgcacatg tcgaatacta ggattcctgc aggtggtgc                         159

<210> SEQ ID NO 42
<211> LENGTH: 159
<212> TYPE: DNA
<213> ORGANISM: Artificial
<220> FEATURE:
<223> OTHER INFORMATION: Oligonucleotide DNA-V

<400> SEQUENCE: 42
tactagtcat caacctgcac aggtgtacat atagtctaat tagactatat gtacacctgt    60
gcaggtttac taggcaccac ctgcaggaat ctactaggcc gccgcaacca aacttggatc   120
ggtgcacatg tcgaatacta ggattcctgc aggtggtgc                         159

<210> SEQ ID NO 43
<211> LENGTH: 10
<212> TYPE: DNA
<213> ORGANISM: Artificial
<220> FEATURE:
<223> OTHER INFORMATION: Oligonucleotide: exemplary sequence figure 4a

<400> SEQUENCE: 43
tcgacgtcga                                                          10

<210> SEQ ID NO 44
<211> LENGTH: 56
<212> TYPE: DNA
<213> ORGANISM: Escherichia coli bacteriophage N15
<220> FEATURE:
<221> NAME/KEY: misc_feature
<223> OTHER INFORMATION: protelomerase target sequence hairpin

<400> SEQUENCE: 44
tatcagcaca caatagtcca ttatacgcgc gtataatgga ctattgtgtg ctgata        56

<210> SEQ ID NO 45
<211> LENGTH: 56
<212> TYPE: DNA
<213> ORGANISM: Escherichia coli bacteriophage N15
<220> FEATURE:
<221> NAME/KEY: misc_feature
<223> OTHER INFORMATION: protelomerase target sequence hairpin

<400> SEQUENCE: 45
tatcagcaca caattgccca ttatacgcgc gtataatggg caattgtgtg ctgata        56

<210> SEQ ID NO 46
<211> LENGTH: 90
<212> TYPE: DNA
<213> ORGANISM: Halomonas phage Phi HAP
<220> FEATURE:
<221> NAME/KEY: misc_feature
<223> OTHER INFORMATION: protelomerase target sequence

<400> SEQUENCE: 46
cctatattgg gccacctatg tatgcacagt tcgcccatac tatacgtata gtatgggcga    60
actgtgcata cataggtggc ccaatatagg                                    90

<210> SEQ ID NO 47
<211> LENGTH: 88
```

```
<212> TYPE: DNA
<213> ORGANISM: Vibrio Phage VP58.5
<220> FEATURE:
<221> NAME/KEY: misc_feature
<223> OTHER INFORMATION: protelomerase target sequence

<400> SEQUENCE: 47
taactgtaca tataccaacc tgcacaggtg tacatatagt ctaattagac tatatgtaca      60
cctgtgcagg ttggtatatg tacagtta                                        88
```

METHOD OF DNA SYNTHESIS

CROSS-REFERENCE TO RELATED APPLICATIONS

This application is the U.S. national phase entry under 35 U.S.C. § 371 of International Application No. PCT/GB2016/050399, filed on Feb. 17, 2016, which claims priority to British Patent Application No. GB1502645.3, filed on Feb. 17, 2015.

SEQUENCE LISTING

This application contains a sequence listing, which has been submitted electronically in ASCII format and is hereby incorporated by reference in its entirety. Said ASCII copy of the sequence listing was created on Sep. 10, 2020, under the filename 00012-0024-00000_SL.txt and is 62,286 bytes in size.

FIELD OF THE INVENTION

The present invention relates to an in vitro cell-free process for production of deoxyribonucleotides (DNAs) comprising at least one hairpin, corresponding DNA products and uses thereof, and oligonucleotides and kits useful in the process of the invention.

BACKGROUND OF THE INVENTION

In vitro, cell-free processes for amplification of closed linear DNA from a starting template have been described in WO2010/086626 and WO2012/017210. It would be desirable to provide further processes which can synthesise closed linear DNA, and which also allow for synthesis of other types of DNA molecules comprising one or more hairpins.

SUMMARY OF THE INVENTION

The invention provides a process for synthesis of DNA molecules comprising one or more hairpins which does not require use of any microbiological steps for provision of a starting template. The process also allows for synthesis of circular single-stranded DNA or double-stranded DNA comprising one or more hairpins. These products include DNA molecules which the inventors believe to have structures not previously described in the art, and which have advantages for a wide range of applications.

According to the present invention, synthesis of DNA molecules comprising hairpins is carried out in an in vitro cell-free process starting from an oligonucleotide which can be immobilised to a solid support during all or part of the process. The oligonucleotide is extended enzymatically to synthesise a desired DNA sequence, using short template oligonucleotides which can be synthesised chemically, thus avoiding use of large starting templates encoding the entirety of the desired sequence which would typically need to be propagated in bacteria. Once a desired DNA sequence is synthesised, it can be released from the solid support in a single-stranded or double-stranded form comprising one or more hairpins.

Advantageously, sequences used to provide hairpins in the DNA molecules of the invention also provide a means for enzymatic release of the synthesised DNA from the solid support on completion of DNA synthesis. An oligonucleotide is immobilised on the solid support and extended to incorporate a desired DNA sequence to create a first DNA strand which further comprises a first portion of a protelomerase target sequence proximal to the solid support. A second portion of the target sequence for the protelomerase, complementary to the first portion thereof is also introduced in the extended first strand or on a complementary second strand. The first and second portions of the target sequence for the protelomerase are then used to recreate a complete protelomerase target sequence proximal to the solid support, such that contacting with a protelomerase can then release the synthesised DNA from the solid support in conjunction with generating a hairpin in the DNA molecule released from the solid support.

In further aspects, the invention provides for addition of a second closed end hairpin to a produced DNA molecule by creation of a complete protelomerase target sequence or other sequence capable of forming a hairpin in the distal, extended region of the synthesised DNA strand. Such a sequence capable of forming a hairpin can include neighbouring complementary sequences or two complementary sequences separated by a sequence which is non-complementary.

In further aspects, the invention provides for the addition of a third, fourth, fifth or further closed end hairpin to a produced single stranded DNA molecule by creation of a complete protelomerase target sequence or other sequence capable of forming a hairpin in the synthesised DNA strand.

The DNA molecules synthesised in accordance with the invention may be used for various applications, including medicinal and diagnostic uses, and also as a starting template for further processes of DNA amplification.

In more detail, the invention provides:

In a first aspect, an in vitro cell-free process for production of a deoxyribonucleic acid (DNA) which comprises a desired DNA sequence, said process comprising:

(a) contacting an oligonucleotide immobilised on a solid support with a series of template oligonucleotides which overlap in sequence, in the presence of at least one DNA polymerase under conditions promoting template-dependent extension of said immobilised oligonucleotide to produce a first DNA strand which comprises the desired DNA sequence and further comprises a first portion of the protelomerase target sequence proximal to the solid support;

(b) introducing a DNA sequence comprising a second portion of the protelomerase target sequence of (a) in the distal part of said first DNA strand produced in (a), or on a second or further strand, such that said first and second portions of the protelomerase target sequence thereby create a complete target sequence for the protelomerase of (a) proximal to said solid support; and (c) contacting said complete protelomerase target sequence proximal to said solid support with a protelomerase under conditions promoting cleavage and rejoining of said target sequence, to thereby release the produced DNA from immobilisation.

In one embodiment, the first and second portions of the protelomerase target sequence are complementary in sequence.

In another aspect, the invention relates to a solid support comprising an immobilised oligonucleotide comprising a first portion of a target sequence for a protelomerase.

In a further aspect, the invention relates to a kit comprising an oligonucleotide comprising a first portion of a target sequence for a protelomerase, a series of template oligonucleotides, and optionally instructions for use in a process of the invention.

In a fourth aspect, the invention relates to a single-stranded circular DNA comprising one or more hairpins, at least one of which comprises a portion of a target sequence for a protelomerase.

In a fifth aspect, the invention relates to a linear covalently closed double-stranded DNA comprising a first hairpin comprising a portion of a target sequence for a first protelomerase and a second hairpin which has a sequence which is not complementary to the first hairpin. In one embodiment, this is achieved by the second hairpin comprising a portion of a target sequence for a second protelomerase, wherein said first and second protelomerases are different. In an alternative embodiment, this is achieved by the second hairpin comprising a sequence capable of forming a hairpin. Such sequence may include neighbouring or separated complementary sequences, which are capable of annealing to each other.

In a sixth aspect, the invention relates to an in vitro cell-free process for amplification of DNA, comprising contacting a single-stranded circular DNA template comprising a hairpin comprising a portion of a target sequence for a protelomerase, with at least one DNA polymerase in the presence of one or more primers under conditions promoting amplification of said template.

In a seventh aspect, the present invention relates to an in vitro cell-free process for production of a linear covalently closed deoxyribonucleic acid (DNA) comprising:
(a) contacting a linear covalently closed double-stranded DNA comprising a first hairpin comprising a portion of a target sequence for a first protelomerase and a second hairpin comprising a portion of a target sequence for a second protelomerase with a DNA polymerase under conditions promoting DNA amplification, and
(b) contacting the amplified DNA with said first and second protelomerases under conditions promoting production of linear covalently closed DNA,
wherein said first and second protelomerases are different.

In an eighth aspect, the present invention relates to a single-stranded circular DNA comprising at least one hairpin comprising a portion of a target sequence for a protelomerase, for use in therapy or diagnosis, particularly for use in a method for treatment of the human or animal body, or in a diagnostic method practised on the human or animal body.

In a ninth aspect, the invention relates to a linear covalently closed double-stranded DNA comprising at least one hairpin comprising a portion of a target sequence for a first protelomerase and wherein the sequence of the second hairpin is not complementary to the sequence of the first hairpin, for use in therapy or diagnosis, particularly for use in a method for treatment of the human or animal body, or in a diagnostic method practised on the human or animal body. In one embodiment the second hairpin comprises a portion of a target sequence for a second protelomerase, wherein said first and second protelomerases are different. In an alternative embodiment, the second hairpin is provided by neighbouring or separated complementary sequences.

In a tenth aspect, the invention relates to a method of treatment of the human or animal body, comprising administering a therapeutically effective amount of a single-stranded circular DNA comprising a hairpin comprising a portion of a target sequence for a protelomerase to a human or animal in need thereof.

In an eleventh aspect, the invention relates to a method of treatment of the human or animal body, comprising administering a therapeutically effective amount of a linear covalently closed double-stranded DNA comprising at least one hairpin comprising a portion of a target sequence for a first protelomerase and wherein the sequence of the second hairpin is not complementary to the sequence of the first hairpin, to a human or animal in need thereof. In one embodiment the second hairpin comprises a portion of a target sequence for a second protelomerase, wherein said first and second protelomerases are different. In an alternative embodiment, the second hairpin is provided by neighbouring or separated complementary sequences.

Optional features are defined in the dependent claims. Further advantages are described below.

BRIEF DESCRIPTION OF FIGURES

FIG. 1a depicts an oligonucleotide (100) that can be used as a starting primer or as a terminal oligonucleotide template and primer. The oligonucleotide contains a portion of a protelomerase target sequence (101), flanked by a 3' sequence (104) and a 5' sequence (105) that do not form part of the sequence of the protelomerase target sequence. The entire sequence of the oligonucleotide (106) may include a region designed to be complementary to a template oligonucleotide or synthesized strand.

FIG. 1b depicts a terminal oligonucleotide primer (110). In this example, this contains a portion of a protelomerase target sequence (107) which comprises a different and non-complementary sequence to the one shown in FIG. 1(a) as (101). This sequence is flanked by a 3' sequence (109) and a 5' sequence (111) which do not form part of the protelomerase target sequence. The 3' flanking sequence also contains a region (108) which has a sequence which is non-complementary to the synthesized strand, whilst the remaining sequence of the oligonucleotide primer (110) shown as 112 may be complementary in sequence to a synthesized strand.

FIG. 1c depicts an oligonucleotide (120) that can act as a starting primer or template, or a terminal oligonucleotide or template. It comprises a hairpin structure (220) that may comprise a portion of a protelomerase target sequence, flanked by a 3' sequence (114) and a 5' sequence (113), which flanking sequences do not form part of the protelomerase target sequence, if such is present. A region of the 3' flanking sequence may comprise a region (115) which is not complementary to the 5' flanking sequence and which is complementary to either a template oligonucleotide or a synthesized strand.

FIG. 2 (FIGS. 2a and 2b) depicts various ways of immobilising an oligonucleotide to a solid support.

FIG. 3 (FIGS. 3a to 3j) depicts an example of some of the steps involved in one method of the invention, in which an oligonucleotide (100a) is immobilised to a solid support (121) via a spacer molecule (122) and a succession of template oligonucleotides (130) are added, together with DNA polymerase, in order to extend the oligonucleotide. The template oligonucleotide is removed after extension is complete and a further template oligonucleotide is added until the desired sequence has been achieved (133). At this point an oligonucleotide (100b) is added which acts as both a template and a terminal primer, and a complementary second strand (136) of DNA is synthesized. Once a double-stranded sequence has been synthesized, the product (140) is released from the solid support using protelomerase (not shown) and leaves a by-product on the solid support (138).

FIG. 3e shows the extension of the first strand (133) following a repeated application, extension (using DNA polymerase) and removal of template oligonucleotide. The synthesised sequence of the first strand (133) is complementary to the template oligonucleotides used to construct it, in the order that they are used.

FIG. 3f shows the presence of an oligonucleotide (100b), comprising a second portion of a protelomerase target sequence (101b), which acts as a template and a terminal primer.

FIG. 3g shows the binding of the oligonucleotide (100b) to the first strand (133) via a region of complementary sequence (134). Both 3' termini (102b and 141) are available for extension by DNA polymerase (not shown).

FIG. 3h shows the complementary sequences synthesized by DNA polymerase (not shown) to the terminal primer/template, complementary sequences are shown here in dashed lines. The complementary sequence to the oligonucleotide (100b) is shown as a dashed line (135) and the complementary sequence to the first strand (133) is also shown as a dashed line (136). The complementary sequence is also known as the complementary second strand (136).

FIG. 3i shows the first strand (133) and complementary second strand (136). The first and second portions of the protelomerase target sequence (101a and 101b) have been used as templates by the DNA polymerase to form two complete protelomerase target sequences (137a and 137b).

FIG. 3j shows the result of using a protelomerase on the first strand (133) and complementary second strand (136) of FIG. 3i. The complete protelomerase target sites (137a and b) are cleaved and ligated, forming a released product (140) which shown here is a closed linear DNA, leaving a by-product linked to the solid support (138) and a further free by-product (139), which is single-stranded DNA with an internal hairpin and free 3' and 5' ends.

FIG. 4 (FIGS. 4a to 4f) depicts a further example of a method of the invention for producing covalently closed double stranded or single stranded DNA, via key steps a to f. Other steps are not shown. Double stranded DNA will be produced if the created hairpin structure does not include a loop of single-stranded DNA as shown in FIG. 4d. However, if the hairpin (185) in FIG. 4d includes a longer intervening single stranded sequence, this may be the major section of the molecule and a minimal amount of double stranded sequence may be present, as shown in FIG. 4h FIG. 4a shows an immobilised oligonucleotide (100a) including a first portion of a protelomerase target sequence (101a), immobilised via a spacer molecule (122) attached to a solid-support (121). The immobilised oligonucleotide has been extended via template-dependent extension, to produce a first strand (133). Shown is a template oligonucleotide (130) bound to the first strand (133) near the 3' end (141) including a section of sequence (181). An exemplary sequence (183) of the template oligonucleotide is shown. The template oligonucleotide binds at the 3' end of the first strand (141). The remaining part of the template oligonucleotide overhangs the 3' end of the first strand.

FIG. 4b depicts the same structure once DNA polymerase has catalysed the extension of the 3' end (141) of the first strand (133) using the template oligonucleotide (130) to create a complementary sequence (dashed line). This complementary sequence includes a sequence (184) complementary to the exemplary sequence (183) in the template oligonucleotide (130).

FIG. 4e shows the result of extending the 3' end (141) of the first strand shown in FIG. 4d using DNA polymerase. The segment of the first strand (133) between the solid support and the hairpin acts as a template for the second segment of the first strand (186—dashed line), until the DNA reaches the spacer molecule (122). A second portion of a protelomerase target sequence is synthesised (101b) using the first portion as a template (101a), resulting in the formation of an entire protelomerase target sequence (137).

FIG. 4f demonstrates the results of adding a protelomerase to the structure of FIG. 4e. A closed linear DNA product (187) is released and a by-product (188) is left immobilised to the solid support. Note that the closed linear DNA is closed at one end with a portion of a protelomerase target sequence at one end (101) and with a template-derived hairpin at the other (189).

FIG. 4g depicts an alternative embodiment, wherein the segment of sequence (181) is not present at the 3' end of the first strand (133), and the terminal template oligonucleotide (130) does not anneal thereto. The template oligonucleotide binds to a section of complementary sequence (182).

FIG. 4h depicts the structure obtained by extension of the 3' end of the first strand of FIG. 4g. An intervening sequence (185) is formed between the complementary sequences (181 and 184), which is looped out as a single strand of DNA, of any particular length.

FIG. 5 (FIGS. 5a to 5e) depicts a further example of the method of the invention. An oligonucleotide (120a) is immobilised and the 3' end (102) extended using rounds of template oligonucleotide dependent extension to form a first strand (133). A final template oligonucleotide (120b) comprising a hairpin (225 is added which acts as a template to introduce sequences in the distal 3' end of the first strand which are capable of forming a hairpin due to self—complementary internal sequences. The synthesis of the complementary second segment of the first strand (211) uses the first segment of the first strand as a template. Once the double stranded sequence is complete, protelomerase (not shown) acts at the complete protelomerase target site (137) to cleave the sequence and re-join the created free ends, releasing a product (212) and a by-product (143).

FIG. 5a shows the extended immobilised oligonucleotide (120a) including a first portion of a protelomerase target sequence (220a) forming a first strand (133), to which is bound an oligonucleotide (120b) including a hairpin structure (225), which in this example is not a portion of a protelomerase target sequence.

FIG. 5b shows the structure of FIG. 5a with the template oligonucleotide (120b) in unfolded, single-stranded form, and the DNA polymerase (not shown) has catalysed extension of the 3' end of the first strand (133), using the template (120b), resulting in synthesis of the sequence shown as a dashed line (210).

FIG. 5c shows the structure of FIG. 5b with the template oligonucleotide (120b) removed, and the synthesized sequence (210) forming a hairpin due to internal self-complementary sequences (not shown). The 3' end (141) of the extended first strand (133) is thus available for extension.

FIG. 5d shows the structure of FIG. 5c once DNA polymerase (not shown) has catalysed the extension of the 3' end (141), using the first segment of the first strand (133) as a template, to produce a complementary second segment of the first strand (211). The second segment of the first strand includes a portion of a protelomerase target sequence (220b), thus forming an entire protelomerase target sequence (137) proximal to the solid support.

FIG. 5e depicts the results of adding protelomerase (not shown) to the structure of FIG. 5d. A product (212), in this case a closed linear DNA is formed, with one end closed with a portion of a protelomerase target sequence (220d) and a hairpin structure at the other (225), together with a by-products (143).

FIG. 6 (FIGS. 6a to 6e) depicts the synthesis of a covalently closed single stranded DNA molecule, via key steps a-e. Other steps are not shown.

FIG. 6b depicts the structure of FIG. 6a after DNA polymerase has catalysed extension of the 3' end (141), to produce a sequence complementary (135—dashed line) to the oligonucleotide template (100b). A complete protelomerase target sequence (137) is formed. The 3' end (102b) of the template oligonucleotide (100b) will also be extended by the DNA polymerase unless it is modified to prevent extension or it includes a segment of sequence that is not complementary to the first strand, such as the structure shown in FIG. 1b.

FIG. 6c depicts the first strand of the oligonucleotide (133) as shown in FIG. 6b, once the oligonucleotide template (100b) has been removed. The arrow depicts the folding back of the distal 3' end (141) of the first strand (133), bringing the 3' end into close proximity to the solid support (121).

FIG. 7 (FIGS. 7a to 7e) depicts an alternative method of producing covalently closed single stranded DNA via key steps a-e. Other steps are not shown.

FIG. 7a shows an immobilised oligonucleotide (100a) comprising a first portion of a protelomerase target sequence (101a), immobilised via a spacer molecule (122) attached to a solid-support (121). The immobilised oligonucleotide has been extended via template-dependent extension, to produce a first strand (133). Shown is a template oligonucleotide (130) bound to the first strand (133) near the 3' end (141). An exemplary sequence in the template oligonucleotide is shown (161). The 3' (160) portion of the template oligonucleotide anneals to the complementary sequence in the first strand (133) and a section of single stranded template (164) overhangs the 3' end of the first strand, including the exemplary sequence (161).

FIG. 7b depicts the structure of FIG. 7a after DNA polymerase has catalysed extension of the 3' end (141) of the first strand (133), to produce a sequence complementary (dashed line) to the oligonucleotide template (130), including a complementary sequence (162) to the exemplary sequence (161)

FIG. 7c depicts the first strand of the oligonucleotide (133) as shown in FIG. 7b, once the template oligonucleotide has been removed. The arrow depicts the folding back of the 3' end (141) of the first strand (133), bringing the distal 3' end into close proximity to the solid support (121) and the proximal end of the immobilised oligonucleotide (100a).

FIG. 7d depicts the annealing of the complementary sequences in the 5' flanking region (104a) of the first portion of the protelomerase target sequence (101a) and the sequence (162) on the distal end of the first strand (133), forming a duplex. Since the sequence of the remaining part of the first strand (133) is not complementary, it remains in single strand form as a looped structure (153).

FIG. 8 (FIGS. 8a to 8f) depicts an example of a method of the invention for producing covalently closed single stranded DNA, via key steps a to f. Other steps are not shown. FIG. 8a shows an immobilised oligonucleotide (100a) including a first portion of a protelomerase target sequence (101a), immobilised via a spacer molecule (122) attached to a solid-support (121). The immobilised oligonucleotide has been extended via template-dependent extension, to produce a first strand (133). Shown is a template oligonucleotide (110) bound to the first strand (133) near the 3' end (141). This includes a first portion of a protelomerase target sequence (107a) which is not complementary to the portion in the immobilised oligonucleotide (101a). Only the flanking sequence (109) of the template oligonucleotide anneals to the complementary sequence in the first strand (133), the remaining part of the 3' section of the template oligonucleotide (108) is not complementary to the first strand (133) and does not anneal. A section of single stranded template remains, including the portion of the protelomerase target sequence (107a) and the 5' flanking sequence (111).

FIG. 8b depicts the structure of FIG. 8a after DNA polymerase has catalysed extension of the 3' end (141) of the first strand (133), to produce a sequence complementary (171—dashed line) to the template oligonucleotide (110). A second portion of a protelomerase target sequence (107b) is synthesised, creating an entire protelomerase target sequence (200).

FIG. 8c shows the result of applying protelomerase specific for the entire protelomerase target sequence (200) created in FIG. 8b. A by-product (172) is released which is a single stranded piece of DNA that may form a hairpin structure. The first strand (133) now includes a hairpin structure (230). The 3' end of the DNA strand is now the non-complementary sequence section (108) from the oligonucleotide (110), and this forms the start of the non-complementary second segment of the extended first strand. It will be understood that the cognate protelomerase can be applied at any suitable time.

FIG. 8d depicts the result of extending the 3' end (141) of the second segment of the extended first strand (173) using template dependent techniques as described previously. Templates are designed such that the terminal sequences (174) of the second segment of the extended first strand (173) are complementary to the immobilised oligonucleotide (100a), and include a second portion of a protelomerase target sequence (101b), a 3' flanking region (175) and a 5' flanking region (176) which are complementary to the immobilised oligonucleotide (100a).

FIG. 8e shows the annealing of the sequences (175, 176 and 101b) in the second segment of the extended first strand (173) and sequences (104a, 105a and 101a) in the first segment of the first strand (133). An entire protelomerase target sequence is created (137) as the first portion (101a) and second portion (101b) are juxtaposed. The nucleotide sequences shown are exemplary only.

FIG. 8f depicts the result of applying a protelomerase specific for the complete protelomerase target sequence (137). A single stranded circular structure (177) is released. This circular structure may form hairpin structures at two points (179 and 180) around the circle, but may also be present without these folds (not shown). The two strands (133 and 173) separated by the hairpin structures are non-complementary and do not anneal to form a double stranded structure or duplex. A by-product (178) is left immobilised to the solid support.

FIG. 11b shows the sequence of FIG. 11a in a linear format, without the hairpin structures. It can be seen that the first portion of the protelomerase target sequence (101a) has a sequence which is complementary to the second portion of the protelomerase target sequence (101b). At the centre (in this example) of the protelomerase target sequence (190) is the site at which the protelomerase will cleave the sequence, which is in the centre of the telO sequence (201). The complete protelomerase target sequence (137—SEQ ID No. 15) is composed of TelRL for the enzyme TelN. The sequence forming TelR is shown (203) and TelL (202).

FIG. 11c shows what happens to the sequences of FIG. 11a/11b once protelomerase catalyses the reaction. The sequence is cleaved at the point indicated (190) and the each cleaved ends are re-ligated with the opposing strand to form two separate hairpin structures. In this instance, a by-product (191) is left annealed to the solid support and a product (192) is released, with a closed end, due to the action of the protelomerase.

FIG. 13 shows the whole native target sequences for a selection of protelomerase enzymes, showing the sequences of both strands of the complementary DNA. Shown are the target sequences: the sequence of SEQ ID NO: 15 (*E. coli* N15 TelN protelomerase), the sequence of SEQ ID NO: 16

(*Klebsiella* phage Phi K02 protelomerase), the sequence of SEQ ID NO: 17 (*Yersinia* phage PY54 protelomerase), the sequence of SEQ ID NO: 46 (Halmonas phage Phi HAP), the sequence of SEQ ID NO: 18 (*Vibrio* phage VP882 protelomerase), the sequence of SEQ ID NO: 19 (*Borrelia burgdorferi* protelomerase) the sequences of SEQ ID NO: 20 and 22 (*Agrobacterium tumefaciens* TelA protelomerase) and the sequence of SEQ ID NO: 47 (*Vibrio parahaemolyticus* plasmid Vp58.5 protelomerase). Where the minimum sequence length requirement for the cognate protelomerase is known, this has been indicated by shading the sequence grey, although the enzyme may accept some variation in sequence within this core target sequence. Nucleotides represented in bold and underlined indicate imperfections in the palindrome sequence. The vertical line through the sequences represents the centre of the perfect inverted sequence and the point at which the protelomerase cleaves and joins the target sequence.

FIG. 14 is a photograph of a gel produced in Example 2. The gel has 5 marked lanes, dsDNA is full length linear DNA, TelN, is the dsDNA treated with TelN, VP58.5 is DNA alternatively treated with VP58.5, whilst both indicates both protelomerase enzymes were applied. T5 represents the sample after addition of the T5 exonuclease. The gel thus shows the progression of the reaction from construction of the dsDNA via template primer extension to cleavage with one or two protelomerases, and final clean up using T5 exonuclease to remove any unwanted open fragments. The photograph is of the gel exposed to blue light at 490 nm to show only fluorescently tagged molecules. Arrows indicate the bands depicting dNTPs and fluorescently labelled oligonucleotides that have not been incorporated into full-length product.

FIG. 15 is a photograph of the same gel as FIG. 14, with the exception that it has been stained with GelRed and exposed to UV light at 300 nm. This shows all of the oligonucleotides and fragments produced during the reactions of Example 2.

FIG. 16 is a photograph of a gel where staining with GelRed has been performed and exposed to UV light at 300 nm to show all oligonucleotides and DNA present in the 10% TBE gel. 10 lanes are shown, with molecular ladders included (LR) to allow determination of approximate molecular weight of the DNA/oligonucleotides. The labels are consistent with those used for FIG. 14. The production of closed linear DNA (dbDNA) is confirmed by the presence of a band as marked on the gel photograph.

Figure 17A:
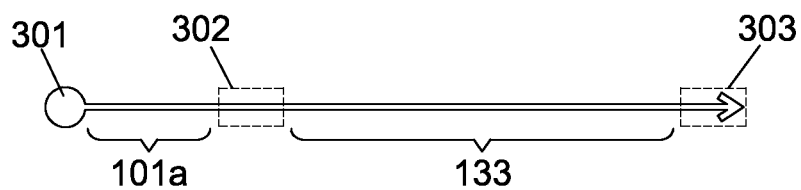
Figure 17B:
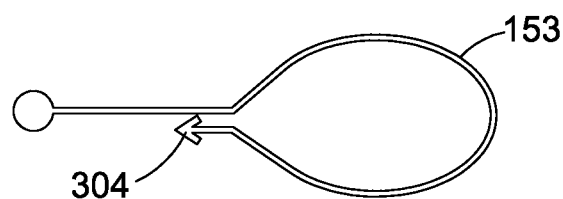
Figure 17C:
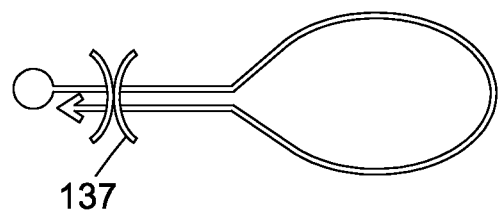

FIGS. 17*a* to 17*c* depicts a schematic representation of the method used in Example 4. An oligonucleotide is attached to a 5' tag (301) and may include a portion of a protelomerase target site (101*a*), together with two reverse complementary sequences (302 and 303) separated by an intervening sequence (133). This is shown on FIG. 17*a*. FIG. 17*b* depicts the looping back and annealing of the complementary sequences (302 and 303), leaving a free 3' end (304) available for extension, using the first strand as a template. FIG. 17*c* shows that an entire protelomerase target site is synthesised by the action of DNA polymerase (137), which allows protelomerase to cleave the molecule at this point and release the 5' tag (301), and leave a circular single stranded DNA structure with one protelomerase-derived hairpin.

Figure 18A:
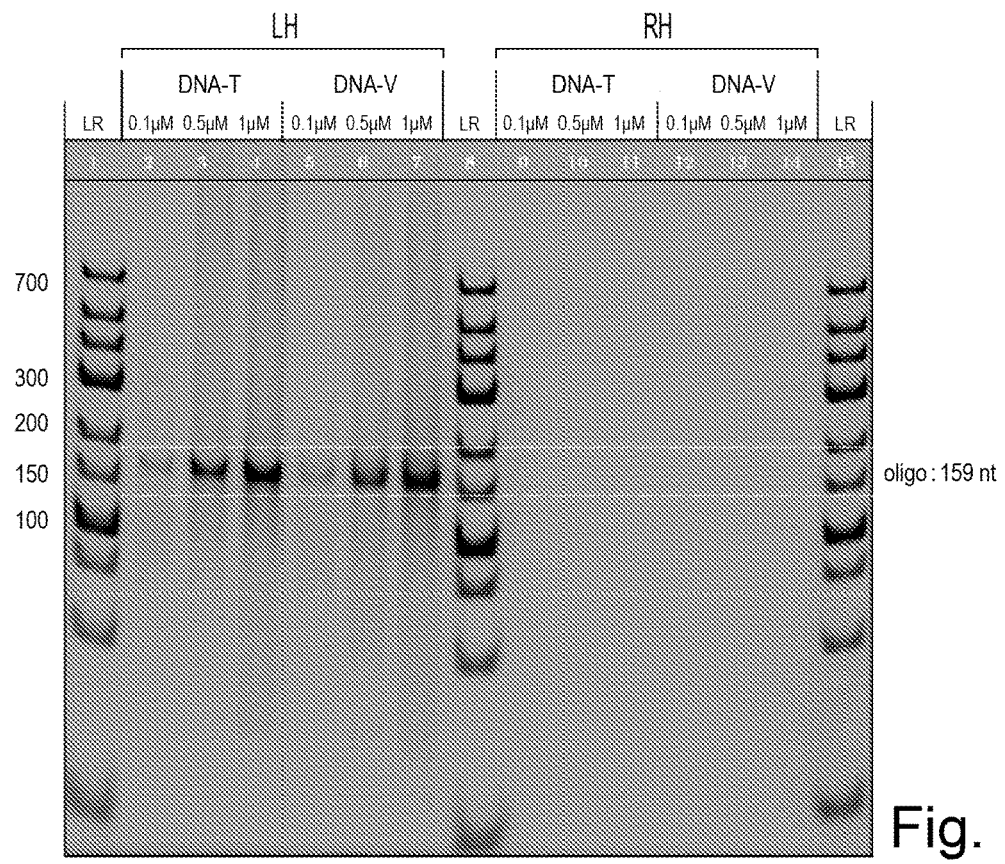

FIG. 18*a* is a photograph of a gel obtained using Example 4. This shows DNA oligonucleotides DNA-T and DNA-V, at the varying concentrations indicated, after temperature cycling reactions with DNA polymerase to extend and complete the protelomerase site. The left hand side of the gel (LH) shows the looped extended DNA-T and DNA-V (both 159 nucleotides) which have not been exposed to their cognate protelomerases nor T5 exonuclease. The right hand side (RH) of the gel shows the looped extended DNA-T and DNA-V which have been exposed only to T5 exonuclease. This attacks the DNA structures with free ends and thus no structures are seen.

Figure 18B:
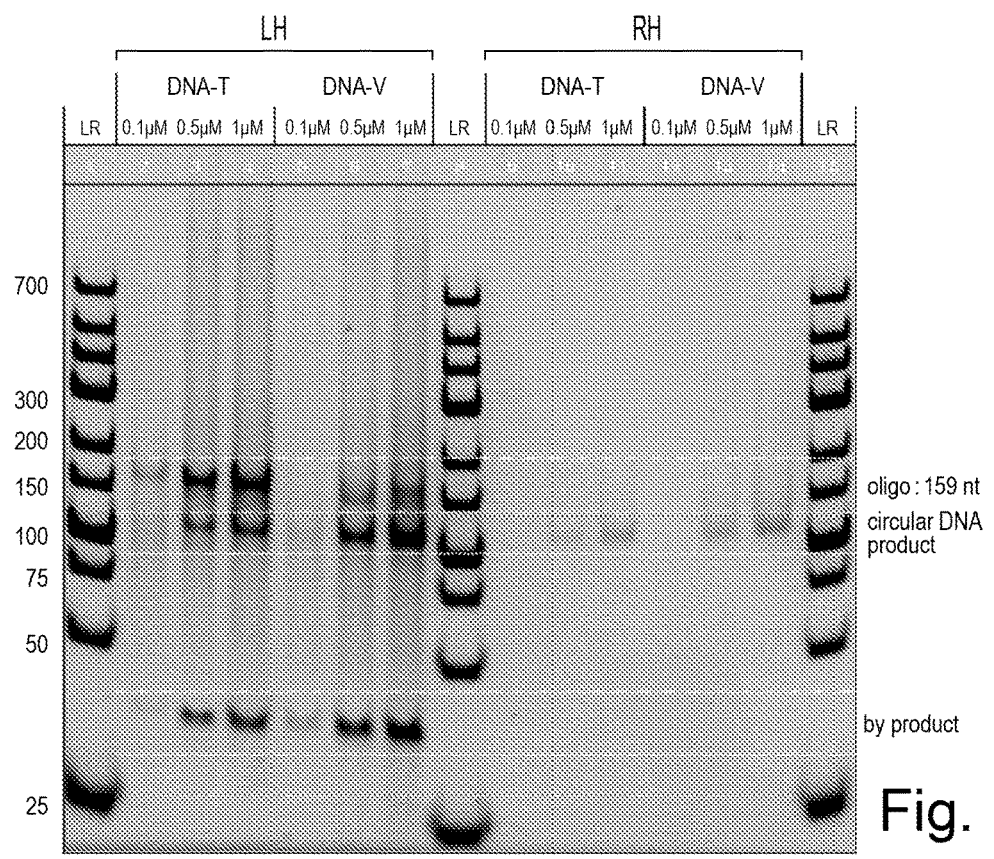

FIG. 18*b* is a photograph of a gel obtained using Example 4. This shows DNA oligonucleotides DNA-T and DNA-V, at the varying concentrations indicated, after temperature cycling reactions with DNA polymerase to extend and complete the protelomerase site. The left hand side of the gel (LH) shows the looped extended DNA-T and DNA-V which have been treated with the cognate protelomerase (TelN for DNA-T and VP58.5 for DNA-V). This catalyses cleavage/joining resulting in a circular DNA product and by-product as indicated. The right hand side (RH) of the gel shows the looped extended DNA-T and DNA-V which have been exposed to the cognate protelomerase and then to T5 exonuclease.

DETAILED DESCRIPTION OF THE INVENTION

The process of the present invention utilises an oligonucleotide as a basis for polymerase-mediated extension to produce single-stranded DNA, which may then be converted to double-stranded DNA. The oligonucleotide may be immobilised to a solid support before the polymerase-mediated extension commences, or the oligonucleotide may be immobilised after polymerase-mediated extension in solution. If polymerase-mediated extension takes place in solution prior to immobilisation, it is preferred that 1 to 5 rounds of extension occur, i.e. 1 to 5 separate template oligonucleotides are used in polymerase-mediated extension. The oligonucleotide is immobilised at an appropriate point in the process. The single-stranded DNA or double-stranded DNA is released from the solid support in a closed form comprising at least one hairpin, by contacting with a protelomerase enzyme.

The process of the invention is carried out in an in vitro cell-free environment. Thus, the process is carried out in the absence of a host cell and typically comprises use of purified enzymatic components. Accordingly, the synthesis of DNA and processing by protelomerase is typically carried out by contacting the reaction components in solution in a suitable container. Particular components are provided in immobilisable or immobilised form, which includes the means for attachment to a solid support.

Figure 10:
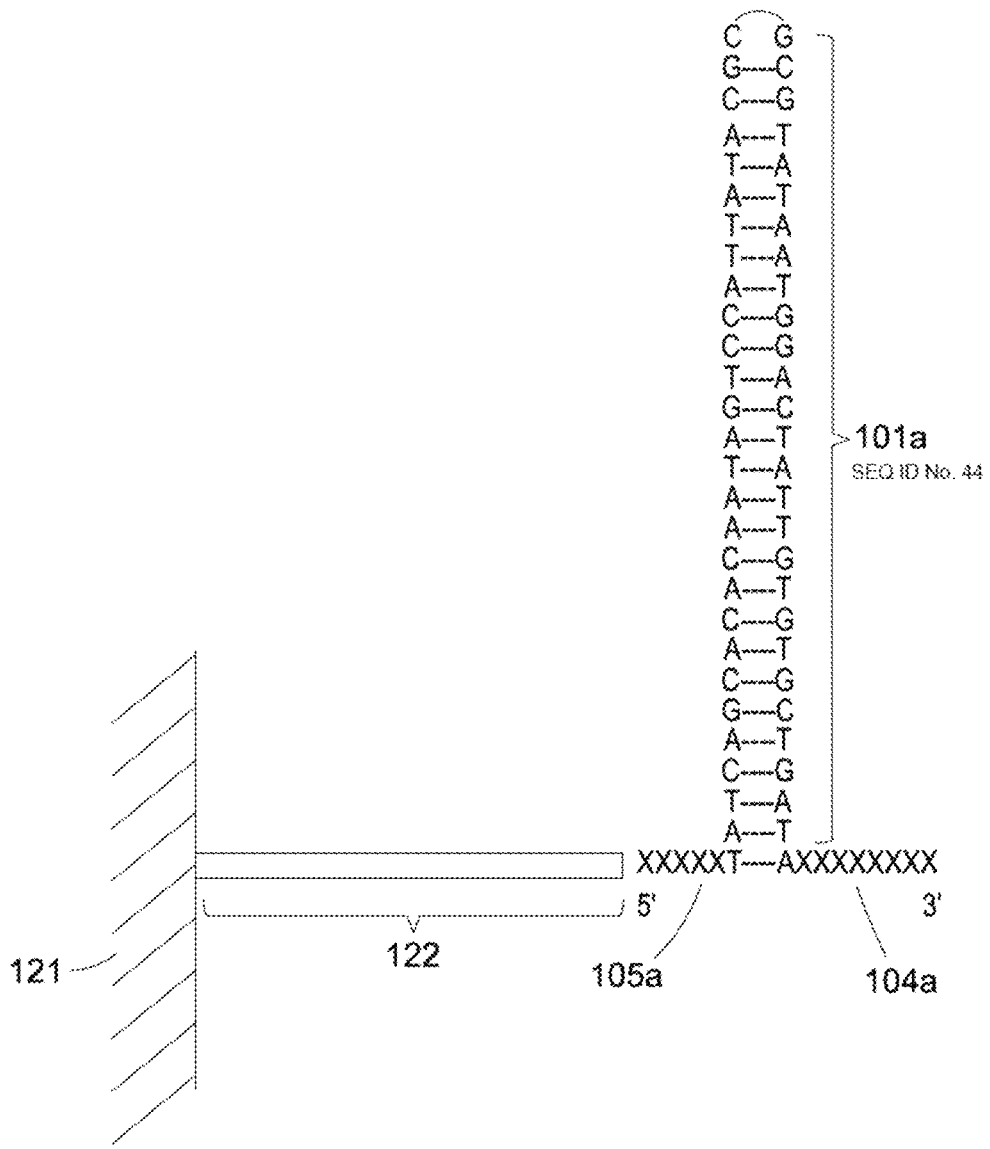
FIG. 10 depicts an immobilised oligonucleotide according to one aspect of the invention. The first portion of a protelomerase target sequence (shown here is one strand of the protelomerase target sequence for protelomerase TelN—SEQ ID No. 17) (101a—SEQ ID No. 44), flanked by a 3' sequence (104a) and 5' sequence (105a). The sequences of the flanking sequence are irrelevant and shown as X and X' to distinguish them from the portion of the protelomerase target sequence (101a). The 5' end of the 5' flanking sequence (105a) is linked to a spacer molecule (122) immobilised to a solid support (121). The base pairing between the residues forming the portion of the protelomerase target sequence (101a) is shown, although it is postulated that the base pairing at the tip of the hairpin may be disrupted due to structural distortion.

A hairpin is a structure in a polynucleic acid, such as DNA or RNA, formed due to base-pairing between neighbouring complementary sequences of a single strand of the polynucleic acid. The neighbouring complementary sequences may be separated by a few nucleotides, eg. 1-10 or 1-5 nucleotides. An example of this is depicted in FIG. 10. If a loop of non-complementary sequence is included between the two sections of complementary sequence, this forms a hairpin loop. The loop may be of any suitable length.

Immobilised Oligonucleotide

The immobilised oligonucleotide of the present invention, or starting primer, is capable of being extended. The immobilised oligonucleotide may be chemically synthesised or may be prepared by template-dependent extension of an initial (shorter) primer, for example in solution. An oligonucleotide may thus be immobilised to a solid support to carry out further template-dependent extension, and to allow for completion of production of a desired sequence to be released from the solid support.

Figure 1A:
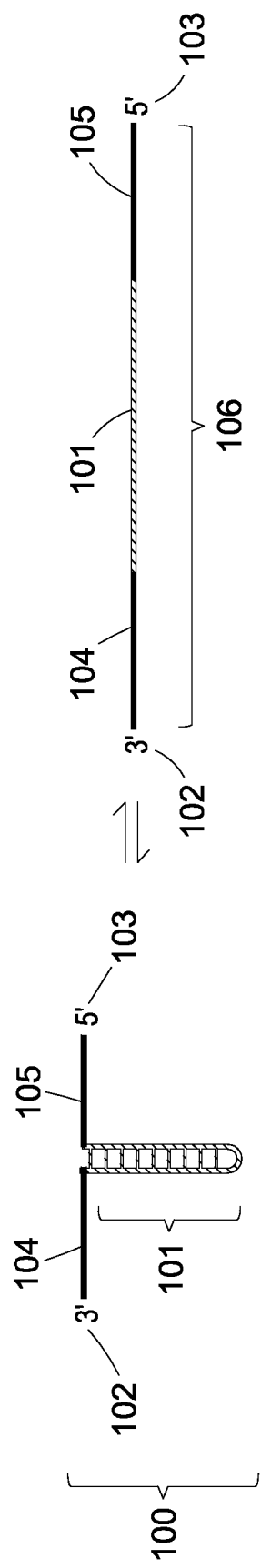
FIGS. 1a to 1c: Depicts schematics of examples of various single stranded oligonucleotides which can act as starting and/or terminating primers and templates. Each is shown in linear format or with the hairpin formed in the portion of the protelomerase target sequence (101 or 107), and has free 3' (102) and 5' (103) ends.

Examples of various oligonucleotides are shown in FIG. 1, and various points of immobilisation are depicted in FIG. 2.

In some embodiments, the immobilised oligonucleotide to be extended on the solid support comprises a first portion of a target sequence for a protelomerase. The first portion of a target sequence for a protelomerase may be derived from any protelomerase target sequence. The first portion of a target sequence for a protelomerase included in the starting primer is designed such that in combination with a second complementary portion of the target sequence for the protelomerase provided as discussed below, a complete protelomerase sequence may be formed. The skilled person is able to divide a protelomerase target sequence into first and second portions which are able to recreate a complete target sequence when juxtaposed together, by reference to the discussion of the characteristics of complete target sequences provided below. The provision of an appropriate pairing of first and second portions of a protelomerase target sequence may also be validated empirically using a suitable assay for protelomerase activity as discussed below. It will be appreciated that the first and second portions of the protelomerase target sequence may each be provided as a single strand of DNA. The first portion may be provided on a different strand of DNA to the second portion, or they may both be provided on the same single strand of DNA, provided that there is sufficient intervening sequence to allow the second portion to be juxtaposed to the first portion. The first and second portions of the protelomerase target sequence may therefore be formed of complementary sequences, allowing them to anneal to one another.

In more detail, a complete protelomerase target sequence cleaved by its cognate protelomerase as described herein is present as a duplex of a first DNA sequence comprising a forward (or sense) portion of a protelomerase target sequence and a complementary second DNA sequence containing the reverse (or antisense) portion of the protelomerase target sequence. The second DNA sequence may comprise the reverse complement of the protelomerase target sequence comprised in the first DNA sequence. In other words, the first portion of the protelomerase target sequence included proximal to the solid support in the first strand forms a complementary duplex with a second portion of the protelomerase target sequence provided at the distal end of the first strand or on a complementary second strand.

Figure 11A:
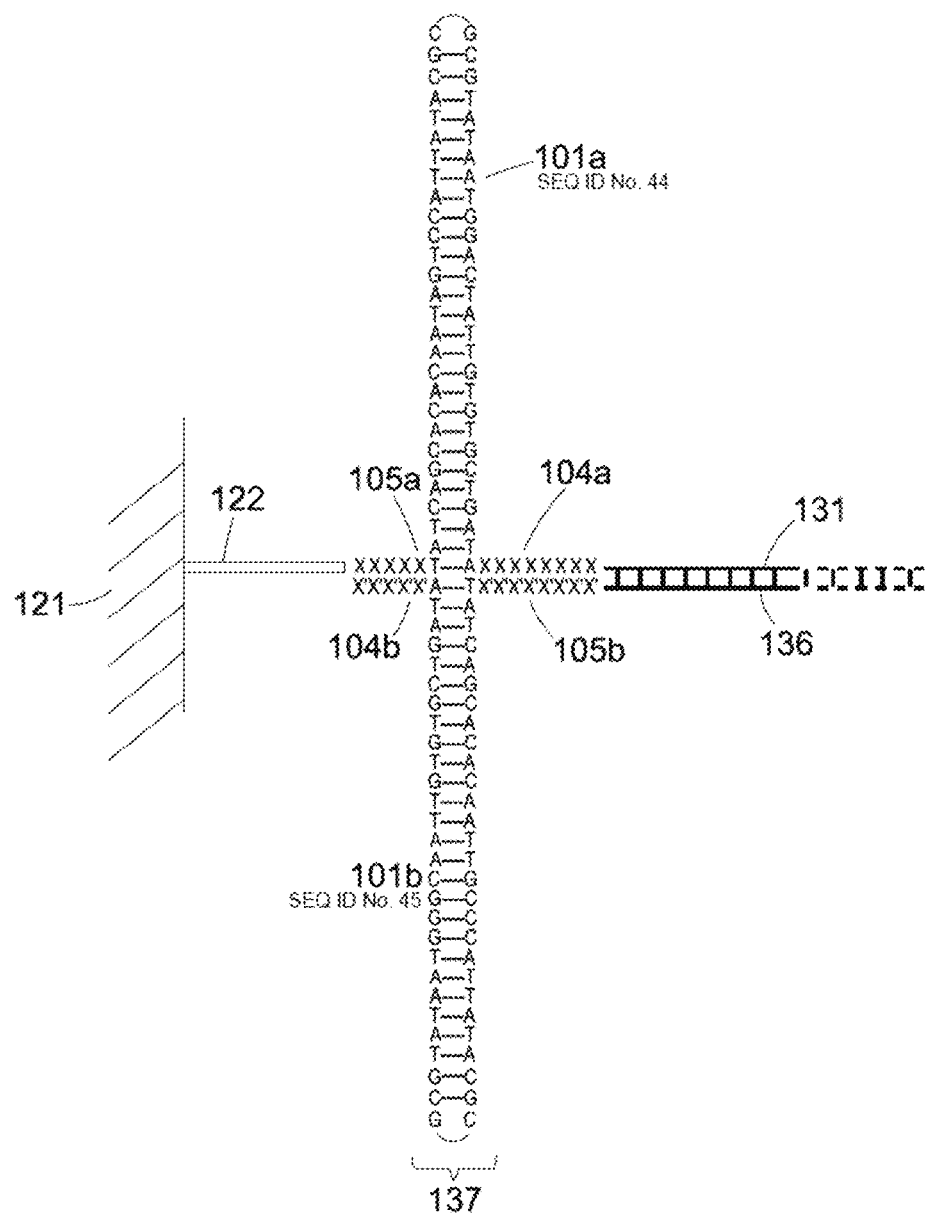
FIG. 11a depicts the structure of FIG. 10 once template-dependent extension has taken place. The first strand (133) has been extended and the second complementary strand (136) has been synthesised. The extension of the second strand (136) includes using the first portion of the protelomerase target sequence (101a—SEQ ID No. 44) and the flanking regions (104a and 105a) as a template. This results in the synthesis of complementary sequence in the second strand (136) which includes the 3' and 5' flanking regions (104b and 105b) and a second portion of the protelomerase target sequence (101b—SEQ ID No. 45). Thus, the entire protelomerase target sequence (137) is formed via the action of DNA polymerase using the immobilised oligonucleotide (100a) as a template.

As shown in FIG. 11b, despite the two portions (101a and 101b) of the protelomerase target sequence forming a duplex due to the complementary nature of the sequence of the portions, because of the palindromic nature of the protelomerase target sequence, each portion has the ability to fold into a hairpin due to internal self-complementary sequences within the portion of the target sequence. This is shown in FIG. 11a.

Where the immobilised oligonucleotide comprises a first portion of a target sequence for a protelomerase prior to extension, it may further comprise a 5' and/or a 3' flanking region thereto. The 5' and/or 3' flanking regions may have any sequence. Where the oligonucleotide contains 5' and 3' flanking regions, they are preferably not self-complementary. In other words, the 5' and 3' flanking regions are preferably sufficiently non-complementary such that the 3' region of the oligonucleotide remains available for extension under conditions promoting template-dependent extension of the oligonucleotide. In some embodiments, the 3' and/or 5' flanking regions of the oligonucleotide comprises a specific sequence, for example, sequences designed to provide a complementary sequence to sequences synthesised in the first strand or complementary second strand.

The oligonucleotide may comprise natural or modified deoxyribonucleotides and ribonucleic acids or combinations thereof. Chemical modifications may be made to the bases including but not limited to adenine, guanine, thymine, cytosine and uracil, the ribose sugar backbone and the alpha phosphate group. Examples of suitable modified deoxyribonucleotides include, locked nucleic acid (LNA), bridged nucleic acids (BNA), peptide nucleic acid (PNA), unlocked nucleic acids (UNAs) and triazole-linked deoxyribonucleotides. The use and incorporation of modified deoxyribonucleotides is particularly useful to enhance the binding of the extendable (primer) oligonucleotides to their templates and in conditions where it is desirable for nucleotide sequences at the distal end of a single DNA chain to anneal with complementary sequences at the proximal end immobilised to a surface.

The immobilised oligonucleotide can be of any suitable length. Particularly, the immobilised oligonucleotide can be between 5 and 500 bases, 5 and 400, 5 and 300, 5 and 250 or 5 and 200 bases in length. Particularly, the immobilised oligonucleotide is between 15 and 300 bases in length, more particularly between 15 and 250 bases in length or between 15 and 250, 15 and 200, 15 and 150, 15 and 100, 15 and 75, 15 and 50 bases in length. In some embodiments, the immobilised oligonucleotide is 5, 10, 15, 20, 25, 30, 35, 40, 45, 50, 55, 60, 65, 70, 75, 80, 85, 90 or 95 bases in length. In alternative embodiments, the oligonucleotide is between 30 and 100, preferably 40 and 90 bases in length.

The immobilised oligonucleotide may include the first portion of a protelomerase target sequence, or this may be included by extension of the immobilised oligonucleotide.

Figure 13:
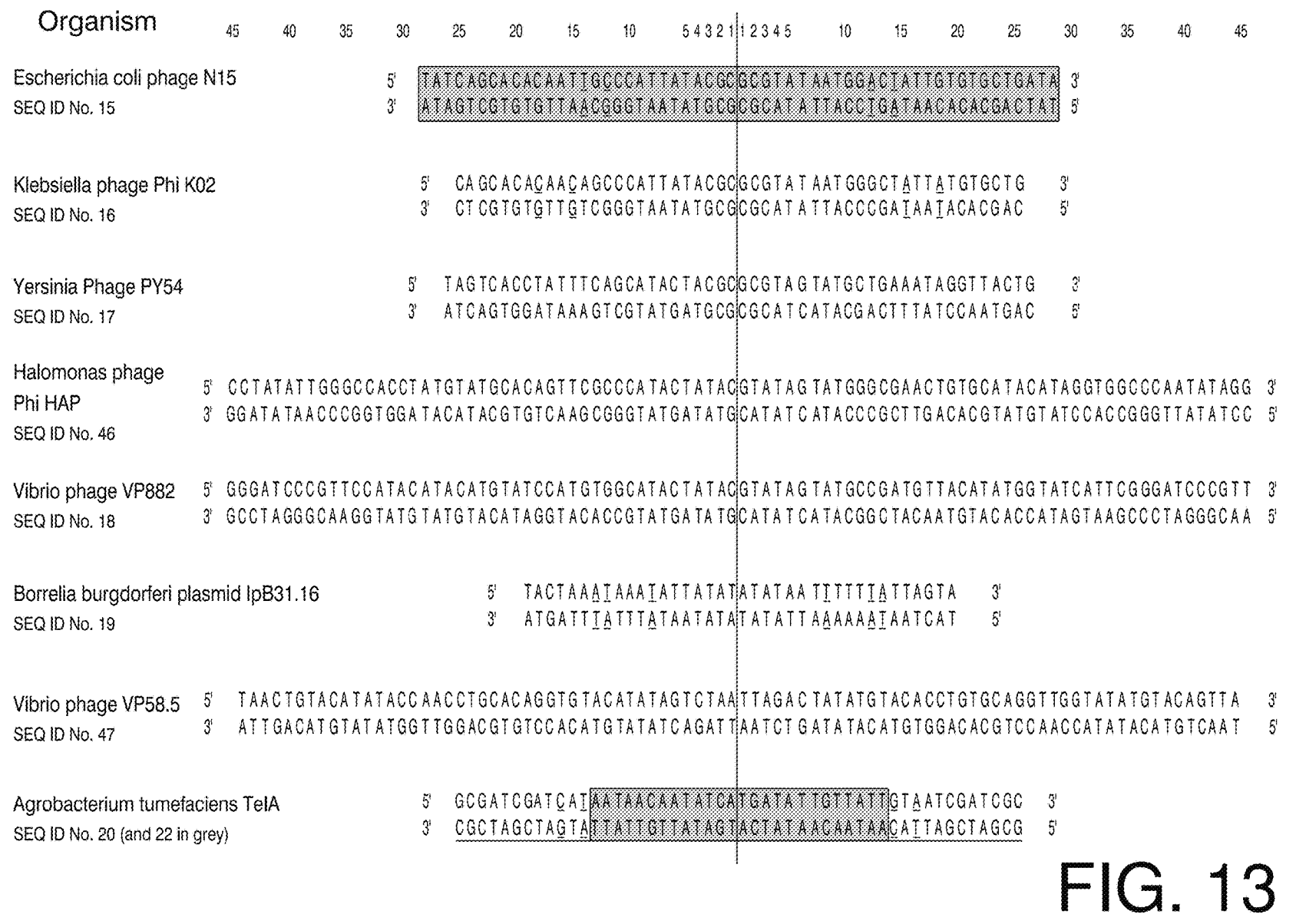

The length of the first or second portion of the protelomerase target sequence is determined by the minimum sequence recognised by the cognate protelomerase in order to bind, cleave and re-join the free ends. Several complete protelomerase target sequences are depicted in FIG. 13, and each strand represents a portion of the target sequence for the cognate protelomerase. The length of the first and second portions of the protelomerase target sequence for a cognate protelomerase may be the same or nearly so, since they are capable of annealing to form a duplex. Each portion of a protelomerase target sequence may be 20 to 100 bases in length, more particularly 30 to 100 bases in length.

The first or second portion of the protelomerase target sequence for a particular cognate protelomerase may be flanked by one or more sequences which do not form part of the protelomerase target sequence. These flanking sequences may be of any length, and may include specific sequences. These specific sequences may include a section designed to be complementary to a first template oligonucleotide, a spacer sequence, a section designed to be complementary to a sequence later included in the extended first strand of DNA or an extended further strand of DNA. The flanking sequences may include sequences which it is desired to include in the DNA product.

The oligonucleotide for immobilisation may include a section of sequence which acts as a spacer adjacent to the solid support. This spacer may be of any suitable length, and may be present to avoid any steric hindrance of the enzymes involved in the process of the invention by the sold support or the linkage entity. Ideally, the spacer is up to 250 bases in length, up to 200, 175, 150, 125, 100, 75, 50, 25, 20, 15, 10 or 5 bases in length. Should the immobilised oligonucleotide include the first portion of a protelomerase target sequence, the spacer may be included as part or all of the 5' flanking sequence (104).

The oligonucleotide for immobilisation may include a section of sequence which acts as a complementary sequence for the oligonucleotide template. Preferably, this section can be of any suitable length. The section can be between 5 and 50 bases, or between 5 and 45, 5 and 40, 5 and 35, 5 and 30, 5 and 30, 3 and 25 or 5 and 20 bases in length. Ideally, the section will be 5, 6, 7, 8, 9, 10, 11, 12, 13, 14, 15, 16, 17, 18 or 19 bases in length. It will be appreciated by those skilled in the art that the length of this section of sequence will be determined by the overlap in complementary sequence designed between the immobilised oligonucleotide and the template oligonucleotide. Furthermore, it will be appreciated that the length of this section of sequence will be determined by the DNA polymerase used and the melting temperature of the complementary sequence formed between this section of sequence and the template oligonucleotide. The same considerations and sequence length apply for each section of sequence in the extended strand that are to be used as a complementary sequence for the annealing of the template oligonucleotide.

Immobilisation to a Solid Support

The oligonucleotide may be immobilised by any means to the solid support, provided that the oligonucleotide is capable of being extended from its 3' terminus. The oligonucleotide may be directly or indirectly attached to the solid support. The means of immobilisation to the solid support is selected such that the linkage between the oligonucleotide and solid support remains stable under the conditions used for extension of the primer. Preferably, the linkage is stable under denaturing conditions. The linkage may be reversible or irreversible.

Figure 2A:
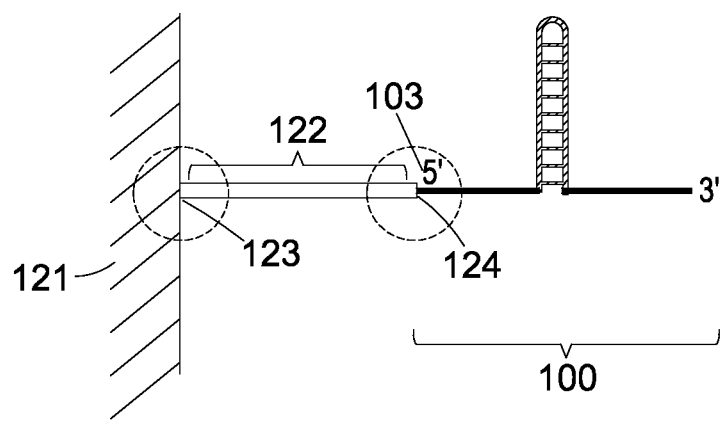
FIG. 2a depicts the use of a spacer molecule (122) which is linked to the solid support (121) and the 5' end (103) of the oligonucleotide (100) via a suitable chemical linker (123 and 124, respectively).
Figure 2B:
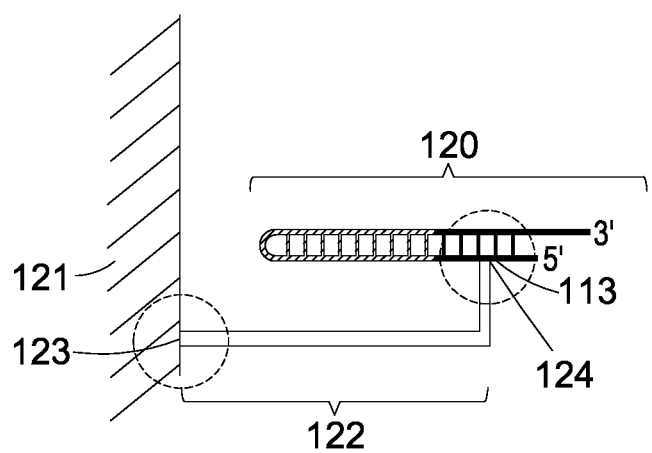
FIG. 2b depicts an alternative arrangement where the spacer molecule (122) is linked via a chemical linker to the oligonucleotide (120) 5' flanking sequence (113).

A directly attached oligonucleotide may be covalently or non-covalently bound to the solid support. Any suitable linkage chemistry may be used to covalently bind the oligonucleotide to the solid support. The oligonucleotide may be linked via its 5' terminus to the solid support (FIG. 2a). Alternatively, the oligonucleotide may be immobilised to the solid support by a linkage at an internal position (FIG. 2b). Typically, where the oligonucleotide to be immobilised includes a first portion of a protelomerase sequence, the linkage is present at a position within the oligonucleotide outside of the target sequence, such as in a spacer sequence. In such an embodiment, the linkage is preferably in the 5' flanking region of the oligonucleotide to the first portion of the target sequence for a protelomerase. However, a linkage in the 3' flanking region of the oligonucleotide to the first portion of the target sequence for a protelomerase is also possible (i.e. FIG. 2b). The linker may include a spacer to increase the distance between the solid support and the oligonucleotide. Covalent attachment may occur via conjugation with a coupling agent, via standard phosphoramidite chemistry, reverse amidite chemistry or via a 5' amino linker. Non-covalent attachment encompasses electrostatic interactions, hydrogen bonds and receptor/ligand or antibody/antigen coupling. An example of a non-covalent attachment is the biotin/streptavidin system. The solid support may be coated with streptavidin to attach a biotinylated oligonucleotide.

The spacer may be a molecule comprising for example a carbon chain consisting of multiple methylene bridges or ethylene glycol units. Spacer length in terms of the number of both carbon and oxygen atoms may be between about 3 and about 20, between about 3 and about 15 and optimally between about 5 and about 10, and typically at least 3 atoms.

Typically, a plurality of oligonucleotides will be immobilised to the solid support, permitting multiple independent synthesis reactions in parallel on a single solid support. The solid support may comprise a density of at least $10^3$, at least $10^6$, at least $10^9$, at least $10^{12}$ or at least $10^{15}$ immobilised oligonucleotides per square millimetre. The preferred density is between $10^9$ and $10^{12}$ immobilised oligonucleotides per square millimetre depending on the product to be synthesised. In addition to considerations relating to the density it is also important that the immobilised oligonucleotides are evenly distributed on the surface of the solid support to prevent unwanted intermolecular interactions and steric hindrance which inhibits oligonucleotide synthesis. Methods of ensuring even distribution of oligonucleotides on a solid surface are known in the art.

The oligonucleotides are typically attached to the solid support in the form of an array. The construction of oligonucleotide arrays is well-known in the art. The oligonucleotides may be formed on the solid support by drop deposition or inkjet technology or pre-synthesised oligonucleotides may be deposited on the array and coupled at the desired location.

The solid support according to the invention is any surface to which the oligonucleotide to be extended may be attached, bonded, coupled or tethered. Examples of solid supports include plates, beads, microbeads, hybridisation chips, membranes, crystals and ceramics. Examples of solid support materials include glass, plastics, synthetic polymers, nitrocellulose, nylon, ceramics, metals, resins, gels and membranes.

Extension of the Immobilised Oligonucleotide

The immobilised oligonucleotide is extended by use of a series of template oligonucleotides which overlap in sequence to form a sequence complementary to the sequence which is desired to be synthesised. In other words, the template oligonucleotides correspond to the complementary strand to the strand to be extended. The series of template oligonucleotides includes a first template oligonucleotide which comprises a complementary sequence to the immobilised oligonucleotide, typically a complementary sequence to a section in the 3' region of the immobilised oligonucleotide. The first template oligonucleotide anneals to the immobilised oligonucleotide, and includes a sequence which overlaps the 3' end of the immobilised oligonucleotide and provides a template for template-dependent extension of the immobilised oligonucleotide, which thus acts as a primer. Once template-dependent extension of the first template oligonucleotide has been performed, the first template oligonucleotide is removed. A second template oligonucleotide comprises a sequence which overlaps with the sequence of the first template oligonucleotide, and thus which is complementary to the sequence incorporated into the extended oligonucleotide using the first template oligonucleotide as template. Accordingly, the second template oligonucleotide anneals to the extended oligonucleotide, and again provides a template for further extension of the immobilised oligonucleotide. A sufficient number of further template oligonucleotides are provided so as to incorporate the full sequence desired to be synthesised into the immobilised oligonucleotide to thus produce the first DNA strand. An example of this process is depicted in FIG. 3, which shows the template oligonucleotide (130) annealing to the immobilised oligonucleotide (100a) near the 3' end (102a) at a region of complementary sequence (131). The template oligonucleotide overhangs the 3' end of the immobilised oligonucleotide and is available to act as a template for the polymerase-dependent extension of the 3' end of the immobilised oligonucleotide. The polymerase produces a complementary sequence (132) to the template oligonucleotide. The template oligonucleotide is then removed by appropriate means and further template oligonucleotides are successively added, used to direct extension and removed, leaving an extended first strand (133).

The first portion of the protelomerase target sequence may be incorporated into the first strand by template-dependent extension of the immobilised oligonucleotide with one or more template oligonucleotides. Typically, the first portion of the protelomerase target sequence will be incorporated into the first strand at a position proximal to the solid support. Suitably, the first portion of the protelomerase target sequence maybe located sufficiently distant to the solid support to minimise interference of the linkage to the solid support with cleavage of the complete protelomerase target sequence. In some embodiments, this may mean that no sequence is required between the linkage to the solid support and the first portion of the protelomerase target sequence. For example, a chemical spacer as described above may be utilised. In an alternative embodiment, the first portion of the protelomerase target sequence is separated from the linkage point to the solid support by at least 5 bases. In an alternative embodiment, the first portion of the protelomerase target sequence is separated by 5 to 250 bases, more preferably 5 to 200, 5 to 150, 5 to 100, 5 to 75, 5 to 50 bases. The first portion may be separated from the solid support by 5, 10, 15, 20 or 25 bases or any intervening length.

In some embodiments, an oligonucleotide may be extended by template-dependent extension with one or more template oligonucleotides prior to immobilisation on the solid support for further extension. Initial steps of extension prior to immobilisation may be carried out in solution.

A template oligonucleotide comprises a sequence which overlaps with at least one other template oligonucleotide in the series. The length of overlap is sufficient to allow for annealing to the corresponding complementary sequence in the extended oligonucleotide, and template-dependent extension of said oligonucleotide. The overlapping sequence is typically at least five nucleotides in length, and may be at least 10, at least 12, or more preferably at least 15 nucleotides in length. The overlapping sequence may be about 5 to about 10, about 10 to about 30, about 10 to about 25, about 10 to about 20, or about 15 to about 25 nucleotides in length. Preferably the overlapping sequence is about 5 to about 20 nucleotides in length. A template oligonucleotide is typically at least 30 nucleotides in length, and may be 30-40, 30-50, 30-60, 30-80, 30-100, 100-130, 130-160, 160-200, 100-200 or 40-60 nucleotides in length. A template oligonucleotide may be up to 200 nucleotides in length. Template oligonucleotides may be about 40 to about 50 nucleotides in length with about 5 to about 20 nucleotides of overlap.

The number of template oligonucleotides is selected according to the length of the sequence desired to be synthesised, and the typical overlaps, total lengths described herein. The length of a desired sequence to be synthesised may range from about 100 to about 150 bases for aptamers, to from about 1 kilobase to about 15 kilobases for vaccines and other therapeutic DNA products. Where the desired DNA sequence comprises one or more aptamer sequences, aptamer lengths may range from about 15 to about 20, about 20 to about 30, about 30 to about 40, about 40 to about 60, about 60 to about 100, about 100 to 150 bases or longer. The length of an aptamer sequence may be in the range of about 15 to about 150 bases. The number of template oligonucleotides required for synthesis in a process of the invention can be estimated for each product from the general formula: 2+(sequence length/30).

Preferably, one or more of the template oligonucleotides are non-extendable, so as to reduce competition between extension of the immobilised oligonucleotide using the template oligonucleotides as template, and extension of the template oligonucleotides using the immobilised oligonucleotide as template. In some embodiments, all of the template oligonucleotides are non-extendable. In other embodiments, all template oligonucleotides are extendible. The skilled person is able to vary conditions such as reagent concentrations, DNA polymerase, pH, ionic strength, types of divalent and monovalent ions, temperature, or to incorporate secondary structure destabilisers (e.g. nucleocapsid protein from HIV-1), molecular crowding agents (e.g. trehalose, dextran, DMSO, BSA or polyethylene glycol) or DNA condensing agents (e.g. multivalent cationic charged ligands) to favour extension of the immobilised oligonucleotide where extendable template oligonucleotides are used.

The immobilised oligonucleotide is incubated with the series of template oligonucleotides under conditions promoting template-dependent extension. Such conditions include the presence of at least one DNA polymerase.

Any DNA polymerase may be used. Any commercially available DNA polymerase is suitable for use in the process of the invention. Two, three, four, five or more different DNA polymerases may be used, for example one which provides a proof reading function and one or more others which do not. DNA polymerases having different mechanisms may be used e.g. strand displacement type polymerases and DNA polymerases replicating DNA by other methods. A suitable example of a DNA polymerase that does not have strand displacement activity is T4 DNA polymerase.

It is preferred that a DNA polymerase is highly stable, such that its activity is not substantially reduced by prolonged incubation under process conditions. Therefore, the enzyme preferably has a long half-life under a range of process conditions including but not limited to temperature and pH. It is also preferred that a DNA polymerase has one or more characteristics suitable for a manufacturing process. The DNA polymerase may have high fidelity, for example through having proof-reading activity. The DNA polymerase is preferred to have strand-displacing activity, since this may assist in replicating sequences with internal hairpins. Furthermore, it may be preferred that a DNA polymerase displays high processivity. It is preferred that a DNA polymerase does not display non-specific exonuclease activity.

The skilled person can determine whether or not a given DNA polymerase displays characteristics as defined above by comparison with the properties displayed by commercially available DNA polymerases, e.g. phi29, DeepVent®, *Bacillus stearothermophilus* (Bst) DNA polymerase, and the large fragment of DNA polymerase of *Bacillus smithii* (BSM) and the large fragment of *Bacillus subtilis* (BSU) DNA polymerase I. These enzymes are commercially available from several sources including New England Biolabs, Inc., Lucigen and Thermo Scientific.

Where a high processivity is referred to, this typically denotes the average number of nucleotides added by a DNA polymerase enzyme per association/dissociation with the template, i.e. the length of primer extension obtained from a single association event.

Strand displacement-type polymerases are preferred. Strand-displacement polymerases can assist extension through hairpin structures present in protelomerase target sequences. Preferred strand displacement-type polymerases are phi 29, Deep Vent®, BSU, BSM and Bst DNA polymerase I or variants of any thereof. The term "strand displacement" is used herein to describe the ability of a DNA polymerase to displace complementary strands on encountering a region of double stranded DNA during DNA synthesis. It should be understood that strand displacement amplification methods differ from PCR-based methods in that cycles of denaturation are not essential for efficient DNA amplification, as double-stranded DNA is not an obstacle to continued synthesis of new DNA strands. In contrast, PCR methods require cycles of denaturation (i.e. elevating temperature to 94 degrees centigrade or above) during the amplification process to melt double-stranded DNA and provide new single stranded templates.

A strand displacement DNA polymerase used in the method of the invention preferably has a processivity (primer extension length) of at least 20 kb, more preferably, at least 30 kb, at least 50 kb, or at least 70 kb or greater. In particularly preferred embodiments, the strand displacement DNA polymerase has a processivity that is comparable to, or greater than phi29 DNA polymerase.

A preferred type of strand displacement DNA polymerase is a rolling circle amplification (RCA) polymerase, such as phi29 DNA polymerase.

The conditions promoting template-dependent extension of the immobilised oligonucleotide are suitable to allow for its annealing to a template oligonucleotide, and include a suitable temperature and buffer. Appropriate annealing/hybridisation conditions may be selected empirically. An example of preferred annealing conditions used in the present invention include a buffer comprising 30 mM Tris-HCl pH 7.4, 30 mM KCl, 7.5 mM $MgCl_2$, 10 mM $(NH_4)_2SO_4$ and 1 mM DTT. The annealing may be carried out following denaturation by gradual cooling to the desired reaction temperature. Denaturation may assist extension by promoting displacement of a previous template oligonucleotide in favour of binding of a new template oligonucleotide. Accordingly, the process of the invention may comprise one or more steps of incubating an immobilised oligonucleotide bound to a template oligonucleotide under denaturing conditions subsequent to template-dependent extension. The process of the invention may comprise a step of incubation under denaturing conditions after each template-dependent extension of an immobilised oligonucleotide with a template oligonucleotide. Suitable denaturation conditions include chemical denaturation, such as by adjustment of pH, thermal denaturation by increased temperature, and change in ionic strength, such as by removal of cations for example by incubation in deionised water. Thermal denaturation is suitably employed in combination with a thermostable immobilisation of the oligonucleotide to be extended. A suitable pH for denaturation is pH 11, then adjusted to pH 7.5 to subsequently permit extension. The process of the invention may also comprise one or more, such as 1 to 5, preferably at least 2 steps of washing the extended primer to remove a previous template oligonucleotide prior to addition of a new template oligonucleotide. The process of the invention may comprise a washing step to remove template oligonucleotide after each template-dependent extension of a primer with a template oligonucleotide. The process of the invention may also comprise contacting the primer with each member of the series of template oligonucleotides separately or sequentially. Exemplary denaturation, washing and extension conditions are described in more detail below.

The conditions promoting template-dependent extension also comprise conditions promoting DNA polymerase activity. The conditions comprise use of any temperature allowing for DNA polymerase activity, commonly in the range of 20 to 90 degrees centigrade. A preferred temperature range may be about 20 to about 40 or about 25 to about 35 degrees centigrade.

Typically, an appropriate temperature is selected based on the temperature at which a specific DNA polymerase has optimal activity. This information is commonly available and forms part of the general knowledge of the skilled person. For example, where phi29 DNA polymerase is used, a suitable temperature range would be about 25 to about 35 degrees centigrade, preferably about 30 degrees centigrade. The skilled person would routinely be able to identify a suitable temperature for efficient amplification according to the process of the invention. For example, the process could be carried out at a range of temperatures, and yields of amplified DNA could be monitored to identify an optimal temperature range for a given DNA polymerase.

Other conditions promoting template-dependent extension of the immobilised oligonucleotide include the presence of all four dNTPs, ATP, TTP, CTP and GTP, suitable buffering agents/pH and other factors which are required for enzyme performance or stability. Suitable conditions include any conditions used to provide for activity of DNA polymerase enzymes known in the art.

For example, the pH may be within the range of 3 to 10, preferably 5 to 8 or about 7, such as about 7.5. pH may be maintained in this range by use of one or more buffering agents. Such buffers include, but are not restricted to MES, Bis-Tris, ADA, ACES, PIPES, MOBS, MOPS, MOPSO, Bis-Tris Propane, BES, TES, HEPES, DIPSO, TAPSO, Trizma, HEPPSO, POPSO, TEA, EPPS, Tricine, Gly-Gly, Bicine, HEPBS, TAPS, AMPD, TABS, AMPSO, CHES, CAPSO, AMP, CAPS, CABS, phosphate, citric acid-sodium hydrogen phosphate, citric acid-sodium citrate, sodium acetate-acetic acid, imidazole and sodium carbonate-sodium bicarbonate. The reaction may also comprise salts of divalent metals such as but not limited to salts of magnesium ($Mg^{2+}$) and manganese ($Mn^{2+}$), including chlorides, acetates and sulphates. Salts of monovalent metals may also be included, such as sodium salts and potassium salts, for example potassium chloride. Other salts that may be included are ammonium salts, in particular ammonium sulphate.

Detergents may also be included. Examples of suitable detergents include Triton X-100, Tween 20 and derivatives of either thereof. Stabilising agents may also be included in the reaction. Any suitable stabilising agent may be used, in particular, bovine serum albumin (BSA) and other stabilising proteins. Reaction conditions may also be improved by adding agents that relax DNA and make template denaturation easier. Such agents include, for example, dimethyl sulphoxide (DMSO), formamide, glycerol and betaine.

It should be understood that the skilled person is able to modify and optimise amplification and incubation conditions for the process of the invention on the basis of their general knowledge. Likewise the specific concentrations of particular agents may be selected on the basis of previous examples in the art and further optimised on the basis of general knowledge. As an example, a suitable reaction buffer used in RCA-based methods in the art is 50 mM Tris-HCl, pH 7.4, 10 mM $MgCl_2$, 20 mM $(NH_4)_2SO_4$, 5% glycerol, 0.2 mM BSA, 1 mM dNTPs. A preferred reaction buffer used in the RCA amplification of the invention is 30 mM Tris-HCl, pH 7.4, 30 mM KCl, 7.5 mM $MgCl_2$, 10 mM $(NH_4)_2SO_4$, 1 mM DTT, 2 mM dNTPs. This buffer is particularly suitable for use with phi29 RCA polymerase.

The reaction conditions may also comprise use of one or more additional proteins. The DNA template may be amplified in the presence of at least one pyrophosphatase, such as Yeast Inorganic pyrophosphatase. Two, three, four, five or more different pyrophosphatases may be used. These enzymes are able to degrade pyrophosphate generated by the DNA polymerase from dNTPs during strand replication. Build-up of pyrophosphate in the reaction can cause inhibition of DNA polymerases and reduce speed and efficiency of DNA amplification. Pyrophosphatases can break down pyrophosphate into non-inhibitory phosphate. An example of a suitable pyrophosphatase for use in the process of the present invention is *Saccharomyces cerevisiae* pyrophosphatase, available commercially from New England Biolabs Inc.

Any single-stranded binding protein (SSBP) may be used in the process of the invention, to stabilise single-stranded DNA. SSBPs are essential components of living cells and participate in all processes that involve ssDNA, such as DNA replication, repair and recombination. In these processes, SSBPs bind to transiently formed ssDNA and may help stabilise ssDNA structure. An example of a suitable SSBP for use in the process of the present invention is T4 gene 32 protein, available commercially from New England Biolabs, Inc.

The washing conditions may be any suitable conditions that allow for the template oligonucleotide to be removed from the immobilised oligonucleotide and the reaction mixture. Ideally, the process of washing includes or causes a denaturation step. A suitable pH for denaturation is pH 11, such as the pH provided by washing with a solution of alkali such as sodium hydroxide (i.e. 10 mM), and then it is desirable to then adjust the conditions to pH 7.4 to subsequently permit extension, for example by using reaction buffer as a final wash solution. Any suitable washing conditions may be used.

Production of Double-Stranded DNA on the Solid Support

The process of the invention may be adapted to produce and release a double-stranded DNA from the solid support. The double-stranded DNA produced is typically a linear covalently closed double-stranded DNA. The double-stranded DNA thus is closed at both ends by hairpins where at least one hairpin comprises a portion of a target sequence for a protelomerase.

FIGS. 3*a*-3*j*, 4*a* to 4*f*, 4*g*, 4*h* and 5*a* to 5*e* show examples of processes suitable for producing double-stranded DNA.

For production of double-stranded DNA, in one embodiment, an extended first strand comprising a desired DNA sequence is synthesised as discussed above, and this extended first strand is used as a template for extension of a complementary second strand using a primer complementary to the extended first strand (terminal template oligonucleotide or reverse primer). Conditions suitable for extension of the complementary second strand may be selected from those described above for extension of the first strand. The complementary second strand is extended to include a second complementary portion of the target sequence for a protelomerase located proximal to the solid support, which can thus pair or form a duplex with the corresponding first portion of the target sequence, to create a complete target sequence for a protelomerase proximal to the solid support.

Typically, a distal protelomerase target sequence is included in the double-stranded DNA to allow for formation of a second closed end. Accordingly, the process for production of double-stranded DNA from a solid support typically comprises template-dependent extension of the first strand with a template oligonucleotide comprising a first portion of a target sequence for a protelomerase, typically as a final extension of the first strand. The extended first strand thus comprises a first portion of a target sequence for a protelomerase distal to said solid support. The thus extended first strand can then be used as a template for extension of a complementary second strand, typically using a reverse primer comprising a second portion of the target sequence for a protelomerase located at the distal end of the first strand. Accordingly, a complete, distal, protelomerase target sequence is incorporated in the double-stranded DNA.

The proximal and distal protelomerase target sequences may be target sequences for the same or different protelomerase target sequences, and may each be selected from any of the protelomerase target sequences discussed below. The proximal and distal protelomerase target sequences may be selected from: target sequences for bacteriophage N15 TelN of SEQ ID NO: 10 or a variant thereof, target sequences for *Agrobacterium tumefaciens* TelA of SEQ ID NO: 12 or a variant thereof, or target sequences for bacteriophage Vp58.5 gp40 of SEQ ID NO: 14 or a variant thereof. The proximal and distal target protelomerase target sequences may comprise one target sequence for bacteriophage N15 TelN of SEQ ID NO: 10 or a variant thereof and/or one target sequence of *Agrobacterium tumefaciens* TelA of SEQ ID NO: 12 or a variant thereof and/or a target sequence for bacteriophage Vp58.5 gp40 of SEQ ID NO: 14 or a variant thereof.

Figure 3A:
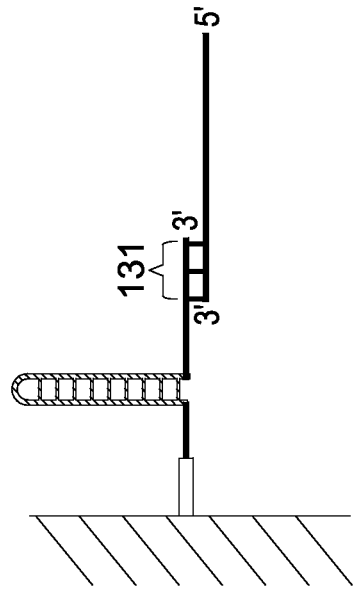
FIG. 3a shows the oligonucleotide (100a) comprising a first portion of a protelomerase target sequence (101a) immobilised via a spacer (122) to a solid support (121), in the presence of a template oligonucleotide (130).
Figure 3B:
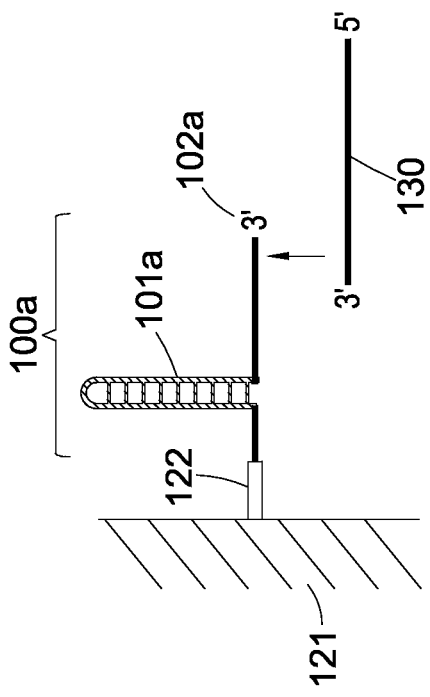
FIG. 3b shows the template oligonucleotide (130) bound to the immobilised oligonucleotide (100a) via a region of complementary sequence (131). The 5' end of the template oligonucleotide overhangs the 3' end of the immobilised oligonucleotide and can act as a template for extension of the 3' end (102a) of the immobilised oligonucleotide (100a).
Figure 3C:
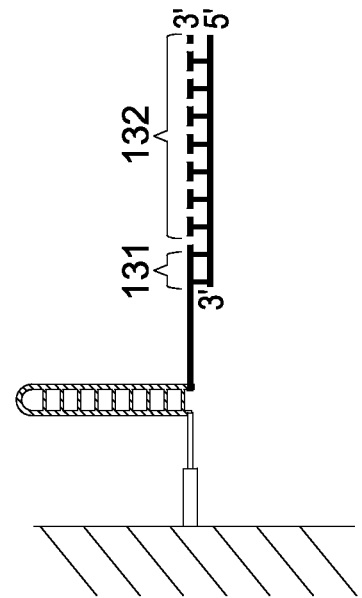
FIG. 3c shows the extension of the immobilised oligonucleotide (100a) at the 3' end (102a) once DNA polymerase (not shown) has catalysed extension with a sequence complementary to the sequence of the template oligonucleotide (130). The oligonucleotide strand, or first strand has an extended sequence (132), which is complementary to a region of the template oligonucleotide (130).
Figure 3D:
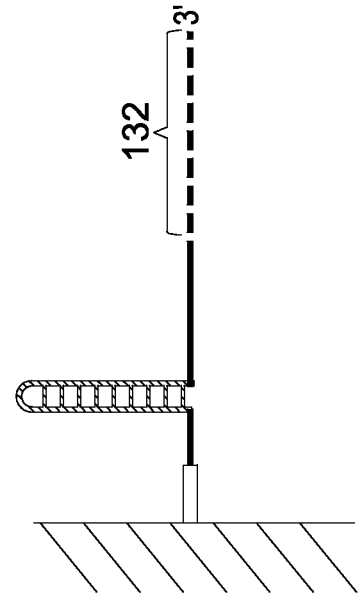
FIG. 3d shows the extended sequence (132) once the template oligonucleotide has been removed.

FIGS. 3*a* to 3*j* depict an example of such a process. The immobilised oligonucleotide (100*a*) is extended as previously described (FIGS. 3*a* to 3*e*), using a succession of template oligonucleotides (130). In FIGS. 3*f* and 3*g* a final template oligonucleotide (or reverse primer) (100*b*) is added, and this anneals near to the 3' end of the first DNA strand (133), in a region of complementary sequence (134). The final template oligonucleotide comprises a portion of a protelomerase target sequence (101*b*). DNA polymerase extends both the 3' end of the extended first strand (141) and the 3' end of the final template oligonucleotide (102*b*), creating a complete protelomerase target sequence (137*b*) at the distal, extended end of the first strand (133), and also creating a complementary second strand (136). The complementary second strand uses the first strand (133) as a template and thus a complete protelomerase target sequence (137*a*) is created proximal to the solid-support. These complete protelomerase target sequences may have the same or different sequences, using the same or different cognate protelomerase enzymes. The target sequences can be cleaved and ligated using the cognate protelomerases, releasing a double stranded, closed linear DNA from the solid support (140).

FIGS. 5*a* to 5*e* depict a similar process using an oligonucleotide immobilised at an internal nucleotide.

In an alternative embodiment, a double stranded closed linear DNA may be produced by including a suitable sequence capable of forming a hairpin in the first DNA strand. The double stranded DNA can be formed from a single strand of DNA. Such a process is depicted in FIGS. 4*a* to 4*f* and 4*g*/4*h*. For example, two sequences which are complementary to one another (181 and 184) may be incorporated at or near the distal end of the first strand in such a manner that they anneal together within the same strand to form a hairpin. Suitably, the two self-complementary sequences are neighbouring (as shown on FIGS. 4*a* to 4*f*) resulting in the formation of a hairpin. Alternatively, the two self-complementary sequences are separated by an intervening sequence region (185) which may be looped out on formation of the hairpin (as shown on FIGS. 4g and 4h). In order to produce double-stranded DNA, the 3' end of the hairpin is extended using the segment of the first strand between the solid support and the hairpin as a template, to form a complementary second segment (186) of the first strand (133). The complementary second segment (186) includes a second portion of a protelomerase target sequence (101b), thus forming a complete protelomerase target sequence (137) proximal to the solid support. This may be cleaved by the cognate protelomerase, releasing a double-stranded closed ended DNA molecule (187).

In this embodiment, one closed end is formed by the action of a protelomerase on its cognate target sequence and the other closed end is formed by including self-complementary sequences in the sequence of the first strand. The other closed end may be formed by a hairpin loop, with the loop being single stranded DNA.

In an alternative embodiment, an oligonucleotide template comprising a hairpin can be used as the terminal template oligonucleotide for the extension of the first strand. The hairpin in the template oligonucleotide can be a portion of a protelomerase target sequence or can be composed of neighbouring complementary sequences. The neighbouring complementary sequences may comprise sequences other than those of protelomerase target sequences. The template oligonucleotide anneals to the extended first strand, as shown in FIG. 5a. The 3' end of the first strand is further extended using the template oligonucleotide (FIG. 5b). The template oligonucleotide is then removed, and a hairpin is formed in the first strand due to the introduction of complementary sequences (FIG. 5c). The 3' end is then further extended using the first strand as a template, including the first portion of the protelomerase target sequence. This generates a second portion of a protelomerase target sequence, and thus a complete protelomerase target sequence proximal to the solid support (FIG. 5d). Once the cognate protelomerase is added, a closed linear DNA is produced (FIG. 5e).

Production of Single-Stranded DNA on the Solid Support

The process of the invention may be adapted to produce and release a single-stranded DNA from the solid support. The single-stranded DNA produced is typically a single-stranded circular DNA comprising a hairpin comprising a portion of a target sequence for a protelomerase. This single-stranded circular DNA is also described herein as a pinched single-stranded circular DNA (such FIG. 6e, 155 and FIG. 9, 240). Once the immobilised oligonucleotide has been extended to produce a first strand comprising the desired DNA sequence, this strand may be released as single-stranded DNA in various ways. Examples of processes to synthesize single-stranded DNA include those depicted in FIGS. 6a-6e, 7a-7e and 8a to 8f.

In one embodiment, the extended first strand is incubated under conditions promoting annealing of a sequence at its distal 3' end with a complementary sequence in the same strand located proximal to the solid support. This may be achieved by using any of the sequences in the oligonucleotide proximal to the solid support, such as the first portion of the protelomerase target sequence, the 3' flanking sequence and/or the 5' flanking sequence as sequences which are complementary to those introduced into the distal, 3' end of the first strand. An example of this is depicted in FIGS. 6a to 6e. Promoting the annealing of the distal 3' end of the extended first DNA strand (133) with its proximal end to allow for creation of a complete protelomerase target sequence proximal to the solid support may be achieved in a number of ways.

Firstly at the distal end of the extended first DNA strand, a complementary sequence to a sequence in the same strand proximal to the solid support may be covalently linked to a biotin molecule. Biotin molecules have high affinity binding to streptavidin. Thus, template-dependent extension may be used to incorporate a biotinylated nucleotide sequence at the distal end of the first strand. Where streptavidin, which has multiple biotin binding sites, is used to immobilise the oligonucleotide to the solid support, it can also be used to attract the binding of the high affinity biotin attached to the distal end of the extended primer.

Secondly, magnetic particles may be provided proximal to the solid support and also linked to a sequence the distal end of the extended DNA strand which is complementary to a sequence at the proximal end. In this case, an appropriate application of a magnetic field is used to draw together the proximal and distal ends of the first strand to allow for creation of a complete protelomerase target sequence. The annealing of complementary sequences creates a DNA loop comprising the desired DNA sequence previously incorporated in the extended first strand. Sequence(s) that are complementary to sequence(s) in the first strand proximal to the solid support are thus incorporated in the 3' distal end of the extended first strand by template-dependent extension. In this embodiment, the process of the invention may comprise template-dependent extension of the first DNA strand with a template oligonucleotide comprising a sequence corresponding to a sequence in the 3' flanking region to the first portion of the target sequence of the protelomerase located proximal to the solid support. Thus, template-dependent extension is used to incorporate at the distal 3' end of the first DNA strand a complementary sequence to the 3' flanking region to the first portion of the target sequence of the protelomerase. Alternatively, or additionally, the process of the invention may comprise template-dependent extension of the distal end of the first DNA strand to incorporate therein the second portion of the target sequence of the protelomerase which is complementary to the first portion thereof located proximal to the solid support. Optionally, a complementary sequence to the 5' flanking region to the first portion of the target sequence of the protelomerase may also be introduced at the distal end of the first DNA strand by template-dependent extension. The sequences complementary to the 3' and/or 5' flanking regions, and/or the second complementary portion of the target sequence for a protelomerase located proximal to the solid support may be introduced through one or more template oligonucleotides. The above template-dependent extension(s) may be the final step(s) of template-dependent extension of the first DNA strand.

The introduction of the above complementary sequences at the distal end of the extended first strand may produce a distal end which creates a complete target sequence for a protelomerase proximal to the solid support on annealing of the distal and proximal ends of the first strand. Alternatively, a complete target sequence for a protelomerase may be created proximal to the solid support by annealing of the distal end of the first strand to its proximal end, and subsequent template-dependent extension of the distal end using the proximal end, including the first portion of the protelomerase target sequence, as a template.

The above-defined method of creating a complete protelomerase target sequence proximal to the solid support by annealing the distal 3' end with a complementary sequence may be used for any single-stranded DNA created, including those where further hairpins may have been introduced into the first strand.

Figure 4C:
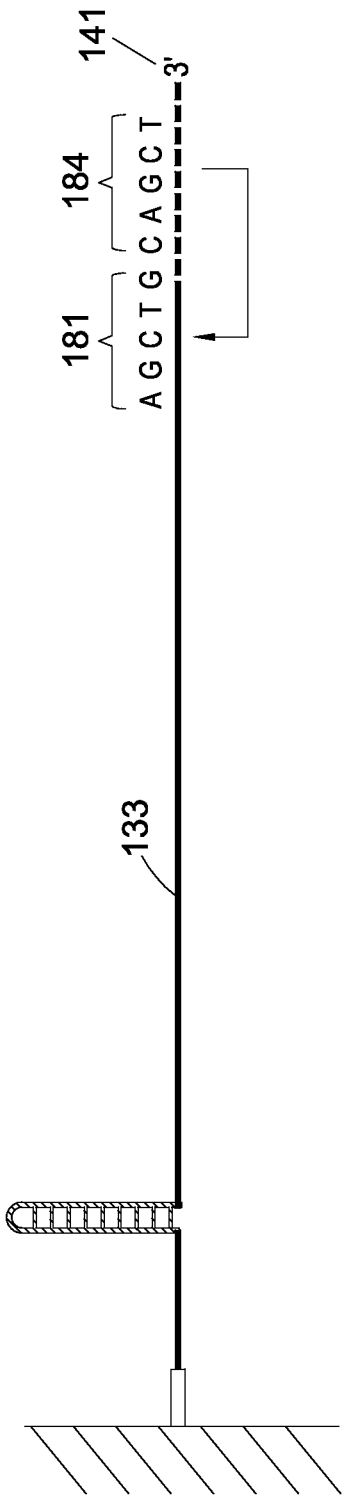
FIG. 4c shows the same structure as FIG. 4b with the template oligonucleotide (130) removed. An earlier template oligonucleotide introduced a sequence (181) in the first strand (133) which is complementary to the sequence (184) introduced by the template oligonucleotide of FIG. 4b. The first strand thus includes self-complementary sequences. The distal 3' end of the first strand (133) may loop back and the complementary sequences (181 and 184) may anneal to form a duplex. As shown here, there is no intervening single stranded sequence between the complementary sequences (181 and 184).
Figure 4D:
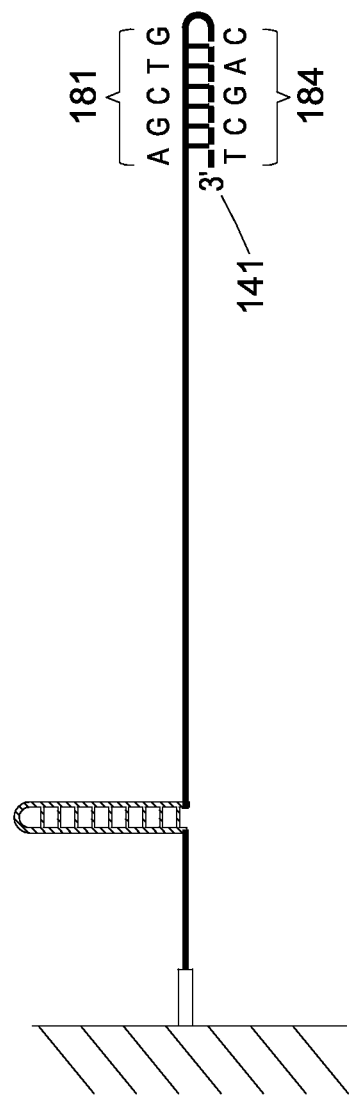
FIG. 4d depicts the structure of FIG. 4c with the two complementary sequences annealed (181 and 184).
Figure 6A:
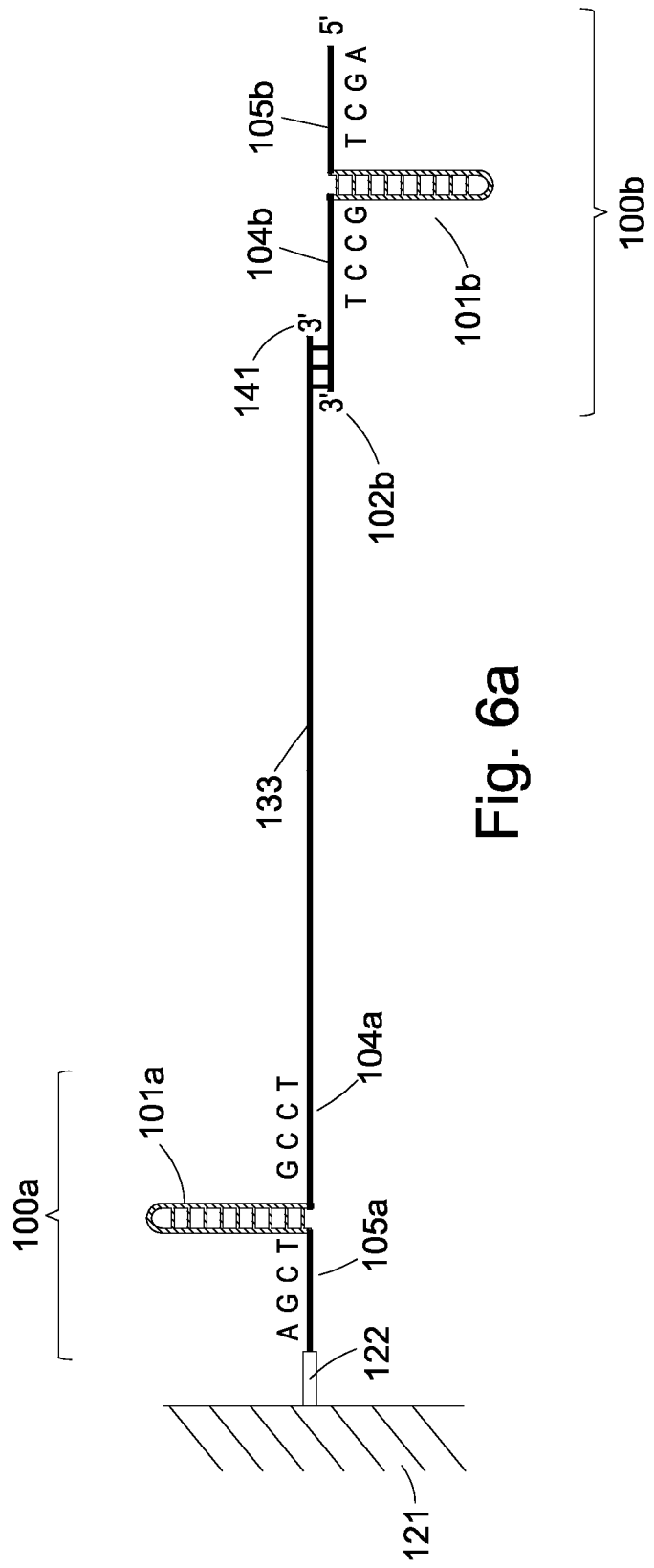
FIG. 6a shows an immobilised oligonucleotide (100a) including a first portion of a protelomerase target sequence (101a), immobilised via a spacer molecule (122) attached to a solid-support (121). The immobilised oligonucleotide has been extended via rounds of template-dependent extension, to produce a first strand (133). Shown is a second oligonucleotide (100b) including a second portion of a protelomerase target sequence (101b) bound to the first strand (133) near the 3' end (141). An exemplary sequence in the 3' and 5' flanking regions (104a/b and 105a/b) of the portions of the protelomerase target sequence (101a/b) is shown for each oligonucleotide (100a/b).
Figure 6D:
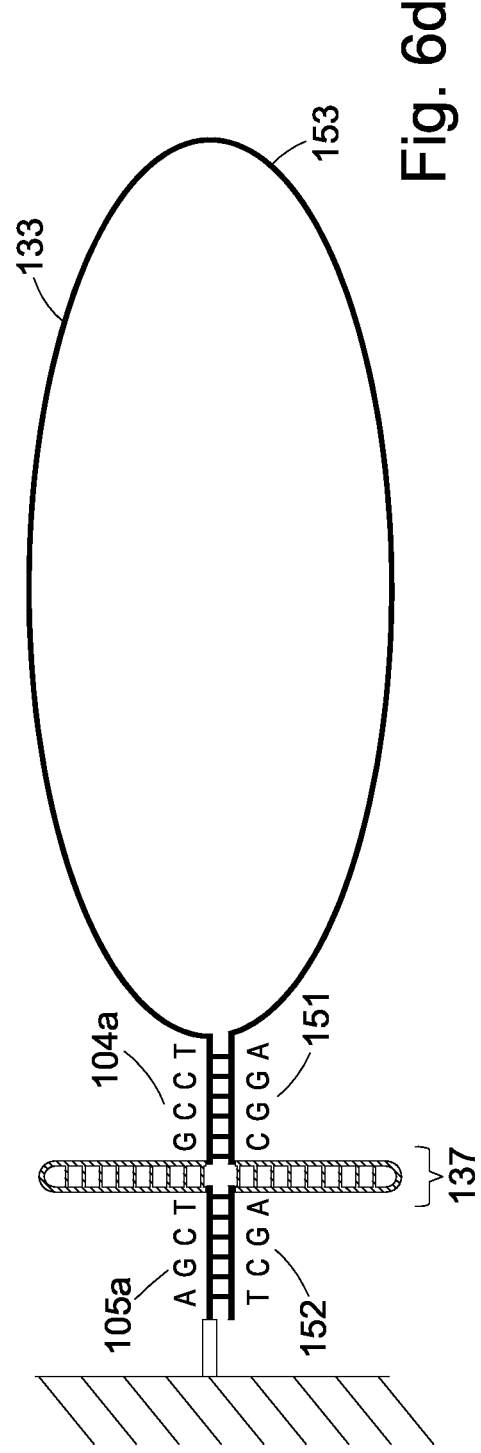
FIG. 6d depicts the annealing of the complementary flanking sequences (104a and 105a) at the proximal end of the first strand (133) with the flanking sequences (151 and 152) at the distal end of the first strand (133) to form a double stranded DNA duplex and a complete protelomerase target sequence (137). The distal portion of the protelomerase target sequence forms the second portion of the protelomerase target sequence. Since the sequence of the remaining part of the first strand (133) is not complementary, it remains in single strand form as a looped structure (153).
Figure 6E:
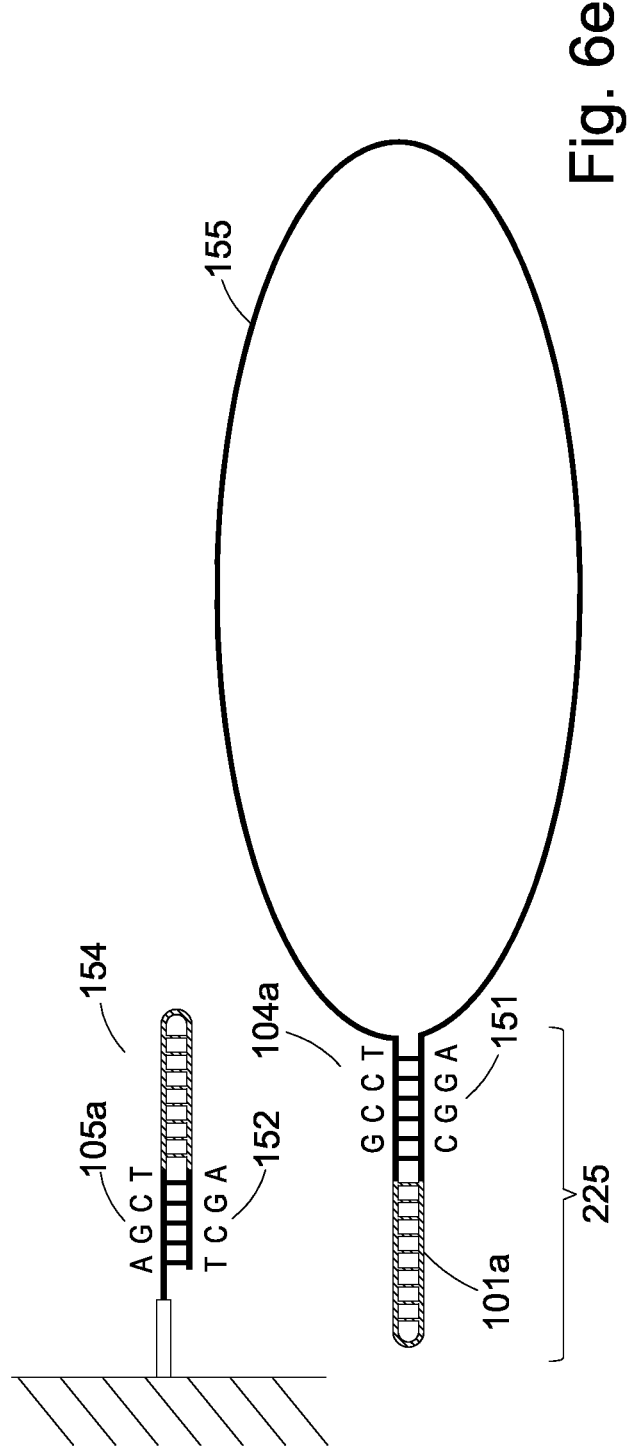
FIG. 6e depicts the result of applying protelomerase (not shown) to the structure of FIG. 6d. The entire protelomerase target sequence is cleaved and the free ends joined, releasing a covalently closed single stranded DNA (155) with a single hairpin (225) and a by-product (154) on the solid support.
Figure 7E:
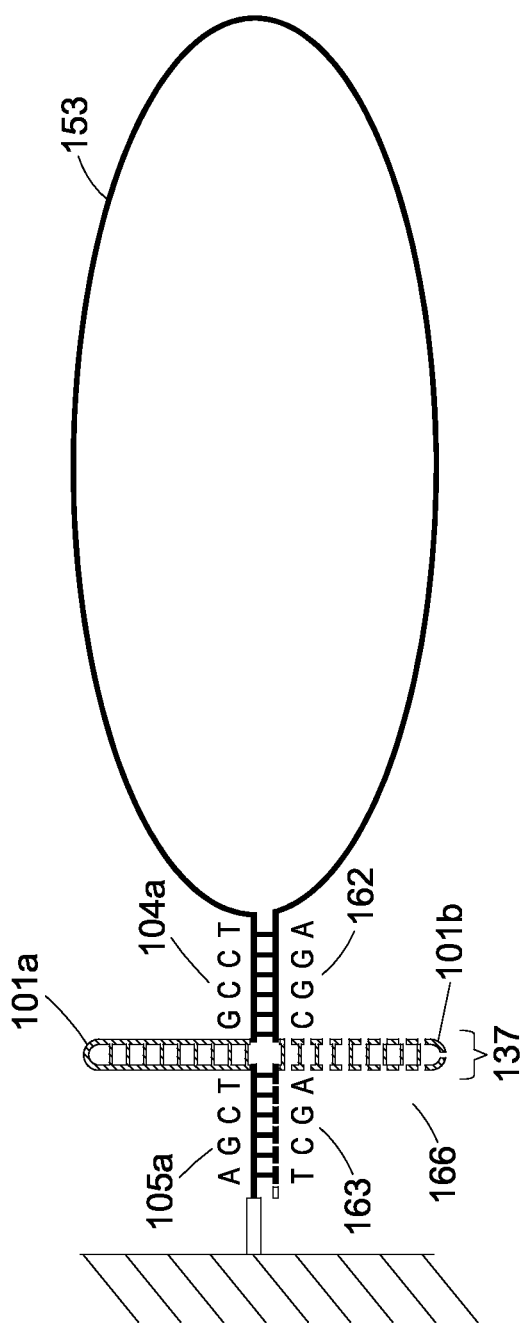
FIG. 7e depicts the structure of FIG. 7d once DNA polymerase has catalysed extension of the 3' end (141) of the first strand (133) to produce a complementary sequence (166—dashed lines) using the oligonucleotide (100a) as a template, to produce a second portion of a protelomerase target sequence (101b). An entire protelomerase structure is constructed (137). Note that this structure is identical to that of FIG. 6d, and that the structure of the products produced when protelomerase is applied will be the same as shown in FIG. 6e.
Figure 9:
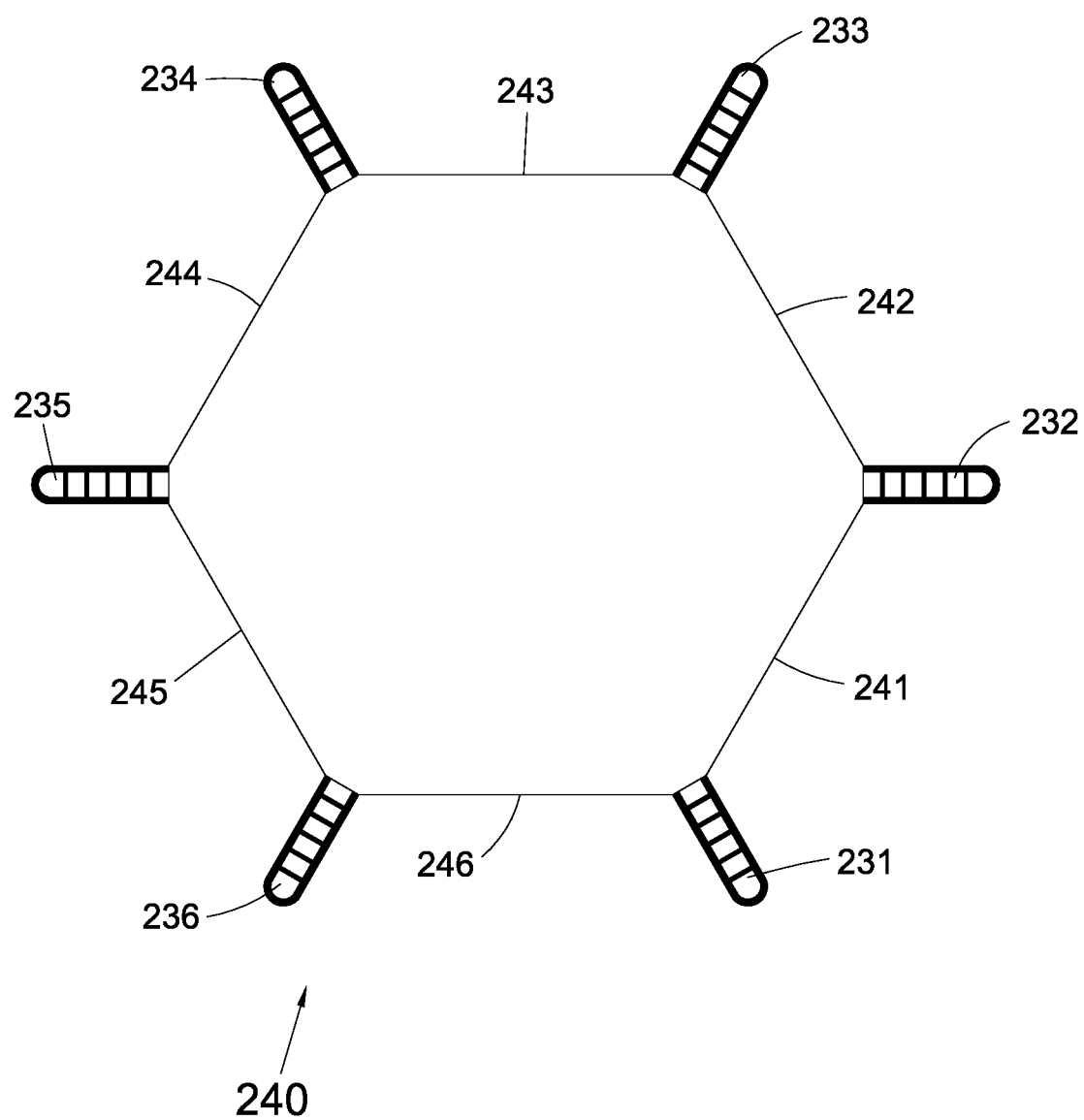
FIG. 9 depicts an exemplary structure of a single-stranded DNA (240) which can be synthesised according to the method of the present invention. This structure is a single strand of DNA, including single stranded segments (241 to 246) separated by hairpin structures (231 to 236). The hairpins can be introduced according to any method of the present invention.

In another embodiment, the extended first strand is used to create a single-stranded circular DNA comprising two or more hairpins, at least one of which comprises a portion of a target sequence for a protelomerase. The hairpins may be located at any point around the circle, but if two are present, they are typically located on opposing sides of the single stranded circular DNA (FIG. 8f, 177). In order to introduce one or more hairpins on the extended DNA strand, a hairpin or the means to make a hairpin, i.e. a complete protelomerase target sequence, may be incorporated into the distal end of the first strand, i.e. at the 3' end of the first strand. Once this hairpin, or the means to make the hairpin, has been introduced, extension of the first DNA strand may continue. The hairpin at the distal end of the first strand may be formed by the incorporation of a complete protelomerase target sequence, as depicted in FIG. 8b, or from another suitable sequence capable of forming a hairpin, as depicted in FIG. 4c. A mixture of both techniques may be used to make a closed single stranded DNA with multiple hairpins.

If a hairpin is introduced using internal self-complementary sequences, an intervening section of single stranded DNA can be created. This is depicted in FIG. 4h. For example, two sequences which are complementary to one another (181 and 184) may be incorporated at the distal end of the first strand in such a manner that they anneal together within the same strand to form a hairpin. Suitably, the two self-complementary sequences are separated by an intervening sequence region (185) which is looped out on formation of the hairpin, forming the single-stranded DNA section. This hairpin loop may comprise a desired sequence such as an aptamer or sequence for expression. Thus, the loop may be of any suitable length. It is preferred that the loop is up to 500 bases, or up to 400 bases, up to 300 bases or up to 250 bases in length. Ideally, for applications such as shorter aptamers, the loop may be between 10 and 100 bases, i.e. between 10 and 90, 10 and 80, 10 and 70, 10 and 60 or 10 and 50 bases. The loop may be 10, 15, 20, 25, 30, 35, 40, 45, 50, 55 or 60 bases in length. Alternatively, the loop (185) may contain a minimal amount of nucleic acid residues. The 3' end of the hairpin can be extended as a second segment of the first DNA strand using the first segment of the first strand as a template or by using of a series of template oligonucleotides forming a sequence that is non-complementary to at least a portion of the first segment of the first strand.

Alternatively, a complete protelomerase target sequence can be introduced at the distal end of the first DNA strand. A complete protelomerase target sequence may be introduced as discussed previously, using a template oligonucleotide comprising a portion of the protelomerase target sequence, such as those depicted in FIGS. 1a and 1c (100 and 120).

In this means of generating an introduced hairpin at the distal end of the first strand, a first portion of a protelomerase target sequence is introduced in the extended first strand distal to the solid support, typically in a template-dependent extension of the first strand. The thus extended first strand is then annealed to a template oligonucleotide comprising a portion of a target sequence for a protelomerase located at the distal end of the extended first strand, to thereby create a complete target sequence for a protelomerase once polymerase-mediated extension has taken place. The template oligonucleotide comprising the portion of the target sequence for a protelomerase is then extended as a second segment of the first DNA strand. This complete protelomerase target sequence at the distal end or 3' end of the first strand may have the same or different cognate protelomerase as the complete protelomerase target sequence proximal to the solid support.

Figure 1B:
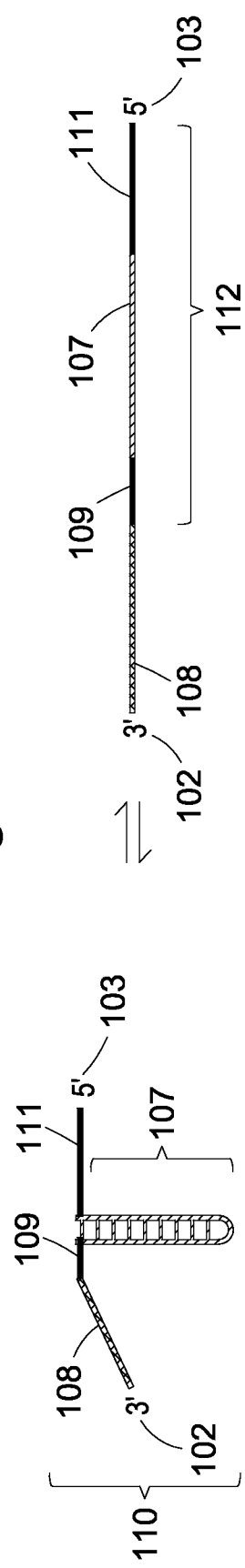
Figure 1C:
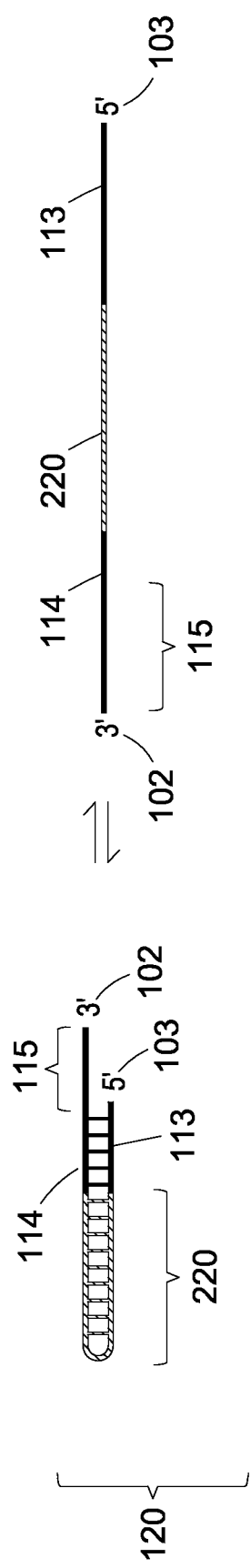

It is preferred that the template oligonucleotide used to introduce a complete protelomerase target sequence at a distal or 3' end of the first strand includes a portion of the 3' flanking sequence that is not complementary to the first segment of the first strand. The first segment of the first strand is the sequence between the solid support and the complete protelomerase target sequence. Such a template oligonucleotide (120) is shown in FIGS. 1b and 8a. Should the 3' end of this oligonucleotide be extended, the first segment of the first strand is not used as a template, but template oligonucleotides are required for polymerase-mediated extension as described previously.

Once the first hairpin or means to generate a hairpin has been included in the first strand, further extension of the 3' end of the hairpin generates a second segment of the first strand. A further hairpin or means to generate a hairpin may be introduced at the distal end of the second segment of the first strand, further extension of the 3' end of that hairpin results in extension of the third segment of the first strand, and so on. Thus, once a hairpin or means to generate a hairpin has been introduced at the distal end of the first strand, extension of the 3' end of the hairpin results in further extension of a new segment of that strand.

This process can be repeated to insert as many hairpins or means to generate the same as required.

The complete protelomerase target sequence(s) introduced into the first strand may be recognised by the same or different cognate protelomerases.

Once the complete protelomerase target sequence has been included in the first strand, it may be processed using its cognate protelomerase immediately, or at any other appropriate point in the process, including after release of the single-stranded DNA.

In an embodiment, the complete protelomerase target sequence used to create an introduced hairpin is distinct from the complete protelomerase target sequence used proximal to the solid support. In a further embodiment, each of the complete protelomerase target sequences introduced into the first strand are recognised by different cognate protelomerase enzymes.

Alternatively, the first and second portions of the protelomerase target sequence may both be incorporated into the distal end of the strand such that the complementary portions anneal together within the same strand and can form a hairpin at the distal end once cleaved by the cognate protelomerase.

In any of the above embodiments providing for further extension of the first strand via different segments, each separated by a hairpin, the extension may be carried out with a series of template oligonucleotides which overlap in sequence to form a non-complementary sequence to the earlier segment(s) of the first strand. Advantageously, this allows for inclusion of further single-stranded DNA sequences of interest in the synthesised DNA in addition to the DNA sequence of interest included in the earlier segment(s) of the first strand. The further extension of the first strand may use template oligonucleotides, extension conditions, and washing and denaturation steps as described above.

In order to form a circular single-stranded structure and release the DNA from the solid support, a complete protelomerase target sequence is required proximal to the solid support. This may be introduced using any of the means previously discussed. Advantageously, the further template-dependent extension of the first strand further comprises introduction of complementary sequence(s) in the extended first strand to sequence(s) in the first segment of the first strand proximal to the solid support, annealing of these complementary sequence(s), and creation of a complete target sequence for a protelomerase proximal to the solid support. In this way, the first extended strand creates a non-complementary single-stranded region flanked by a proximal complete protelomerase sequence at the proximal end and one or more complete protelomerase target sequence(s) or other sequence(s) capable of forming a hairpin within the extended first strand. In other words, the extended first strand may contain a complete protelomerase target sequence proximal to the solid support (the proximal complete protelomerase target sequence), which allows for release from the solid support, and also further complete protelomerase target sequences or other sequences capable of forming a hairpin, such as regions with neighbouring complementary sequences. This enables the released sequence to contain a plurality of hairpins, whilst being composed of a single strand of DNA. Due to the action of the protelomerase on the proximal complete protelomerase target sequence, the single stranded DNA has no free ends, and if the hairpins are denatured, the single stranded DNA is circular.

Where proximal and one or more distal protelomerase target sequences are used, they may be target sequences for the same or different protelomerases, and may each be selected from any of the protelomerase target sequences discussed below or shown on FIG. 13. The proximal and distal protelomerase target sequences may both be target sequences for bacteriophage N15 TelN of SEQ ID NO: 10 or a variant thereof, both be target sequences for *Agrobacterium tumefaciens* TelA of SEQ ID NO: 12 or a variant thereof or both be target sequences for bacteriophage Vp58.5 gp40 of SEQ ID NO. 14 or a variant thereof. The proximal and distal target protelomerase target sequences may comprise sequences selected from: a target sequence for bacteriophage N15 TelN of SEQ ID NO: 10 or a variant thereof, a target sequence for *Agrobacterium tumefaciens* TelA of SEQ ID NO: 12 or a variant thereof, or a target sequence for bacteriophage Vp58.5 gp40 of SEQ ID NO: 14 or a variant thereof.

As described above, sequence(s) complementary to sequences in the first strand proximal to the solid support that may be used to facilitate creation of a complete protelomerase target sequence may comprise a sequence complementary to the 3' flanking region to the first portion of a target sequence for a protelomerase located proximal to the solid support, a second complementary portion of the proximal protelomerase target sequence, and optionally a sequence complementary to the 5' flanking region to the first portion of the proximal protelomerase target sequence. The above complementary sequences may be introduced on the distal end of the extended first strand, using one or more template oligonucleotides, or a partially complementary sequence may be annealed and then extended using the first strand as template to create a complete protelomerase target sequence proximal to the solid support.

The complete protelomerase target sequences may be contacted with the cognate protelomerase at any appropriate point of the process. FIGS. 8b and 8c depicts that once the complete protelomerase target sequence is introduced in the distal end of the first strand, it is contacted with the cognate protelomerase before further extension of the strand commences. However, this could be delayed until the first strand has been further extended, as discussed below.

Following strand extension, the complete protelomerase target sequences distal (where employed, alternatively substituted for another hairpin-forming sequence) and proximal to the solid support are each contacted with a cognate protelomerase, thereby generating a single-stranded circular DNA comprising two or more hairpins, at least one of which comprises a portion of a target sequence for a protelomerase. The number of hairpins depends upon the number of complete protelomerase target sequences introduced into the extended strand and/or inclusion of other hairpin-forming sequences. The hairpins are located between the desired DNA sequence(s) introduced in the first strand, and thus the first strand is split into segments of single stranded DNA, each of which is flanked by hairpins.

In all embodiments for production of single-stranded DNA discussed above, the single-stranded DNA molecule is released from the solid support by contacting the complete protelomerase target sequence proximal to the solid support with a protelomerase, as described below.

Protelomerase Target Sequence

A protelomerase target sequence is used in accordance with the invention as a substrate for a protelomerase enzyme, to provide for release of synthesised DNA from the solid support, and/or to generate a closed end for a synthesised DNA. A protelomerase target sequence used in the invention is created from first and second portions of the target sequence which are synthesised in separate steps, either on the same DNA strand or on separate DNA strands. The process of the invention may comprise creation of a single protelomerase target sequence proximal to the solid support or creation of protelomerase target sequences both proximal and distal to said solid support.

A complete protelomerase target sequence is any DNA sequence whose presence in a DNA template provides for cleavage and religation of the template by the enzymatic activity of protelomerase to form at least one hairpin. Examples of native complete protelomerase target sequences are given in FIG. 13. A complete protelomerase target sequence may be the minimal sequence required for the action of the cognate protelomerase and may not represent the entire native recognition sequence. Where a template is double-stranded, a complete protelomerase sequence allows for its conversion into a closed linear DNA. In other words, a complete protelomerase target sequence is required for the cleavage and religation of double stranded DNA by protelomerase to form covalently closed linear DNA. A complete protelomerase target sequence thus contains the minimum amount of sequence required for target recognition, cleavage and religation of the sequence.

Typically, a protelomerase target sequence comprises any perfect palindromic sequence i.e. any double-stranded DNA sequence having two-fold rotational symmetry, also described herein as a perfect inverted repeat. As shown in FIG. 13, the protelomerase target sequences from various mesophilic bacteriophages and bacterial plasmids all share the common feature of comprising a perfect inverted repeat. The length of the perfect inverted repeat differs depending on the specific organism. In *Borrelia burgdorferi*, the perfect inverted repeat is 14 base pairs in length. In various mesophilic bacteriophages, the perfect inverted repeat is 22 base pairs or greater in length. Also, in some cases, e.g. *E. coli* N15, the central perfect inverted palindrome is flanked by inverted repeat sequences, i.e. forming part of a larger imperfect inverted palindrome.

A complete protelomerase target sequence as used in the invention preferably comprises a double stranded palindromic (perfect inverted repeat) sequence of at least 14 base pairs in length, and thus each portion of the protelomerase target sequence comprises at least 14 bases in length. As shown in FIG. 13, base pairs of the perfect inverted repeat are conserved at certain positions between different bacteriophages, while flexibility in sequence is possible at other positions. An example of a perfect inverted repeat from a protelomerase target sequence is SEQ ID NO: 22, particularly preferred for use with *Agrobacterium tumefaciens* TelA, which also is the minimum sequence required for the protelomerase TelA to bind, cleave and religate the open ends. This is shown on FIG. 13 in grey.

The perfect inverted repeat may be flanked by additional inverted repeat sequences. The flanking inverted repeats may be perfect or imperfect repeats i.e. may be completely symmetrical or partially symmetrical. The flanking inverted repeats may be contiguous with or non-contiguous with the central palindrome. The protelomerase target sequence may comprise an imperfect inverted repeat sequence which comprises a perfect inverted repeat sequence of at least 14 base pairs in length. The imperfect inverted repeat sequence may comprise a perfect inverted repeat sequence of at least 22 base pairs in length. Particularly preferred protelomerase target sequences comprise the sequences of SEQ ID NOs: 15 to 21 or variants thereof.

The sequences of SEQ ID NOs: 15 to 21 comprise perfect inverted repeat sequences, and additionally comprise flanking sequences from the relevant organisms. A protelomerase target sequence comprising the sequence of SEQ ID NO: 15 or a variant thereof is preferred for use in combination with *E. coli* N15 TelN protelomerase of SEQ ID NO: 10 and variants thereof. A protelomerase target sequence comprising the sequence of SEQ ID NO: 16 or a variant thereof is preferred for use in combination with *Klebsiella* phage Phi K02 protelomerase of SEQ ID NO: 12 and variants thereof. A protelomerase target sequence comprising the sequence of SEQ ID NO: 17 or a variant thereof is preferred for use in combination with *Yersinia* phage PY54 protelomerase of SEQ ID NO: 4 and variants thereof. A protelomerase target sequence comprising the sequence of SEQ ID NO: 18 or a variant thereof is preferred for use in combination with *Vibrio* phage VP882 protelomerase of SEQ ID NO: 8 and variants thereof. A protelomerase target sequence comprising the sequence of SEQ ID NO: 19 or a variant thereof is preferred for use in combination with a *Borrelia burgdorferi* protelomerase. A protelomerase target sequence comprising the sequence of SEQ ID NO: 20 or a variant thereof is preferred for use in combination with *Agrobacterium tumefaciens* TelA of SEQ ID NO: 12 and variants thereof. A protelomerase target sequence comprising the sequence of SEQ ID NO: 21 or a variant thereof is preferred for use in combination with *Vibrio parahaemolyticus* plasmid Vp58.5 of SEQ ID NO: 14.

Due to the presence of a central section of perfect inverted repeat section, which may be surrounded by imperfect repeat sections, the protelomerase target site may not be symmetrical. If this is the case, the site may be seen as two halves, such as the TelL and TelR sections of the protelomerase target sequence shown in FIG. 11 for protelomerase TelN. The protelomerase will still recognise the site if it is made entirely symmetrical, i.e. TelN will recognise a TelL/TelL site and a TelR/TelR site.

Variants of any of the palindrome or protelomerase target sequences described above may also be used in the invention, including homologues or mutants thereof. Mutants include truncations, substitutions or deletions with respect to the native sequence, and can thus also include fragments of the sequence. A variant sequence is any sequence whose presence in a DNA template allows for its cleavage and re-ligation to form at least one hairpin by the enzymatic activity of protelomerase, or to convert the synthesised DNA into a closed linear DNA in the case of a double-stranded DNA. This can readily be determined by use of an appropriate assay for cleavage and re-ligation of the template or for the formation of closed linear DNA. Any suitable assay described in the art may be used. An example of a suitable assay is described in Deneke et al, PNAS (2000) 97, 7721-7726. An example of a suitable assay for protelomerase activity in the process of the invention is monitoring for release of the synthesised DNA from the solid support. Preferably, a variant sequence allows for protelomerase binding and activity that is comparable to that observed with the native sequence. Examples of preferred variants of palindrome sequences described herein include truncated palindrome sequences that preserve the perfect repeat structure, and remain capable of allowing for cleavage and re-ligation of a template to form a hairpin or to allow for formation of closed linear DNA. However, variant protelomerase target sequences may be modified such that they no longer preserve a perfect palindrome, provided that they are able to act as substrates for protelomerase activity.

It should be understood that the skilled person would readily be able to identify additional suitable protelomerase target sequences for use in the invention on the basis of the structural principles outlined above. Candidate protelomerase target sequences can be screened for their ability to promote cleavage and re-ligation of a template to form a hairpin or formation of closed linear DNA using the assays for protelomerase activity described above.

The hairpin formed by the action of a protelomerase does not generally include a region of non-complementary sequence, i.e. the sequence is normally entirely complementary. With reference to FIG. 11c showing the hairpins created by TelN on the TelRL site, the entire sequence within the hairpin is complementary, and there is no loop structure at the end of the hairpin composed of non-complementary sequence. However, some structural distortion may create some strain on the pairing of bases at the tip of the hairpin, meaning that these are not available for base-pairing, despite their complementary nature. It is preferred that the hairpins formed by the protelomerase do not include any non-complementary loop section at the tip. Some "wobbles" of non-complementary bases within the length of a hairpin may not affect the structure. It is, however, preferred that the hairpin is entirely self-complementary. Complementarity describes how the bases of each polynucleotide in a sequence (5' to 3') are in a hydrogen-bonded pair with a complementary base, A to T (or U) and C to G on the anti-parallel (3' to 5') strand, which may be the same strand (internal complementary sequences) or on a different strand. It is preferred that the sequences in the hairpin are 90% complementary, preferably 91%, 92%, 93%, 94%, 95%, 96%, 98%, 99% or 100% complementary.

Formation of Hairpins and Release from Solid Support

The DNA synthesised from a solid support in accordance with the invention comprises one or more hairpins comprising a portion of a protelomerase target sequence. These may act to close the ends of the DNA in the case of a double-stranded closed linear DNA. The above hairpins are generated by contacting with a protelomerase enzyme, which also acts to release the synthesised DNA from the solid support.

A protelomerase used in the invention is any polypeptide capable of cleaving and rejoining a template comprising a cognate protelomerase target sequence in order to form a hairpin or to produce covalently closed DNA. Thus, the protelomerase has DNA cleavage and ligation functions. Enzymes having protelomerase-type activity have also been described as telomere resolvases (for example in *Borrelia burgdorferi*). If a DNA comprises a protelomerase target sequence, the enzyme can cut the DNA at this sequence and ligate the ends to create hairpins which may covalently close the DNA. Where the protelomerase target sequence in a template is proximal to a solid support, one of the resulting hairpins will remain bound to the solid support, and the template will also be released from the solid support in a form comprising a hairpin comprising a portion of a protelomerase target sequence, such as a covalently closed DNA. The requirements for protelomerase target sequences are discussed above. As also outlined above, the ability of a given polypeptide to cleave and rejoin a protelomerase target sequence can be determined using any suitable assay described in the art.

Protelomerase enzymes have been described in bacteriophages. In some lysogenic bacteria, bacteriophages exist as extrachromosomal DNA comprising linear double strands with covalently closed ends. The replication of this DNA and the maintenance of the covalently closed ends (or telomeric ends) are dependent on the activity of the enzyme, protelomerase. An example of this catalytic activity is provided by the enzyme, TelN, from the bacteriophage N15 that infects *Escherichia coli*. TelN recognises a specific nucleotide sequence; a slightly imperfect inverted palindromic structure termed TelRL comprising two halves, TelR and TelL, flanking a 22 base pair inverted perfect repeat (TelO) (see FIG. 11b). TelR and TelL comprise the closed ends of the DNA once the protelomerase has acted on the TelRL target site (FIG. 11c).

The process of the invention requires use of at least one protelomerase. The process of the invention may comprise use of more than one protelomerase, such as two, three, four, five or more different protelomerases. Examples of suitable protelomerases include those from bacteriophages such as phiHAP-1 from *Halomonas aquamarine* (SEQ ID NO: 2), PY54 from *Yersinia enterolytica* (SEQ ID NO:4), phiK02 from *Klebsiella oxytoca* (SEQ ID NO:6) and VP882 from *Vibrio* sp. (SEQ ID NO: 8), N15 from *Escherichia coli* (SEQ ID NO:10), *Agrobacterium tumefaciens* TelA (SEQ ID NO:12), Vp58.5 from *Vibrio parahaemolyticus* (SEQ ID NO:14) or variants of any thereof. Use of *E. coli* bacteriophage N15 protelomerase (SEQ ID NO: 10) or a variant thereof, *Vibrio parahaemolyticus* bacteriophage Vp58.5 gp40 (SEQ ID NO: 14) or a variant thereof and/or *Agrobacterium tumefaciens* TelA (SEQ ID NO: 12) or a variant thereof is particularly preferred.

Variants of SEQ ID NOs: 2, 4, 6, 8, 10, 12 and 14 include homologues or mutants thereof. Mutants include truncations, substitutions or deletions with respect to the native sequence. A variant must cleave and religate (forming a hairpin) or produce closed linear DNA from a template comprising a protelomerase target sequence as described above.

Any homologues of DNA polymerases or protelomerases mentioned herein are typically a functional homologue and are typically at least 40% homologous to the relevant region of the native protein. Homology can be measured using known methods. For example the UWGCG Package provides the BESTFIT program which can be used to calculate homology (for example used on its default settings) (Devereux et al (1984) Nucleic Acids Research 12, 387-395). The PILEUP and BLAST algorithms can be used to calculate homology or line up sequences (typically on their default settings), for example as described in Altschul S. F. (1993) J Mol Evol 36:290-300; Altschul, S, F et al (1990) J Mol Biol 215:403-10. Software for performing BLAST analyses is publicly available through the National Center for Biotechnology Information (http://www.ncbi.nlm.nih.gov/).

The BLAST algorithm performs a statistical analysis of the similarity between two sequences; see e.g., Karlin and Altschul (1993) Proc. Natl. Acad. Sci. USA 90: 5873-5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

A variant polypeptide comprises (or consists of) sequence which has at least 40% identity to the native protein. In preferred embodiments, a variant sequence may be at least 55%, 65%, 70%, 75%, 80%, 85%, 90% and more preferably at least 95%, 97% or 99% homologous to a particular region of the native protein over at least 20, preferably at least 30, for instance at least 40, 60, 100, 200, 300, 400 or more contiguous amino acids, or even over the entire sequence of the variant. Alternatively, the variant sequence may be at least 55%, 65%, 70%, 75%, 80%, 85%, 90% and more preferably at least 95%, 97% or 99% homologous to fulllength native protein. Typically the variant sequence differs from the relevant region of the native protein by at least, or less than, 2, 5, 10, 20, 40, 50 or 60 mutations (each of which can be substitutions, insertions or deletions). A variant sequence of the invention may have a percentage identity with a particular region of the full-length native protein which is the same as any of the specific percentage homology values (i.e. it may have at least 40%, 55%, 80% or 90% and more preferably at least 95%, 97% or 99% identity) across any of the lengths of sequence mentioned above.

Variants of the native protein also include truncations. Any truncation may be used so long as the variant is still able to produce closed linear DNA as described above. Truncations will typically be made to remove sequences that are non-essential for catalytic activity and/or do not affect conformation of the folded protein, in particular folding of the active site. Truncations may also be selected to improve solubility of the protelomerase polypeptide. Appropriate truncations can routinely be identified by systematic truncation of sequences of varying length from the N- or C-terminus.

Variants of the native protein further include mutants which have one or more, for example, 2, 3, 4, 5 to 10, 10 to 20, 20 to 40 or more, amino acid insertions, substitutions or deletions with respect to a particular region of the native protein. Deletions and insertions are made preferably outside of the catalytic domain. Insertions are typically made at the N- or C-terminal ends of a sequence derived from the native protein, for example for the purposes of recombinant expression. Substitutions are also typically made in regions that are non-essential for catalytic activity and/or do not affect conformation of the folded protein. Such substitutions may be made to improve solubility or other characteristics of the enzyme. Although not generally preferred, substitutions may also be made in the active site or in the second sphere, i.e. residues which affect or contact the position or orientation of one or more of the amino acids in the active site. These substitutions may be made to improve catalytic properties.

Substitutions preferably introduce one or more conservative changes, which replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative change may introduce another amino acid that is aromatic or aliphatic in the place of a pre-existing aromatic or aliphatic amino acid. Conservative amino acid changes are well known in the art and may be selected in accordance with the properties of the 20 main amino acids as defined in Table A.

TABLE A

Chemical properties of amino acids

| Ala | aliphatic, hydrophobic, neutral | Met | hydrophobic, neutral |
| --- | --- | --- | --- |
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged(+) | Trp | aromatic, hydrophobic, neutral |
| Leu | aliphatic, hydrophobic, neutral | Tyr | aromatic, polar, hydrophobic |

It is particularly preferred that the variant is able to cleave and religate, release from a solid support or produce covalently closed DNA as described above with an efficiency that is comparable to, or the same as the native protein.

The DNA synthesised on the solid support is incubated with at least one protelomerase under conditions promoting protelomerase activity. In other words, the conditions promote the cleavage and religation of DNA comprising a protelomerase target sequence to form DNA comprising one or more hairpins comprising portions of the protelomerase target sequence, such as a covalently closed DNA with hairpin ends. Conditions promoting protelomerase activity comprise use of any temperature allowing for protelomerase activity, commonly in the range of 20 to 90 degrees centigrade. The temperature may preferably be in a range of 25 to 40 degrees centigrade, such as about 25 to about 35 degrees centigrade, or about 30 degrees centigrade. Appropriate temperatures for a specific protelomerase may be selected according to the principles outlined above in relation to temperature conditions for DNA polymerases. A suitable temperature for use with E. coli bacteriophage TelN protelomerase of SEQ ID NO: 10 is about 25 to about 35 degrees centigrade, such as about 30 degrees centigrade.

Conditions promoting protelomerase activity also comprise the presence of suitable buffering agents/pH and other factors which are required for enzyme performance or stability. Suitable conditions include any conditions used to provide for activity of protelomerase enzymes known in the art. For example, where E. coli bacteriophage TelN protelomerase is used, a suitable buffer may be 30 mM Tris-HCl pH 7.4, 30 mM KCl, 7.5 mM $MgCl_2$, 10 mM $(NH_4)_2SO_4$ and 1 mM DTT, which may be diluted 2-8 fold depending on the concentration of the protelomerase used. Agents and conditions to maintain optimal activity and stability may also be selected from those listed for DNA polymerases.

Where proximal and distal protelomerase target sequences are created which are target sequences for different protelomerases, the distal protelomerase target sequence may be contacted with its cognate protelomerase to form a distal covalently closed DNA end prior to contacting of the protelomerase target sequence proximal to the solid support with its cognate protelomerase. Thus, the distal end of the DNA may be closed by a protelomerase prior to extension of a second non-complementary or complementary strand, or prior to release of the DNA from the solid support. Where necessary, the reaction conditions may be changed to allow for optimal processing of two different protelomerase target sequences by their cognate protelomerases.

In some embodiments, it may be possible to use the same conditions for activity of protelomerase as are used for extension of first and second DNA strands. In other embodiments, it may be necessary to change reaction conditions where conditions used to provide optimal DNA polymerase activity lead to sub-optimal protelomerase activity. Removal of specific agents and change in reaction conditions may be achievable by filtration, dialysis and other methods known in the art. The skilled person would readily be able to identify conditions allowing for optimal DNA polymerase activity and/or protelomerase activity.

In a particularly preferred embodiment, for use in synthesis of DNA by an RCA DNA polymerase, preferably phi29, the DNA synthesis is carried out under buffer conditions substantially identical to or consisting essentially of 30 mM Tris-HCl, pH 7.4, 30 mM KCl, 7.5 mM $MgCl_2$, 10 mM $(NH_4)_2SO_4$, 1 mM DTT, 1 to 4 mM dNTPs, such as 2 mM dNTPs, at a temperature of 25 to 35 degrees centigrade, such as about 30 degrees centigrade. The processing step with protelomerase may then preferably be carried out with TelN, and/or preferably under buffer conditions substantially identical to or consisting essentially of a 2 to 8 fold dilution of the buffer used for the DNA polymerase, 30 mM Tris-HCl, pH 7.4, 30 mM KCl, 7.5 mM $MgCl_2$, 10 mM $(NH4)_2SO_4$ and 1 mM DTT at a temperature of 25 to 35 degrees centigrade, such as about 30 degrees centigrade.

All enzymes and proteins for use in the process of the invention may be produced recombinantly, for example in bacteria. Any means known to the skilled person allowing for recombinant expression may be used. A plasmid or other form of expression vector comprising a nucleic acid sequence encoding the protein of interest may be introduced into bacteria, such that they express the encoded protein. For example, for expression of SEQ ID NOs: 2, 4, 6, 8, 10, 12 or 14, the vector may comprise the sequence of SEQ ID NOs: 1, 3, 5, 7, 9, 11 or 13, respectively. The expressed protein will then typically be purified, for example by use of an affinity tag, in a sufficient quantity and provided in a form suitable for use in the process of the invention. Such methodology for recombinant protein production is routinely available to the skilled person on the basis of their general knowledge. The above discussion applies to the provision of any protein discussed herein.

Purification and Formulation of DNA

Following release of a DNA product comprising one or more hairpins from the solid support by the action of protelomerase, the process of the invention may further comprise a step of purifying the DNA product. The purification referred to above will typically be performed to remove any undesired products. Purification may be carried out by any suitable means known in the art. For example, processing may comprise phenol/chloroform nucleic acid purification or the use of a column which selectively binds nucleic acid, such as those commercially available from Qiagen. The skilled person can routinely identify suitable purification techniques for use in isolation of DNA.

Once the DNA product has been generated and purified in a sufficient quantity, the process may further comprise its formulation as a DNA composition, for example a therapeutic DNA composition. A therapeutic DNA composition will comprise a therapeutic DNA molecule of the type referred to below. Such a composition will comprise a therapeutically effective amount of the DNA in a form suitable for administration by a desired route e.g. an aerosol, an injectable composition or a formulation suitable for oral, mucosal or topical administration.

Formulation of DNA as a conventional pharmaceutical preparation may be done using standard pharmaceutical formulation chemistries and methodologies, which are available to those skilled in the art. Any pharmaceutically acceptable carrier or excipient may be used. Auxiliary substances, such as wetting or emulsifying agents, pH buffering substances and the like, may be present in the excipient or vehicle. These excipients, vehicles and auxiliary substances are generally pharmaceutical agents which may be administered without undue toxicity and which, in the case of vaccine compositions will not induce an immune response in the individual receiving the composition. A suitable carrier may be a liposome or a DNA nanoparticle. DNA nanoparticles may be created by use of compaction agents such as cationic polymers to condense the DNA into nanoparticles. DNA condensing polymers may be conjugated to peptides that act as nuclear localisation signals (NLS) to overcome intra- and extracellular barriers to DNA delivery.

Pharmaceutically acceptable excipients include, but are not limited to, liquids such as water, saline, polyethylene glycol, hyaluronic acid, glycerol and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. It is also preferred, although not required, that the preparation will contain a pharmaceutically acceptable excipient that serves as a stabilizer, particularly for peptide, protein or other like molecules if they are to be included in the composition. Examples of suitable carriers that also act as stabilizers for peptides include, without limitation, pharmaceutical grades of dextrose, sucrose, lactose, trehalose, mannitol, sorbitol, inositol, dextran, and the like. Other suitable carriers include, again without limitation, starch, cellulose, sodium or calcium phosphates, citric acid, tartaric acid, glycine, high molecular weight polyethylene glycols (PEGs), and combination thereof. A thorough discussion of pharmaceutically acceptable excipients, vehicles and auxiliary substances is available in REMINGTON'S PHARMACEUTICAL SCIENCES (Mack Pub. Co., N.J. 1991), incorporated herein by reference.

Oligonucleotides and Kits for Synthesis of DNA

The invention also provides an oligonucleotide suitable for use in the process of the invention. The oligonucleotide comprises a first portion of a target sequence for a protelomerase, flanked by 5' and 3' regions. The flanking 5' and 3' regions are preferably non-complementary.

The invention further provides an oligonucleotide of the invention immobilised to a solid support. The solid support may be any solid support as described above. The oligonucleotide may be immobilised to the solid support by any linkage or spacer as described above. The solid support typically comprises a plurality of oligonucleotides as described above.

The invention additionally provides a kit comprising an oligonucleotide of the invention and at least one further component selected from a solid support, a series of template oligonucleotides overlapping in sequence and instructions for use in a process of synthesis of DNA of the invention. The kit may comprise two or all three of the above further components. The kit may further comprise a DNA polymerase and/or a protelomerase, each selected from any of these enzymes described above. The DNA polymerase is preferably phi29 or a variant thereof. The protelomerase is preferably bacteriophage N15 TelN of SEQ ID NO: 10 or a variant thereof, bacteriophage Vp58.5 gp40 of SEQ ID NO: 14 or a variant thereof, or *Agrobacterium tumefaciens* TelA of SEQ ID NO: 12 or a variant thereof. The kit may comprise the oligonucleotide of the invention attached to a solid support.

DNA Molecules Comprising Hairpins

The invention additionally provides the single-stranded and double-stranded DNA molecules that may be synthesised using the process of the invention as products per se.

Accordingly, the invention provides a single-stranded circular DNA comprising a hairpin comprising a portion of a target sequence for a protelomerase. This product is also described herein as a pinched single-stranded circular DNA and/or IbDNA.

The invention further provides a single-stranded circular DNA comprising (at least) two hairpins, at least one of which comprises a portion of a target sequence for a protelomerase. The hairpins are typically separated from each other by single-stranded segments that are non-complementary with each other. The non-complementary single-stranded segments may each comprise at least one desired sequence, such as an aptamer sequence or sequence for expression. A different desired DNA sequence, such as a different aptamer sequence may be provided in each of the non-complementary single-stranded segments.

Preferably, the hairpin comprising a portion of a target sequence for a protelomerase comprises a portion of a target sequence for bacteriophage N15 TelN of SEQ ID NO: 10 or a variant thereof, a portion of a target sequence for bacteriophage Vp58.5 gp40 of SEQ ID NO 14 or a variant thereof or a portion of a target sequence for *Agrobacterium tumefaciens* TelA of SEQ ID NO: 12 or a variant thereof.

Where two or more hairpins comprising a portion of a target sequence for a protelomerase are present in the single-stranded circular DNA, they may each comprise a portion of a target sequence for the same protelomerase. Alternatively, each hairpin may comprise a portion of a target sequence for a different protelomerase. One hairpin may comprise a portion of a target sequence for bacteriophage N15 TelN of SEQ ID NO: 10 or a variant thereof, another hairpin a portion of a target sequence for *Agrobacterium tumefaciens* TelA of SEQ ID NO: 12 or a variant thereof and another hairpin a portion of the target sequence for bacteriophage Vp58.5 gp40 of SEQ ID NO 14 or a variant thereof.

Alternatively, the single-stranded circular DNA may comprise a hairpin that is not formed by a portion of a protelomerase target sequence, in addition to a hairpin that comprises a portion of a protelomerase target sequence. The above alternative types of hairpin may be formed by any two complementary sequence regions within the same strand which can anneal together. The loop joining the two arms of the hairpin may comprise a desired DNA sequence, such as an aptamer sequence as described herein, and thus form a hairpin loop. The single-stranded circular DNA may comprise an aptamer sequence within a hairpin and one or more aptamer sequences in non-complementary single-stranded segments either side of a hairpin. Alternatively, the DNA sequences comprising the hairpin are fully complementary and no section of sequence loops at the end of the hairpin.

The invention additionally provides a linear covalently closed double-stranded DNA closed at one end by a hairpin comprising a portion of a target sequence for a first protelomerase and at a second end by a hairpin comprising a portion of a target sequence for a second protelomerase, wherein the first and second protelomerases are different. In other words, the linear covalently closed DNA (or closed linear DNA) comprises a first hairpin comprising a portion of a target sequence for a first protelomerase and a second hairpin comprising a portion of a target sequence for a second protelomerase. The first protelomerase may be bacteriophage N15 TelN of SEQ ID NO: 10 or a variant thereof and the second protelomerase *Agrobacterium tumefaciens* TelA of SEQ ID NO: 12 or a variant thereof. Alternatively, the first and/or second protelomerase may be bacteriophage Vp58.5 gp40 of SEQ ID NO 14 or a variant thereof.

The single-stranded circular and double-stranded closed linear DNA molecules of the invention have particular utility as therapeutic agents i.e. DNA medicines which can be used to express a gene product in vivo. This is because their covalently closed structure prevents attack by enzymes such as exonucleases, leading to enhanced stability and longevity of gene expression as compared to "open" DNA molecules with exposed DNA ends. Linear double stranded open-ended cassettes have been demonstrated to be inefficient with respect to gene expression when introduced into host tissue. This has been attributed to cassette instability due to the action of exonucleases in the extracellular space.

Sequestering DNA ends inside covalently closed structures also has other advantages. The DNA ends are prevented from integrating with genomic DNA and so closed linear DNA molecules are of improved safety. Also, the closed linear structure prevents concatamerisation of DNA molecules inside host cells and thus expression levels of the gene product can be regulated in a more sensitive manner.

In addition, the single-stranded circular DNA molecules of the invention are considered by the inventors to offer advantages over linear covalently closed DNA molecules for expression, since their structure is more open and thus expected to be more readily transcribed.

The DNA molecules of the invention may include a DNA sequence (described above as the desired DNA sequence) which encodes a therapeutic product. The therapeutic product may be a DNA aptamer, a protein, a peptide, or an RNA, such as small interfering RNA. Exemplary lengths for DNA aptamers are discussed above. In order to provide for therapeutic utility, such a DNA molecule may comprise an expression cassette comprising one or more promoter or enhancer elements and a gene or other coding sequence which encodes an mRNA or protein of interest. The expression cassette may comprise a eukaryotic promoter operably linked to a sequence encoding a protein of interest, and optionally an enhancer and/or a eukaryotic transcription termination sequence.

The DNA molecules of the invention may be used for production of DNA for expression in a host cell, particularly for production of DNA vaccines. DNA vaccines typically encode a modified form of an infectious organism's DNA. DNA vaccines are administered to a subject where they then express the selected protein of the infectious organism, initiating an immune response against that protein which is typically protective. DNA vaccines may also encode a tumour antigen in a cancer immunotherapy approach. Any DNA vaccine may be used in the DNA molecules of the invention.

Also, the process of the invention may produce other types of therapeutic DNA molecules e.g. those used in gene therapy. For example, such DNA molecules can be used to express a functional gene where a subject has a genetic disorder caused by a dysfunctional version of that gene. Examples of such diseases are well known in the art.

The novel structures of the invention may also have non-medical uses including in material science, in data storage and the like.

Medical Uses

The products of the invention are particularly preferred for use in medicine, since they for example are considered to provide advantages for stability in vivo. Accordingly, the invention provides a single-stranded circular DNA of the invention, or a linear covalently closed double-stranded DNA of the invention, for use in a method for treatment of the human or animal body, or in a diagnostic method practised on the human or animal body. The invention further provides a method of treatment of the human or animal body, comprising administering a therapeutically effective amount of a single-stranded circular DNA of the invention or a linear covalently closed double-stranded DNA of the invention to a human or animal in need thereof.

In particular therapeutic aspects, the DNA molecules of the invention may be used as DNA vaccines or for gene therapy. The DNA molecules may be used to induce an immune response to an antigen of interest, typically by expression of a DNA sequence encoding the antigen. The invention thus provides a method of inducing an immune response against an antigen in a host, said method comprising administering a single-stranded circular DNA or linear covalently closed double-stranded DNA of the invention that encodes said antigen to said host in such a way that said antigen is expressed in said host and induces an immune response against said antigen. The antigen may be selected from any suitable antigen.

In other embodiments, a DNA molecule of the invention may include one or more aptamer sequences which can be used to specifically recognise target molecule(s) for therapeutic purposes. An aptamer sequence for any target molecule of interest may be included in the DNA molecule.

A DNA molecule of the invention may be formulated for therapeutic purposes as described above, and for example be provided in a suitable carrier such as a liposome or DNA nanoparticle. A pharmaceutical formulation comprising a DNA molecule of the invention can be delivered to a subject in vivo using a variety of known routes and techniques. For example, a pharmaceutical formulation can be provided as an injectable solution, suspension or emulsion and administered via parenteral, subcutaneous, epidermal, intradermal, intramuscular, intra-lymphatic, intra-arterial, intraperitoneal, or intravenous injection using a conventional needle and syringe, a microneedle and syringe or using a liquid jet injection system. The administration may be made using a patch, such as a microtine patch. Pharmaceutical formulations can also be administered topically to skin or mucosal tissue, such as nasally, intratonsillarly, intratracheally, intestinal, rectally or vaginally, or provided as a finely divided spray suitable for respiratory or pulmonary administration. Other modes of administration include oral administration, suppositories, sublingual administration, and active or passive transdermal delivery techniques.

A suitable amount of the DNA molecule to be administered may be determined empirically. Dosages for administration will depend upon a number of factors including the nature of the DNA molecule and mode of action, pharmaceutical formulation, the route of administration and the schedule and timing of the administration regime. Suitable doses of a DNA molecule described herein may be in the order of microgram (μg), milligram (mg) or up to grams (g). A single administration of the DNA molecule may be sufficient to have a beneficial effect for the patient, but it will be appreciated that it may be beneficial if the DNA molecule is administered more than once, in which case typical administration regimes may be, for example, once or twice a week for 2-4 weeks every 6 months, or once a day for a week every four to six months.

Synthesis of Novel Structures

The novel structures disclosed herein are preferably synthesised using the methods of the present invention. Alternative methods of synthesising such structures are conceivable, and include template-dependent extension using no immobilisation, or alternatively, attaching the initial oligonucleotide to a 5' tag. The template dependent extension may involve thermal cycling to replace templates in a stepwise fashion, since this allows for denaturation of the "spent" template and annealing of the fresh template to allow extension. Alternatively or additionally, the methods to make the novel structures may involve different enzymes such as helicases, i.e. *Escherichia coli* Rep and *Bacillus stearothermophilus* PcrA. Any suitable method to make these novel structures involving at least one protelomerase-derived hairpin may be used.

Downstream Amplification of a Synthetic Template

The novel structures and/or products of the process of the invention carried out on a solid support may be used as a template for further DNA amplification. This provides for a process of large-scale DNA production which can be carried out wholly in an in vitro cell-free environment without a requirement for propagation of a starting template in bacteria.

The invention thus provides an in vitro cell-free process for amplification of DNA using a single-stranded circular DNA of the invention or a linear covalently closed double-stranded DNA of the invention as a template. The above process may further comprise initial production of the DNA template in accordance with a process for production of DNA of the invention carried out on a solid support. Prior to amplification, the single stranded circular DNA of the invention may be converted to double-stranded DNA, this process requiring a non-strand displacing DNA polymerase and a ligase enzyme.

The above process using either template comprises contacting the template with at least one DNA polymerase in the presence of one or more primers under conditions promoting amplification of the template. The DNA polymerase may be selected from any described above for use in the process of production of DNA on a solid support of the invention. However, the DNA polymerase is preferably a strand-displacement type polymerase, more preferably a rolling circle amplification (RCA) polymerase. A preferred RCA polymerase is phi29 or a variant thereof.

The conditions promoting amplification of the template are typically selected from those described above for template-dependent extension of the immobilised oligonucleotide on the solid support. Where the template is a linear covalently closed double-stranded DNA, it may be incubated under denaturing conditions to form a single stranded circular DNA before or during conditions promoting amplification of the template DNA.

The primer or primers may be an oligonucleotide that hybridizes to the DNA template and generates a DNA: primer hybrid that primes a DNA synthesis reaction. The primers may be non-specific (i.e. random in sequence) or may be specific for one or more sequences comprised within the DNA template. It is preferred that the primers are of random sequence so as to allow for non-specific initiation at any site on the DNA template. This allows for high efficiency of amplification through multiple initiation reactions from each template strand. Examples of random primers are hexamers, heptamers, octamers, nonamers, decamers or sequences greater in length, for example of 12, 15, 18, 20 or 30 nucleotides in length. A random primer may be of 6 to 30, 8 to 30 or 12 to 30 nucleotides in length. Random primers are typically provided as a mix of oligonucleotides which are representative of all potential combinations of e.g. hexamers, heptamers, octamers or nonamers in the DNA template.

In other embodiments, the primers are specific. This means they have a sequence which is complementary to a sequence in the DNA template from which initiation of amplification is desired. In this embodiment, either a single primer or a pair of primers may be used to specifically amplify the DNA template to produce single stranded or double stranded DNA, respectively. In another embodiment a primer capable of specifically binding to a palindromic sequence within a protelomerase target sequence comprised within the DNA template may be used. Such a primer is capable of binding to each complementary strand of the template and thus priming amplification on both strands, so only one species of primer molecule is required per template. If the template is single-stranded, only one species of primer will be required. Where the DNA template is pinched single stranded circular DNA, a single species of primer may be used. This primer may bind to a target sequence within the single stranded DNA, or alternatively bind specifically to a portion of the protelomerase target sequence within the hairpin.

Primers may be unlabelled, or may comprise one or more labels, for example radionuclides or fluorescent dyes. Primers may also comprise chemically modified nucleotides. Primers may also comprise a portion of non-complementary spacer sequence for immobilisation to a solid support. Primer lengths/sequences may typically be selected based on temperature considerations i.e. as being able to bind to the template at the temperature used in the amplification step.

The contacting of the DNA template with the DNA polymerase and one or more primers takes place under conditions promoting annealing of primers to the DNA template. The conditions include the presence of single-stranded DNA allowing for hybridisation of the primers. The conditions also include a temperature and buffer allowing for annealing of the primer to the template. Appropriate annealing/hybridisation conditions may be selected depending on the nature of the primer. An example of preferred annealing conditions used in the present invention include a buffer 30 mM Tris-HCl pH 7.5, 20 mM KCl, 8 mM $MgCl_2$. The annealing may be carried out following denaturation by gradual cooling to the desired reaction temperature.

The above processes for amplification from a DNA template of the invention may result in amplified DNA comprising concatamers comprising repeat units of amplified DNA sequence, typically where RCA amplification is used. If the template is a single stranded DNA in which a primer is chosen from a region outside of the protelomerase target sequence, with at least one hairpin according to the present invention, the concatamer made by amplifying this structure will be multiple repeats of the single stranded DNA (which is complementary in sequence to the template DNA) with intervening portions of protelomerase target sequences. In one embodiment, the single stranded DNA is synthesised as an antisense strand, such that the concatamer forms the sense strand. If a primer for RCA amplification is chosen from within the protelomerase target sequence the resulting product will be double-stranded concatamers, since the initial strand of amplified DNA will be available for priming.

The single stranded DNA concatamers produced by amplification of the novel structures may be resolved into single units of amplified DNA comprising a desired sequence of interest by various methods. The concatamers may be resolved by one or more nucleases, such as endonucleases. In particular embodiments, a single-stranded circular DNA template may comprise endonuclease site(s) flanking (at one or both ends) a sequence of interest such as a DNA aptamer, such that the aptamer sequence can be specifically released in linear form and/or excised from the remainder of the amplified DNA sequence. The double stranded concatamers can be resolved into closed linear DNA by the action of a protelomerase.

In another embodiment, where a linear covalently closed double-stranded DNA of the invention is used as a template, protelomerase target sequences for first and second protelomerases are present in the template, such that the amplified DNA may be contacted with the first and second protelomerases to release single linear covalently closed DNA units from the amplified DNA. The first and second protelomerases are preferably selected from bacteriophage N15 TelN of SEQ ID NO: 15 or a variant thereof, *Vibrio parahaemolyticus* bacteriophage Vp58.5 gp40 (SEQ ID NO: 14) or variant thereof and/or *Agrobacterium tumefaciens* TelA of SEQ ID NO: 31 or a variant thereof.

The amplified DNA resulting from the above processes for DNA amplification may be purified and formulated as described above. The invention further provides a process for making a pharmaceutical composition comprising carrying out a process for production of a DNA or for amplification of a DNA as described above, and formulating the resulting DNA product or amplified DNA with a pharmaceutically acceptable carrier or diluent.

EXAMPLES

Example 1

Reagents
Dynabeads MyOne Streptavidin C1 (Life Technologies), NxGen Phi20 DNA polymerase (Lucigen), Protelomerase TelN produced in-house (stock concentration 20.5 µM), Exonuclease III (Enzymatics), dNTPs Mix (containing lithium salts) (Bioline), Nuclease free water (Sigma Aldrich), NaOH (Fisher Scientific), Qubit dsDNA BR (Broad Range) Assay Kit (Life Technologies), Qubit dsDNA HS (High Sensitivity) Assay Kit (Life Technologies), Safe-White Nucleic Acid Stain (NBS Biologicals), Agarose (NBS Biologicals), Oligonucleotide S1, SEQ ID No. 23, (Oligo Factory), Low Molecular Weight DNA Ladder (New England Biolabs), 10×TLG buffer reagent: 300 mM Tris HCl pH 7.4 (Sigma Aldrich), 300 mM KCl (Sigma Aldrich), 75 mM $MgCl_2$ (Sigma Aldrich), 50 mM $(NH_4)_2SO_4$ (Sigma Aldrich), nuclease free water (Sigma Aldrich)

IBA Oligonucleotides (5' to 3'):
PEGS1: BiotinC6 attached to SEQ ID No. 24, PEGS2: SEQ ID No. 25, PEGS3: SEQ ID No. 26, PEGS4: SEQ ID No. 27, PEGS5: SEQ ID No. 28, PEGS6: SEQ ID No. 29, PEGS7: SEQ ID No. 30.

Oligonucleotide Design
Oligonucleotide templates were designed to produce a covalently closed linear DNA construct comprising a 194 bp sequence, which contained the first 108 bp of the CMV promoter sequence terminated at each end with a hairpin loop comprising a portion of the protelomerase TelN target sequence (FIG. 11b). Seqbuilder (http://www.dnastar.com/t-seqbuilder.aspx) was used to design the seven oligonucleotide sequences used to construct the closed linear DNA by template-dependent primer extension.

Oligonucleotide PEGS1 (with a length of 71 bases) encodes first portion of the protelomerase TelN target sequence and has a biotin C6 modification on the 5' end, which enables it to be immobilised onto streptavidin-coated magnetic beads. Oligonucleotides PEGS2 to PEGS6 (lengths of 45 bases, 45 bases, 35 bases, 40 bases and 30 bases, respectively) collectively encode the CMV promoter sequence and act as sequential templates for extension of the first immobilised oligonucleotide, which acts as a primer. The seventh oligonucleotide (PEGS7, with a length of 74 bases) contains the second portion of the protelomerase TelN target sequence). Each oligonucleotide template contains a 15 bp overlap at its 3' end with the extending 3' end of the extending immobilized oligonucleotide.

First Extension Step in Solution
The first extension step of oligonucleotide PEGS1, using oligonucleotide PEGS2 as a template, was carried out in solution. The following reagents were combined in a 0.2 ml PCR tube: 33.5 µl nuclease free water, 5 µl 10×TLG buffer pH 7.4, 2.5 µl 100 mM dNTPs (final concentration of 500 µM), 2.5 µl 100 µM oligonucleotide 1 (final concentration of 5 µM), 5 µl 100 µl oligonucleotide 2 (final concentration of 10 µM) and 15 units Phi29 to provide a total reaction of 50 µl. The reaction was mixed and incubated at 30° C. for 30 minutes in an Innova 40 incubator without shaking (New Brunswick Scientific).

Oligonucleotide Immobilization and Extension
Aliquots of streptavidin-coated magnetic beads (30 µl per extension reaction) were placed in 1.5 ml microcentrifuge tubes and washed three times with 400 µl 1×TLG buffer (pH 7.4). A magnetic microcentrifuge rack was used to enable the buffer to be separated and removed from the beads according to the manufacturer's instructions. The beads were then resuspended in 60 µl of 1×TLG buffer and mixed with 50 µl of first extension reaction described above. The beads were incubated at room temperature, with gentle shaking (50 rpm) for one hour.

After immobilisation, the first extension reaction was removed and the beads were washed in 400 µl of 10 mM NaOH. This results in strand denaturation and allows removal of the second oligonucleotide template from the newly extended first oligonucleotide attached to the beads. Three 10 mM NaOH washes were carried out to ensure complete denaturation and full removal of the previous oligonucleotide. The beads were then washed in 400 µl of 1×TLG buffer pH 7.4. After the removal of the buffer wash, the following reagents were added to the beads for a 50 µl extension reaction: 31 µl water, 5 µl 100 mM NaOH, 5 µl oligonucleotide template 3 (final concentration of 10 µM), 5 µl 10×TLG buffer pH 7.4, 2.5 µl 100 mM dNTPs (500 µM) and 15 units of Phi29 DNA polymerase, to provide a total reaction volume of 50 µl. The reaction was mixed and incubated at 30° C. for 10 minutes without shaking. The reaction was then removed and the beads were washed three times with 400 μl 10 mM NaOH and once with 400 μl 1×TLG buffer pH 7.4.

The extension reactions were then repeated, as described above, for oligonucleotide templates PEGS4, PEGS5, PEGS6 and PEGS7. When the final oligonucleotide template (PEGS7) had been added and the first strand extension completed, the beads were washed with 10 mM NaOH to denature and remove it and allow the incorporated TelN sequence to fold and form a hairpin. The 3' end of the hairpin was used to initiate the synthesis of a complementary strand to the now complete template extended first strand. The following components were added to complete the reaction: 41.5 μl nuclease free water, 5 μl 10×TGL buffer pH 7.4, 2.5 μl 100 mM dNTPs (for a final concentration of 500 μM) and 15 units of Phi29, for a final reaction volume of 50 μl. The reaction was mixed and incubated at 30° C. for 10 minutes without shaking.

Protelomerase TelN Digestion

Following the final reaction to complete the synthesis of a double stranded extension product, the beads were washed twice with 400 μl 1×TLG buffer pH 7.4. The beads were then resuspended in 98 μl 1×TLG buffer and 2 μl protelomerase TelN (400 nM) was added to cleave the extension product from the bead surface. The reaction was incubated at 30° C. for 15 minutes. High sensitivity Qubit readings were taken before and after the TelN was added and the amount of product cleaved from the surface was 1.15 μg/ml.

Rolling Circle Amplification (RCA)

Rolling circle amplification (RCA) using Phi29 DNA polymerase was used to increase the amount of product cleaved from the bead surface. The RCA reaction was set up as follows: the TelN sequence-specific oligonucleotide S1 (30 μM) was added to the TelN digest. The reaction was heated to 95° C. for 5 minutes and then cooled to 4° C. dNTPs were then added to give final concentration of 1 mM followed by 20 units of Phi29 DNA polymerase. The reaction was incubated at 30° C. overnight.

TelN and Exonuclease III Digestion

The overnight RCA concatameric DNA product (15.1 μg/ml) was digested with 500 nM protelomerase TelN at 30° C. for 15 minutes. A 25 μl aliquot was taken from the TelN digest reaction and 20U Exonuclease III was added and incubated at 37° C. for 30 minutes. Both the TelN digest product and the TelN/ExoIII product (25 μl of each sample) were heat treated at 75° C. for one minute and then run on a 2% agarose gel at 50V with SafeWhite DNA stain.

Figure 12:
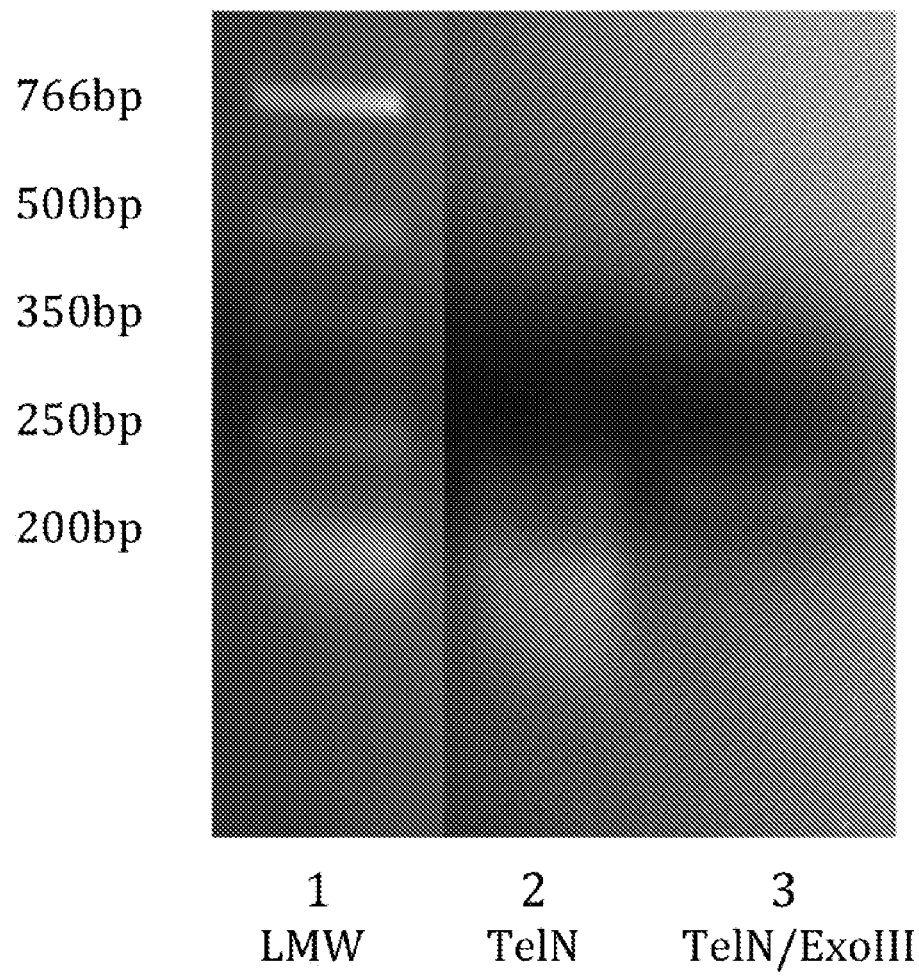
FIG. 12 shows a gel photograph of a 2% agarose gel showing the results from Example 1. The photograph both includes a molecular weight scale on the left hand side (lane 1) and an indication of the product run in the lanes at the bottom. TelN=product of rolling circle amplification (RCA) digested by TelN, TelN/ExoIII=RCA product digested by TelN and ExoIII

FIG. 12, lane 1 shows a reference DNA ladder. Lane 2 shows bands resulting from amplification (by RCA) of the covalently closed linear DNA product to produce concatamers which were then digested with protelomerase TelN. Clearly there is a band in the 200 bp region corresponding to the size of the expected product. Further treatment with exonuclease III (Lane 3) removes contaminating (open ended) fragments but leaves the product band. This demonstrates that the template extended product is of the expected size and has covalently closed ends (resistant to exonuclease action).

Example 2—Enzymatic Synthesis of Covalently Closed Linear DNA (dbDNA)

Reagents

Phusion® High Fidelity DNA polymerase (New England Biolabs), Protelomerase TelN produced in-house (stock concentration 20.5 μM), Protelomerase VP58.5 produced in house (stock concentration 21.5 μM), T5 Exonuclease (New England Biolabs), dNTPs Mix (containing lithium salts) (Bioline), Nuclease free water (Sigma Aldrich), GelRed ss/dsDNA stain (Biotium), 10% TBE precast PAGE gels (ThermoFisher), Low Range (LR) and 1 kb DNA Ladder (New England Biolabs) Isothermal Amplification Buffer ("IAB", New England Biolabs) comprising at 1×: 20 mM Tris-HCl; 10 mM (NH$_4$)$_2$SO$_4$; 50 mM KCl; 2 mM MgSO$_4$ & 0.1% Tween® 20, Buffer 4 (New England Biolabs) comprising at 1×: 50 mM potassium acetate; 20 mM Tris-acetate; 10 mM magnesium acetate & 1 mM DTT, TBE buffer from 20× stock (Thermofisher).

TABLE 1

| \multicolumn{4}{c}{Oligonucleotides (Integrated DNA Technologies)} |
|---|---|---|---|
| Name | Length | Description | Sequence (5'-3') |
| 1.120 | 79 nt | Initiating oligonucleotide primer-Alexa Fluor ® 488 fluorophore linked to the 5' end. Encodes TeIN target sequence | TATCAGCACACAATTGCCCATTATAC GCGCGTATAATGGACTATTGTGTGCT GATATGTACACTTAAGTAGTAATCAA T |
| 1.112 | 60 nt | First template oligonucleotide-3' end is a dideoxy nucleotide, preventing extension by polymerase | TGGGCTATGAACTAATGACCCCGTA *ATTGATTACTACTTAAGTGTACATAT* *CAGCACACA* |
| 1.113 | 54 nt | Second template oligonucleotide-3' end is a dideoxy nucleotide, preventing extension by polymerase | CCGTAAGTTATGTAACGCGGAACTC CATATA*TGGGCTATGAACTAATGACC* *CCG* |
| 1.114 | 60 nt | Third template oligonucleotide-3' end is a dideoxy nucleotide, preventing extension by polymerase | CTAGTAGATCTGCTAGCCGCCAGGC GGGCCATTTA*CCGTAAGTTATGTAAC* *GCGGAACTC* |
| 1.107V | 80 nt | End capping oligonucleotide containing VP58.5 target sequence-Alexa Fluor ® 488 fluorophore linked to the 5' end | AACCTGCACAGGTGTACATATAGTCT AATTAGACTATATGTACACCTGTGCA GGTTA*CTAGTAGATCTGCTAGCCGCC* *AG* |

Oligonucleotide Design

Oligonucleotide templates were designed to produce a covalently closed linear DNA construct comprising a 171 base pair sequence, terminated at one end with a hairpin loop comprising a portion of the protelomerase TelN target sequence and at the other, a hairpin loop comprising a portion of the protelomerase VP58.5 target sequence.

Oligonucleotide 1.120 (with a length of 79 nucleotides) encodes the protelomerase TelN target sequence and is modified at the 5' end with an Alexa Fluor® 488 fluorophore. Oligonucleotides 1.112, 1.113 and 1.114 (lengths of 60, 54 and 60 nucleotides respectively) collectively encode part of the CMV promoter sequence and act as sequential templates for extension of the first oligonucleotide, 1.120, which acts as a primer. The fifth oligonucleotide (1.107V, with a length of 80 nucleotides) encodes a portion of the protelomerase VP58.5 target sequence. Each oligonucleotide template contains an overlap at its 3' end with the 3' end of the extending oligonucleotide primer; these overlapping sections are marked by italics and underlined in the table.

Reaction Conditions

The extension reaction in this experiment was performed using a temperature cycling procedure. The reaction volumes were 50 µl in all cases comprising Isothermal Amplification Buffer (1× concentration), dNTPs mix (800 µM), 200 µM of each oligonucleotide (1.120, 1.112, 1.113, 1.114 and 1.107V) and 1 unit of Phusion® High Fidelity DNA polymerase (New England Biolabs)

Temperature cycling reactions were performed in a Bio-Rad C1000 Thermal Cycler under the following conditions: 2 minutes at 95° C.; 50 cycles comprising:1 minute at 95° C., 1 minute at 50° C., 1 minute at 72° C.; 10 minutes at 72° C.; 4° C. END The reaction produces an open ended double stranded DNA comprising sequences from the 5 oligonucleotides. One end of the molecule incorporates a full TelN protelomerase target sequence while the other incorporates a full VP58.5 target sequence (full sized linear product). The 5' end of each strand is labeled with an Alexa Fluor® 488 fluorophore making it visible under blue light at a wavelength of 490 nm. The product of the extension reaction when treated with protelomerases produces covalently closed linear DNA.

Protelomerase reactions were performed in the same buffer as the extension reaction—that is, the protelomerase enzyme was added directly to the cycling reaction upon its completion. Individual protelomerases were added to a final concentration of 1 µM but where both TelN and VP58.5 protelomerases were added the concentration of each was reduced to 0.5 µM. Reactions were incubated at 37° C. for 15-30 minutes, and inactivated at 75° C. for a further 10 minutes.

Gel Electrophoresis Gels in this example are all native 10% TBE PAGE gels, run at 180 volts in 1×TBE buffer. Imaging was performed with excitation at wavelength of 490 nm for fluorescently tagged molecules or at 300 nm after staining with 3 times concentrated GelRed™ DNA stain for 1 hour to image all the DNA/oligonucleotides present. Results are shown as FIGS. 14 and 15. Lane 1, FIG. 14 shows a bright band corresponding to the full sized linear product formed following the templated extension reaction. The lower bright band corresponds to unincorporated fluorescently tagged oligonucleotides, i.e. 1.107V and 1.120. The corresponding lane in FIG. 15 confirms the presence of the full sized linear product.

Lanes 2 and 3 (FIG. 15) show bands corresponding to full sized linear products cleaved and joined at one end with TelN or VP58.5 protelomerase respectively. The release of the very short hairpin protelomerase sequences from this reaction are also clearly evident in FIG. 14, Lanes 2 and 3 and confirm protelomerase activity.

Treatment of the full sized linear product with both protelomerases TelN and VP58.5 produces a covalently closed linear DNA product, dbDNA (FIG. 15, Lane 4). Confirmation of this is indicated in FIG. 15, Lane 5 which shows a single band only, corresponding to the correct size of the desired dbDNA product. All other open ended linear products have been completely hydrolysed by exonuclease T5 which was added to reactions at a concentration of 0.2 units/µl, in 1×NEB buffer 4. T5 exonuclease attacks both single and double stranded DNA with blunt or overhanging ends and from both 5' and 3' ends dbDNA is resistant to exonuclease T5, as it is circular with no free ends (5' or 3') to attack. This is further confirmed in Lane 5, FIG. 14 where, as expected, no fluorescent DNA/oligonucleotides are evident and all fluorescence is located in a band at the very bottom of the gel where it would be expected to find dNTPs. The fluorescent tags at each end of the full sized linear product have been cleaved off by the protelomerases leaving a non-fluorescent and therefore non-visible dbDNA when this imaging is used, whereas it can be seen using GelRed as shown on FIG. 15. The fluorescent hairpins released have been hydrolysed by T5 exonuclease to dNTPs.

The data confirms successful synthesis of the closed linear DNA product.

Example 3—Enzymatic Synthesis of Covalently Closed Linear DNA (dbDNA) on a Solid Surface Reagents The same reagents were used as indicated in Example 2 plus 5 nm gold nanoparticles (Cytodiagnostics).

TABLE 2

Oligonucleotides (Integrated DNA Technologies) encode the eGFP gene sequence flanked by a CMV promoter and poly-A tail, all within protelomerase TeIN target sites.

| Name | Length | Description | Sequence (5'-3') |
|---|---|---|---|
| 3.1 | 81 nt | Initiating oligonucleotide primer- two thiol groups are linked to the 5' phosphate group to allow attachment of the oligo to a surface | TATGGAAAAACGCCAGCAACGCGGCCTTTT TACGGTTCCTGGCCTTTTGCTGGCCTTTT*GC TCACATGTAGATCTTGTACA* |
| 3.2 | 200 nt | First template oligonucleotide of the series-3' end has a 3 nucleotide mismatch to its binding site, preventing extension by polymerase | *GGGCGGGGGTCGTTGGGCGGTCAGC*CAGG CGGGCCATTTACCGTAAGTTATGTAACGCG GAACTCCATATATGGGCTATGAACTAATGA CCCCGTAATTGATTACTACTTAAGTGTACAT ATCAGCACACAATAGTCCATTATACGCGCG TATAATGGGCAATTGTGTGCTGATA*TGTAC AAGATCTACATGTGAGC*TTT |

TABLE 2-continued

Oligonucleotides (Integrated DNA Technologies) encode the eGFP gene sequence flanked by a CMV promoter and poly-A tail, all within protelomerase TeIN target sites.

| Name | Length | Description | Sequence (5'-3') |
|---|---|---|---|
| 3.3 | 200 nt | Second template oligonucleotide of the series-3' end has a 3 nucleotide mismatch to its binding site, preventing extension by polymerase | *ATAATGCCAGGCGGGCCATTTACCG*TCATT GACGTCAATAGGGGGCGTACTTGGCATAT GATACACTTGATGTACTGCCAAGTGGGCAG TTTACCGTAAATACTCCACCCATTGACGTCA ATGGAAAGTCCCTATTGGCGTTACTATGGG AACATACGTCATTATTGACGTCAAT*GGGCG GGGGTCGTTGGGCGGTC*TCG |
| 3.4 | 200 nt | Third template oligonucleotide of the series-3' end has a 3 nucleotide mismatch to its binding site, preventing extension by polymerase | *GCCAAAACAAACTCCCATTGACGTC*AATGG GGTGGAGACTTGGAAATCCCCGTGAGTCA AACCGCTATCCACGCCCATTGATGTACTGCC AAAACCGCATCACCATGGTAATAGCGATGA CTAATACGTAGATGTACTGCCAAGTAGGAA AGTCCCATAAGGTCATGTACTGGGC*ATAAT GCCAGGCGGGCCATTT*AGGC |
| 3.5 | 64 nt | End capping oligonucleotide- includes sequence for TeIN loopback extension | CCATTATACGCGCGTATAATGGGCAATTGT GTGCTGATA*GCCAAAACAAACTCCCATTGA C*CAG |

Oligonucleotide Design

Oligonucleotide templates were designed to produce a covalently closed linear DNA (dbDNA) construct comprising a 525 base pair sequence, terminated at each end with hairpin loops comprising a portion of the protelomerase TelN target sequence.

Oligonucleotide 3.1 (with a length of 81 nucleotides) is modified with two thiol groups attached to the terminal 5' phosphate to allow covalent attachment to a prepared solid surface. Oligonucleotide 3.2 (with a length of 200 nucleotides) encodes the protelomerase TelN target sequence and a portion of the CMV promoter sequence, and oligonucleotides 3.3 and 3.4 (each 200 nucleotides in length) collectively encode a further portion of the CMV promoter sequence. Together, these three oligonucleotides act as sequential templates for extension of the first oligonucleotide, 3.1, which acts as a primer. The fifth oligonucleotide (3.5, with a length of 64 nucleotides) encodes a portion of the protelomerase TelN target sequence. This oligonucleotide does not contain the full protelomerase site, but rather encodes just over half—this will allow the extended strand to 'loop back' on itself to enable extension to form a double stranded oligonucleotide. The loop thus formed is the same sequence as the hairpin loop produced by successful protelomerase TelN cleavage of its target site. Each oligonucleotide template contains an overlap at its 3' end with the 3' end of the extending oligonucleotide primer (sequences underlined and italicised mark these overlapping sections). The last 3 nucleotides at the 3' end of oligonucleotides 3.2 to 3.5 are not complementary to the extending strand to prevent their unwanted extension by DNA polymerase.

Immobilization of Oligonucleotide 3.1 on 'Gold Nanoparticles'

De-protection of the thiolated oligonucleotide, and linkage of that oligonucleotide to gold nanoparticles, was performed as directed by the manufacturer's instructions for the Cytodiagnostics® 5 nm OligoREADY Gold Nanoparticle Conjugation Kit. De-protected oligonucleotide was separated from DTT using a G-25 column from GE Healthcare, and linked oligonucleotide was purified by repeated (10×) washes in ddH$_2$O in a 30 kDa spin concentrator column (Millipore) by centrifugation at 4,500 g.

Reaction Conditions

The extension reaction by thermal cycling was carried out as described in Example 2 using the oligonucleotide templates described above. However, in this experiment, the initiating oligonucleotide primer was covalently attached to a gold nanoparticle such that the extension reaction was carried out on a surface.

The reaction produces an immobilised dsDNA molecule comprising sequences from the 5 oligonucleotides. The end of the molecule proximal to the gold nanoparticle incorporates a full TelN protelomerase target sequence while the distal end incorporates a hairpin sequence identical to that produced by TelN cleavage of its target site. The product of the extension reaction when treated with TelN protelomerase is therefore a covalently closed linear DNA (dbDNA) cleaved from the gold nanoparticle.

Protelomerase TelN reactions were performed in the same buffer as the extension reaction i.e., the protelomerase enzyme was added directly to the cycling reaction upon its completion. Protelomerase was added to a final concentration of 0.5 µM. Reactions were incubated at 37° C. for 15-30 minutes, and inactivated at 75° C. for a further 10 minutes. Exonuclease T5 was added to reactions at a concentration of 0.2 units/µl, in 1×NEB buffer 4 (50 mM potassium acetate; 20 mM Tris-acetate; 10 mM magnesium acetate & 1 mM DTT).

Gel Electrophoresis

The illustrated gel in FIG. 16 is a native 10% TBE PAGE gel, run at 180 volts in 1×TBE buffer.

Imaging was performed with excitation at a wavelength of 300 nm after staining with 3 times concentrated GelRed™ DNA stain for 1 hour to image all the DNA/oligonucleotides present. As shown in FIG. 16, dbDNA can be produced by the method described in Example 2 but with the starting oligonucleotide 3.1 immobilised on a surface of a 5 nm diameter. Much of the DNA in the reaction is impeded from passing into the agarose by its fusion to the gold nanoparticle (Lane 3). However, dbDNA, when released by TelN cleavage and cleaned up by treatment with T5, runs as a single exonuclease resistant band to a position expected by its size (Lane 7).

Example 4—Synthesis of Circular Single Stranded DNA Covalently Closed by the Action of a Protelomerase This example describes the synthesis of a single stranded circular DNA containing a protelomerase target sequence (referred to as IbDNA). This structure may be exploited in the same way as doubled stranded covalently closed linear DNA but with the potential advantage that the single stranded loop is permanently open to transcription into RNA. In addition, the single stranded loop section may be designed to encode an aptamer sequence with specific molecular binding properties for diagnostic and medicinal applications.

A circular single stranded DNA has been synthesized from a 159 nucleotide long oligonucleotide encoding an aptamer sequence reported to inhibit metallo-β-lactamase enzyme activity in *Bacillus cereus* (Kim. S-K et al, 2009, *Chemical Biology & Drug Design*, 74(4), 343-348.)

The sequence of the oligonucleotide and process for conversion into a circular single stranded construct is outlined in Table 3 and FIGS. 17a to c.

TABLE 3

Sequences of IbDNA precursor oligonucleotides. Reverse complementary sequences are underlined, aptamer sequence is in italics, spacer sequences are in bold.
Supplied by Integrated DNA Technologies

| Name | Length | Description | Sequence (5'-3') |
|------|--------|-------------|------------------|
| DNA-T | 159 nt | Oligonucleotide containing a TelN target sequence, reverse complementary regions and a target sequence containing an aptamer | TACTAGTCATCTATCAGCACACA ATTGCCCATTATACGCGTATAATG GACTATTGTGTGCTGATATACTAGGC ACCACCTGCAGGAATCTACTAGGCC GCCGCAACCAAACTTGGATCGGTGC ACATGTCGAATACTAGGATTCCTGCA GGTGGTGC |
| DNA-V | 159 nt | Oligonucleotide containing a VP58.5 target sequence, reverse complementary regions and a target sequence containing an aptamer | TACTAGTCATCAACCTGCACAGG TGTACATATAGTCTAATTAGACTATA TGTACACCTGTGCAGGTTTACTAGGC ACCACCTGCAGGAATCTACTAGGCC GCCGCAACCAAACTTGGATCGGTGC ACATGTCGAATACTAGGATTCCTGCA GGTGGTGC |

A Single Oligonucleotide May be Extended and Processed to IbDNA

A 159 nt oligonucleotide consisting of a protelomerase site followed by an aptamer sequence flanked by two reverse complementary sequences was designed. Two variants were prepared, DNA-T and DNA-V, where the incorporated protelomerase target sites were for TelN and VP58.5 respectively (Table 3).

The self-complementary sequences within the oligonucleotide can bind to each other under the right conditions to form a short double stranded sequence, the 3' end of which may be extendable by a DNA polymerase. Extension of the 3' end results in the formation of a full protelomerase site which may be cleaved and joined (by the appropriate protelomerase enzyme) to form the desired circular covalently closed single stranded construct (IbDNA) and a short waste hairpin sequence. Confirmation of a successful reaction is made by treatment with T5 exonuclease as described previously and identification of the surviving band by gel electrophoresis (see FIGS. 18a and 18b).

Reaction Conditions

The 159nt oligonucleotides supplied by IDT had been subjected to standard desalting purification and were diluted to a stock concentration of 200 µM in double distilled water. Each oligonucleotide was then diluted to 3 concentrations—0.1, 0.5 and 1 µM—in 50 µl reaction volumes also containing:

IAB buffer @1× concentration, dNTP mix @100 µM, 1 unit of Phusion® HF DNA polymerase These reactions were cycled as follows: 2 minutes @95° C.; 35 cycles comprising: 30 seconds @95° C. then ramping down at 2° C./sec to 30 seconds @55° C., 30 seconds @ 72° C.; 10 minutes @ 72°; 4° C. END These reactions were split into 10 µl aliquots with NEB buffer 4 added to a final concentration of (1×) and where indicated, protelomerase added to a final concentration of 2.5 µM, to ensure it was in excess. All the aliquots were then incubated for 15 minutes at 37° C.

5 units of T5 exonuclease were then added to indicated aliquots in the presence and absence of protelomerase and incubated at 37° C. for 30 minutes. The temperature was then raised to 75° C. for 15 minutes to heat inactivate the enzymes. Table 4 depicts the enzymes added to each aliquot:

| Aliquot 1 - LH FIG. 18a | Aliquot 2 - RH FIG. 18a | Aliquot 3 - LH FIG. 18b | Aliquot 4 - RH FIG. 18b |
|---|---|---|---|
| No protelomerase No exonuclease | No protelomerase Exonuclease | Protelomerase No exonuclease | Protelomerase Exonuclease |

5 µl of these reactions were loaded and run on 10% TBE PAGE gels, as shown in FIGS. 18a and 18b. FIG. 18a (LH) shows that in the absence of any enzyme, the oligonucleotides ran at their expected size but in the presence of T5 exonuclease, they were completely hydrolysed (FIG. 18a RH).

When exposed to protelomerase, a waste 'cap' or by-product band appeared as well as a corresponding product band (FIG. 18b LH). This confirmed the loopback extension and successful formation of the protelomerase target site (FIG. 18b LH). Subsequent exposure to exonuclease (FIG. 18b RH) revealed a surviving band representing covalently closed circular DNA (IbDNA). This is in contrast to the linear oligonucleotides exposed directly to exonuclease, which were fully hydrolysed (FIG. 18a RH).

The invention claimed is:

1. A single-stranded circular DNA comprising at least one hairpin, wherein the hairpin comprises a portion of a protelomerase target sequence, and wherein the portion is at least 14 bases in length.

2. The single-stranded circular DNA of claim 1, wherein the single-stranded circular DNA molecule comprises a first hairpin comprising a portion of a first protelomerase target sequence and a second hairpin comprising:
   (i) a portion of a second protelomerase target sequence at least 14 bases in length, wherein the first and second protelomerase target sequences are for the same or different protelomerases, or
   (ii) neighbouring complementary sequences.

3. The single-stranded circular DNA of claim 1, wherein said single-stranded circular DNA comprises a loop of single stranded DNA.

4. The single stranded circular DNA of claim 1, wherein said single-stranded circular DNA comprises an aptamer.

5. The single stranded circular DNA of claim 1 wherein said single-stranded circular DNA encodes an antigen.

6. The single stranded circular DNA of claim 1, wherein said single-stranded circular DNA includes a DNA sequence which encodes any one of a DNA aptamer, a protein, a peptide, or an RNA.

7. The single stranded circular DNA of claim 1 wherein said single-stranded circular DNA comprises an expression cassette comprising one or more promoter or enhancer elements and a gene or coding sequence.

8. The single stranded circular DNA of claim 2, wherein said single-stranded sections of the circular DNA are separated by the hairpin structures do not anneal to form a double stranded structure.

9. The single stranded circular DNA of claim 1, wherein said protelomerase target sequence is selected from bacteriophage N15 TelN of SEQ ID NO: 15 or a variant thereof, *Agrobacterium tumefaciens* TelA of SEQ ID NO: 20 or a variant thereof, or *Vibrio parahaemolyticus* plasmid Vp58.5 of SEQ ID NO: 47 or a variant thereof.

10. The single-stranded circular DNA of claim 1, wherein the portion of the protelomerase target sequence is a palindrome.

11. The single-stranded circular DNA of claim 10, wherein the palindrome is a perfect inverted repeat and is flanked by inverted repeat sequences on both sides.

12. A single-stranded circular DNA comprising at least one hairpin, wherein the hairpin comprises at least 14 consecutive bases of a protelomerase target sequence, the protelomerase target sequence being selected from bacteriophage N15 TelN of SEQ ID NO: 15, *Agrobacterium tumefaciens* TelA of SEQ ID NO: 20, or *Vibrio parahaemolyticus* plasmid Vp58.5 of SEQ ID NO: 47.

13. A single-stranded circular DNA comprising at least one hairpin, wherein the hairpin comprises a portion of a protelomerase target sequence, and wherein the portion is at least 14 bases in length and is a perfect inverted repeat.

\* \* \* \* \*